(12) United States Patent
Gai et al.

(10) Patent No.: US 9,193,740 B2
(45) Date of Patent: Nov. 24, 2015

(54) BISMACROCYCLIC COMPOUNDS AS HEPATITIS C VIRUS INHIBITORS

(75) Inventors: Yonghua Gai, North Grafton, MA (US); Yat Sun Or, Watertown, MA (US); Guoqiang Wang, Belmont, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 994 days.

(21) Appl. No.: 12/907,614

(22) Filed: Oct. 19, 2010

(65) Prior Publication Data
US 2011/0123496 A1    May 26, 2011

Related U.S. Application Data

(60) Provisional application No. 61/252,989, filed on Oct. 19, 2009.

(51) Int. Cl.
| C07D 498/22 | (2006.01) |
| A61K 38/12 | (2006.01) |
| A61K 38/21 | (2006.01) |
| A61P 31/14 | (2006.01) |
| A61K 31/495 | (2006.01) |
| A61K 45/06 | (2006.01) |

(52) U.S. Cl.
CPC ............ *C07D 498/22* (2013.01); *A61K 31/495* (2013.01); *A61K 45/06* (2013.01)

(58) Field of Classification Search
None
See application file for complete search history.

(56) References Cited

U.S. PATENT DOCUMENTS

| 6,011,152 A | 1/2000 | Gordon-Wylie et al. |
| 6,121,257 A | 9/2000 | Kawai et al. |
| 6,534,523 B1 | 3/2003 | Bailey et al. |
| 6,608,027 B1 | 8/2003 | Tsantrizos et al. |
| 6,642,204 B2 | 11/2003 | Llinas-Brunet et al. |
| 6,908,901 B2 | 6/2005 | Bailey et al. |
| 6,919,423 B2 | 7/2005 | Llinas-Brunet et al. |
| 7,091,184 B2 | 8/2006 | Llinas-Brunet et al. |
| 7,119,072 B2 | 10/2006 | Llinas-Brunet et al. |
| 7,132,504 B2 | 11/2006 | Scola et al. |
| 7,176,208 B2 | 2/2007 | Nakajima et al. |
| 7,368,452 B2 | 5/2008 | Nakajima et al. |
| 7,582,605 B2 | 9/2009 | Moore et al. |
| 2004/0077551 A1 | 4/2004 | Campbell et al. |

(Continued)

FOREIGN PATENT DOCUMENTS

| WO | 2006119061 A2 | 11/2006 |
| WO | 2007015787 A1 | 2/2007 |
| WO | 2007015855 A1 | 2/2007 |
| WO | 2007016441 A1 | 2/2007 |
| WO | 2008057209 A1 | 5/2008 |
| WO | WO 2008/057208 | * 5/2008 ............ A61K 38/12 |
| WO | 2009010804 A1 | 1/2009 |

(Continued)

OTHER PUBLICATIONS

Wermuth, C. G. Molecular Variations Based on Isosteric Replacements. In The Practice of Medicinal Chemistry (1996); Academic Press, Ltd. pp. 203-237.*

(Continued)

*Primary Examiner* — Kevin S Orwig
(74) *Attorney, Agent, or Firm* — Edgar W. Harlan; Carolyn S. Elmore, Esq.; Elmore Patent Law Group, P.C.

(57) ABSTRACT

The present invention discloses compounds of formula Ia or Ib or pharmaceutically acceptable salts, esters, or prodrugs thereof:

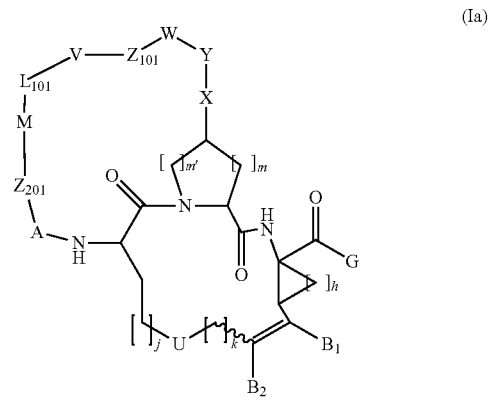

(Ia)

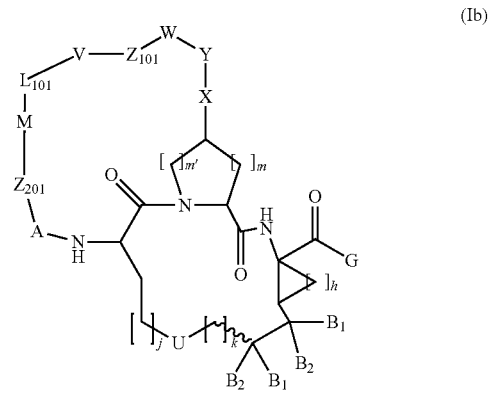

(Ib)

which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

18 Claims, No Drawings

(56) References Cited

U.S. PATENT DOCUMENTS

| | | |
|---|---|---|
| 2004/0106559 A1 | 6/2004 | Wang et al. |
| 2005/0020503 A1 | 1/2005 | Llinas-Brunet et al. |
| 2005/0075279 A1 | 4/2005 | Llinas-Brunet et al. |
| 2005/0080005 A1 | 4/2005 | Llinas-Brunet et al. |
| 2005/0090432 A1 | 4/2005 | McPhee et al. |
| 2005/0143316 A1 | 6/2005 | Tu et al. |
| 2005/0192212 A1 | 9/2005 | Llinas-Brunet et al. |
| 2005/0267040 A1 | 12/2005 | Scola et al. |
| 2007/0021330 A1 | 1/2007 | Wu et al. |
| 2007/0054842 A1 | 3/2007 | Blatt et al. |
| 2007/0060510 A1 | 3/2007 | Nakajima et al. |
| 2007/0099825 A1 | 5/2007 | D'Andrea et al. |
| 2007/0299078 A1 | 12/2007 | Niu et al. |
| 2008/0008681 A1 | 1/2008 | Niu et al. |
| 2008/0032936 A1 | 2/2008 | Gai et al. |
| 2008/0039375 A1 | 2/2008 | Moore et al. |
| 2008/0107623 A1 | 5/2008 | D'Andrea et al. |
| 2008/0107624 A1 | 5/2008 | D'Andrea et al. |
| 2008/0107625 A1 | 5/2008 | D'Andrea et al. |
| 2008/0119461 A1 | 5/2008 | Sin et al. |
| 2008/0267916 A1 | 10/2008 | Gai et al. |
| 2008/0267917 A1 | 10/2008 | Niu et al. |
| 2008/0287449 A1 | 11/2008 | Niu et al. |
| 2009/0005387 A1 | 1/2009 | Niu et al. |
| 2009/0098085 A1 | 4/2009 | Sun et al. |
| 2009/0123425 A1 | 5/2009 | Moore et al. |
| 2009/0142299 A1 | 6/2009 | Sun et al. |
| 2009/0180981 A1 | 7/2009 | Niu et al. |
| 2009/0180984 A1 | 7/2009 | Sun et al. |
| 2009/0180985 A1 | 7/2009 | Liu et al. |
| 2009/0191151 A1 | 7/2009 | Gai et al. |
| 2009/0197888 A1 | 8/2009 | Gai et al. |
| 2009/0238794 A1 | 9/2009 | Gai et al. |
| 2009/0274657 A1 | 11/2009 | Gai et al. |
| 2009/0285773 A1 | 11/2009 | Sun et al. |
| 2009/0285774 A1 | 11/2009 | Sin et al. |
| 2009/0306085 A1 | 12/2009 | Petter et al. |
| 2010/0003214 A1 | 1/2010 | Gai et al. |
| 2010/0080770 A1 | 4/2010 | Hiebert et al. |
| 2010/0080771 A1 | 4/2010 | Hiebert et al. |
| 2011/0033420 A1 | 2/2011 | Gai et al. |
| 2012/0070416 A1 | 3/2012 | Or et al. |
| 2012/0141414 A1* | 6/2012 | Majer et al. .................. 424/85.4 |

FOREIGN PATENT DOCUMENTS

| | | |
|---|---|---|
| WO | 2009064975 A1 | 5/2009 |
| WO | 2009134624 A1 | 11/2009 |
| WO | 2010065577 A1 | 6/2010 |
| WO | 2010135748 A1 | 11/2010 |

OTHER PUBLICATIONS

Patani, G. A. et al. (1996) Chem. Rev. 96; pp. 3147-3176.*

Ismail, F. M. D. J. Fluorine Chem. (2002), 118; pp. 27-33.*

Harper, et al., "Inhibitors of Hepatitis C Virus NS3 Protease with Basic Amine Functionality at the P3-Amino Acid N-Terminus: Discovery and Optimization of a New Series of P2-P4 Macrocycles," Journal of Medicinal Chemistry, 52:4820-4837, 2009.

McCauley, et al., "Bismacrocyclic Inhibitors of Hepatitis C NS3/4a Protease," Angewandte Chemie, International Edition, 47:9104-9107, 2008.

International Search Report for PCT/US2010/053129, dated Jul. 25, 2011.

Liverton, et al., "Molecular Modeling Based Approach to Potent P2-P4 Macrocyclic Inhibitors of Hepatitis C NS3/4A Protease", J. Am. Chem. Soc., 130(14), pp. 4607-4609, 2008.

* cited by examiner

BISMACROCYCLIC COMPOUNDS AS HEPATITIS C VIRUS INHIBITORS

RELATED APPLICATION

This application claims the benefit of U.S. Provisional Application No. 61/252,989, filed on Oct. 19, 2009. The entire teaching of the above application is incorporated herein by reference.

TECHNICAL FIELD

The present invention relates to novel hepatitis C virus (HCV) protease inhibitor compounds having antiviral activity against HCV and useful in the treatment of HCV infections. More particularly, the invention relates to bismacrocyclic compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3-12 month course of intravenous interferon-α (IFN-α), while a new approved second-generation treatment involves co-treatment with IFN-α and the general antiviral nucleoside mimics like ribavirin. Both of these treatments suffer from interferon related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug would desirably possess significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS3-NS4A protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, *Nature Rev. Drug Discov.*, 1, 867-881 (2002).

SUMMARY OF THE INVENTION

The present invention relates to bismacrocyclic compounds and pharmaceutically acceptable salts, esters or prodrugs thereof, and methods of using the same to treat hepatitis C infection in a subject in need of such therapy. Compounds of the present invention interfere with the life cycle of the hepatitis C virus and are also useful as antiviral agents. The present invention further relates to pharmaceutical compositions comprising the aforementioned compounds, salts, esters or prodrugs for administration to a subject suffering from HCV infection. The present invention further features pharmaceutical compositions comprising a compound of the present invention (or a pharmaceutically acceptable salt, ester or prodrug thereof) and another anti-HCV agent, such as interferon (e.g., alpha-interferon, beta-interferon, consensus interferon, pegylated interferon, or albumin or other conjugated interferon), ribavirin, amantadine, another HCV protease inhibitor, or an HCV polymerase, helicase or internal ribosome entry site inhibitor. The invention also relates to methods of treating an HCV infection in a subject by administering to the subject a pharmaceutical composition of the present invention. The present invention further relates to pharmaceutical compositions comprising the compounds of the present invention, or pharmaceutically acceptable salts, esters, or prodrugs thereof, in combination with a pharmaceutically acceptable carrier or excipient.

In one embodiment of the present invention there are disclosed compounds represented by Formula Ia or Ib, or pharmaceutically acceptable salts, esters, or prodrugs thereof:

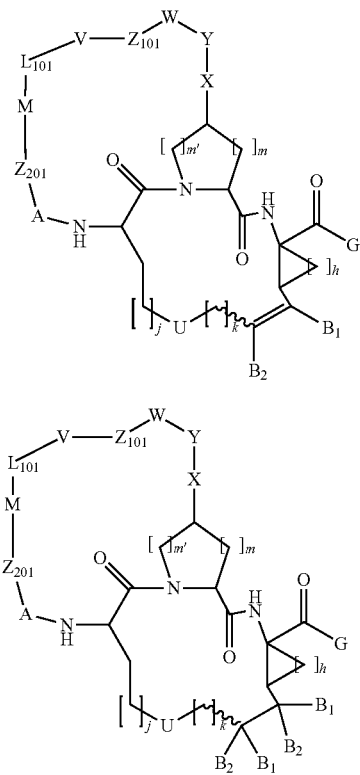

wherein;
A is absent or selected from —C(O)—, —S(O)$_2$—, —C(=N—OR$_1$)— and —C(=N—CN)—;
Z$_{201}$ is absent or selected from —C$_1$-C$_8$ alkylene, —C$_2$-C$_8$ alkenylene, or —C$_2$-C$_8$ alkynylene each containing 0, 1, 2, or 3 heteroatoms selected from O, S, or N; substituted —C$_1$-C$_8$ alkylene, including but not limited to halogenated —C$_1$-C$_8$ alkylene, substituted —C$_2$-C$_8$ alkenylene, including but not limited to halogenated —C$_2$-C$_8$ alkenylene or substituted —C$_2$-C$_8$ alkynylene, including but not limited to halogenated —C$_2$-C$_8$ alkynylene each containing 0, 1, 2, or 3 heteroatoms selected from O, S or N; —C$_3$-C$_{12}$ cycloalkylene, or —C$_3$-C$_{12}$ cycloalkenylene each containing 0, 1, 2, or 3 heteroatoms selected from O, S or N; substituted —C$_3$-C$_{12}$ cycloalkylene, including but not limited to halogenated —C$_3$-C$_{12}$ cycloalkylene, and substituted —C$_3$-C$_{12}$ cycloalkenylene, including but not limited to halogenated —C$_3$-C$_{12}$ cycloalkenylene each containing 0, 1, 2, or 3 heteroatoms selected from O, S or N; aryl, substituted aryl, heteroaryl, or substituted heteroaryl;
M is absent or selected from O, S, SO, SO$_2$ and NR$_1$;
L$_{101}$ is absent or selected from —C$_1$-C$_8$ alkylene, —C$_2$-C$_8$ alkenylene, or —C$_2$-C$_8$ alkynylene each containing 0, 1, 2, or 3 heteroatoms selected from O, S, or N; substituted —C$_1$-C$_8$ alkylene, including but not limited to halogenated —C$_1$-C$_8$ alkylene, substituted —C$_2$-C$_8$ alkenylene, including but not limited to halogenated —C$_2$-C$_8$ alkenylene or substituted —C$_2$-C$_8$ alkynylene, including but not limited to halogenated —C$_2$-C$_8$ alkynylene each containing 0, 1, 2, or 3 heteroatoms selected from O, S or N; —C$_3$-C$_{12}$ cycloalkylene, or —C$_3$-C$_{12}$ cycloalkenylene each containing 0, 1, 2, or 3 heteroatoms selected from O, S or N; substituted —C$_3$-C$_{12}$ cycloalkylene, including but not limited to halogenated —C$_3$-C$_{12}$ cycloalkylene, and substituted —C$_3$-C$_{12}$ cycloalkenylene, including but not limited to halogenated —C$_3$-C$_{12}$ cycloalkenylene each containing 0, 1, 2, or 3 heteroatoms selected from O, S or N;
V is absent or is selected from O, S, S(O), S(O)$_2$ and NR$_1$; wherein R$_1$ is selected at each occurrence from the group consisting of:
(i) hydrogen;
(ii) aryl; substituted aryl; heteroaryl; substituted heteroaryl;
(iii) heterocycloalkyl or substituted heterocycloalkyl;
(iv) —C$_1$-C$_8$ alkyl, —C$_2$-C$_8$ alkenyl, or —C$_2$-C$_8$ alkynyl each containing 0, 1, 2, or 3 heteroatoms selected from O, S, or N; substituted —C$_1$-C$_8$ alkyl, substituted —C$_2$-C$_8$ alkenyl, or substituted —C$_2$-C$_8$ alkynyl each containing 0, 1, 2, or 3 heteroatoms selected from O, S or N; —C$_3$-C$_{12}$ cycloalkyl, or substituted —C$_3$-C$_{12}$ cycloalkyl; —C$_3$-C$_{12}$ cycloalkenyl, or substituted —C$_3$-C$_{12}$ cycloalkenyl;
Z$_{101}$ is absent or selected from aryl, substituted aryl, heteroaryl, and substituted heteroaryl;
X is absent or is selected from the group consisting of:
(1) oxygen;
(2) sulfur;
(3) NR$_1$; where R$_1$ is as previously defined above; and
(4) —O—NH—;
Y is absent or is selected from the group consisting of:
(i) —C(=O)—, —C(=O)—NH—, —S(O)$_2$—, —S(O)$_2$NH—;
(ii) —C$_1$-C$_6$ alkyl containing 0, 1, 2, or 3 heteroatoms selected from O, S, or N, optionally substituted with one or more substituents selected from halogen, aryl, substituted aryl, heteroaryl, or substituted heteroaryl;
(iii) —C$_2$-C$_6$ alkenyl containing 0, 1, 2, or 3 heteroatoms selected from O, S, or N, optionally substituted with one or more substituents selected from halogen, aryl, substituted aryl, heteroaryl, or substituted heteroaryl;
(iv) —C$_2$-C$_6$ alkynyl containing 0, 1, 2, or 3 heteroatoms selected from O, S, or N, optionally substituted with one or more substituents selected from halogen, aryl, substituted aryl, heteroaryl, or substituted heteroaryl; and
(v) —C$_3$-C$_{12}$ cycloalkyl, substituted —C$_3$-C$_{12}$ cycloalkyl, heterocycloalkyl, substituted heterocycloalkyl;
W is selected from the group consisting of aryl, substituted aryl, heteroaryl, substituted heteroaryl, cycloalkyl, substituted cycloalkyl, heterocycloalkyl, substituted heterocycloalkyl; each of which is optionally fused with one or more aryl, substituted aryl, heteroaryl; substituted heteroaryl, cycloalkyl, substituted cycloalkyl, heterocycloalkyl; substituted heterocycloalkyl;
G is selected from —OH, —NHS(O)$_2$—R$_2$, —NH(SO$_2$)NR$_3$R$_4$, and NR$_3$R$_4$;
R$_2$ is selected from:
(i) aryl; substituted aryl; heteroaryl; substituted heteroaryl;
(ii) heterocycloalkyl; substituted heterocycloalkyl; and
(iii) —C$_1$-C$_8$ alkyl, —C$_2$-C$_8$ alkenyl, or —C$_2$-C$_8$ alkynyl each containing 0, 1, 2, or 3 heteroatoms selected from O, S or N, substituted —C$_1$-C$_8$ alkyl, substituted —C$_2$-C$_8$ alkenyl, or substituted —C$_2$-C$_8$ alkynyl each containing 0, 1, 2, or 3 heteroatoms selected from O, S or N; —C$_3$-C$_{12}$ cycloalkyl, or substituted —C$_3$-C$_{12}$ cycloalkyl; —$C_3$-$C_{12}$ cycloalkenyl, or substituted —$C_3$-$C_{12}$ cycloalkenyl; heterocylic; substituted heterocyclic;

$R_3$ and $R_4$ are independently selected from:
(i) hydrogen;
(ii) aryl; substituted aryl; heteroaryl; substituted heteroaryl;
(iii) heterocycloalkyl or substituted heterocycloalkyl; and
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl; heterocyclic, or substituted heterocyclic;

alternatively, $R_3$ and $R_4$ are taken together with the nitrogen they are attached to form a heterocyclic or substituted heterocyclic;

U is absent or is selected from —$C_1$-$C_8$ alkylene, substituted —$C_1$-$C_8$ alkylene, including but not limited to halogenated —$C_1$-$C_8$ alkylene, O, S, SO, $SO_2$ or $NR_1$ where $R_1$ is as previously defined;

each $B_1$ and $B_2$ is independently selected from H and F;
m is 0, 1, 2 or 3;
m' is 1, 2 or 3;
h is 0, 1, 2 or 3;
k is 0, 1, 2 or 3; and
j is 0, 1, 2 or 3.

In another embodiment, the present invention features pharmaceutical compositions comprising a compound of the invention, or a pharmaceutically acceptable salt, ester or prodrug thereof. In still another embodiment of the present invention there are disclosed pharmaceutical compositions comprising a therapeutically effective amount of a compound of the invention, or a pharmaceutically acceptable salt, ester or prodrug thereof, in combination with a pharmaceutically acceptable carrier or excipient. In yet another embodiment of the invention are methods of treating a hepatitis C infection in a subject in need of such treatment with said pharmaceutical compositions.

DETAILED DESCRIPTION OF THE INVENTION

A first embodiment of the invention is a compound represented by Formula I as described above, or a pharmaceutically acceptable salt, ester or prodrug thereof.

Another embodiment of the invention is a compound represented by Formula II:

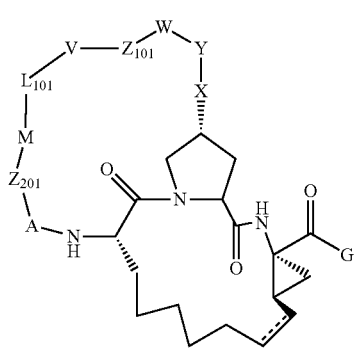

(II)

or a pharmaceutically acceptable salt, ester or prodrug thereof, where A, $Z_{201}$, M, $L_{101}$, V, $Z_{101}$, W Y, X, and G are as defined in Formula I, and ----- denotes a carbon-carbon single or double bond.

Another embodiment of the invention is a compound represented by Formula III:

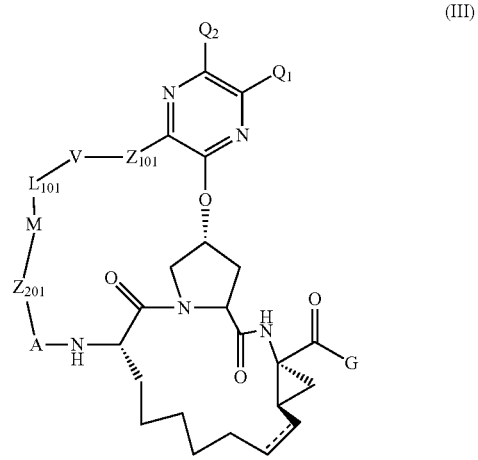

(III)

or a pharmaceutically acceptable salt, ester or prodrug thereof, where $Q_1$ and $Q_2$ taken together with the carbon atoms to which they are attached to form a carbocyclic moiety or a heterocyclic moiety. The carbocyclic or heterocyclic moiety can be selected from aryl, substituted aryl, heteroaryl, substituted heteroaryl, cycloalkyl, substituted cycloalkyl, cycloalkenyl, substituted cycloalkenyl, heterocyclic, or substituted heterocylic; and A, $Z_{201}$, M, $L_{101}$, V, $Z_{101}$ and G are as defined in Formula I.

Another embodiment of the invention is a compound represented by Formula IV:

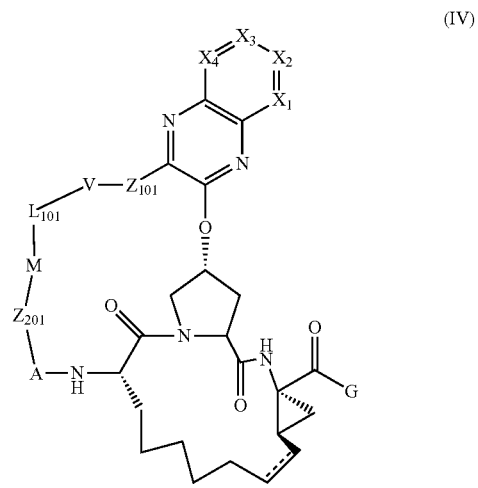

(IV)

or a pharmaceutically acceptable salt, ester or prodrug thereof, where $X_1$-$X_4$ are independently selected from —$CR_5$ and N, wherein $R_5$ is independently selected from:
(i) hydrogen; halogen; —$NO_2$; —CN; $N_3$; $CF_3$;
(ii) -M-$R_4$, M is O, S, NH;
(iii) $NR_3R_4$;
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-

$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

(v) aryl; substituted aryl; heteroaryl; substituted heteroaryl;

(vi) heterocycloalkyl or substituted heterocycloalkyl;

where $R_3$, $R_4$, A, $Z_{201}$, M, $L_{101}$, V, $Z_{101}$ and G are as previously defined.

Another embodiment of the invention is a compound represented by Formula V:

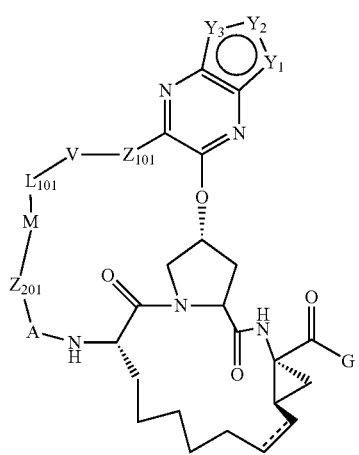

(V)

or a pharmaceutically acceptable salt, ester or prodrug thereof, where $Y_1$-$Y_3$ are independently selected from $CR_5$, N, $NR_5$, S and O; where $R_5$, A, $Z_{201}$, M, $L_{101}$, V, $Z_{101}$ and G are as previously defined.

Representative compounds of the invention include, but are not limited to, the following compounds (Table 1) according to Formula VI or Formula VII wherein M-L, $Ar^2$, $Ar^1$ and G are delineated for each example in Table 1.

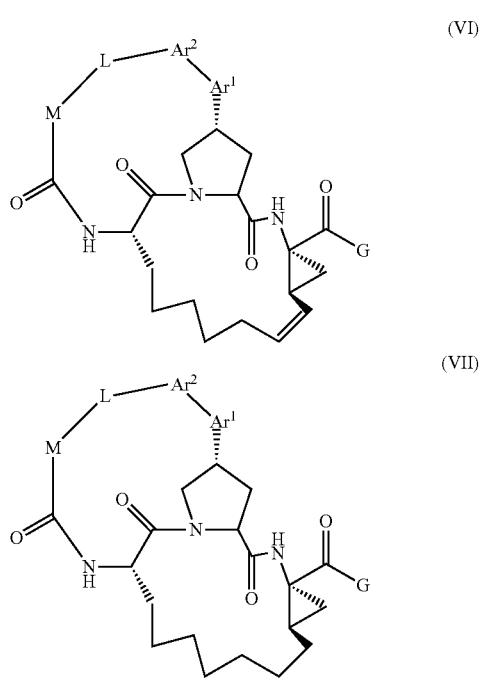

TABLE 1

| Example # | M—L | $Ar^2$ | $Ar^1$ | G | Formula |
|---|---|---|---|---|---|
| 1. | ![](F,F diether) | phenyl | quinoxalinyl-O | OH | VI |
| 2. | ![](F,F diether) | phenyl | quinoxalinyl-O | NHS(O)₂cyclopropyl | VI |
| 3. | ![](F,F diether) | phenyl | quinoxalinyl-O | NHS(O)₂cyclopropyl | VII |
| 4. | | phenyl | quinoxalinyl-O | OH | VI |

TABLE 1-continued
| Example # | M—L | Ar² | Ar¹ | G | Formula |
|---|---|---|---|---|---|
| 5. | 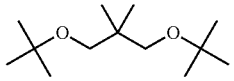 | 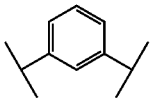 | 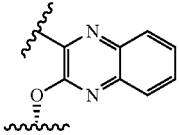 | 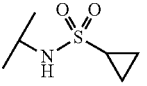 | VI |
| 6. |  | 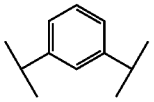 | 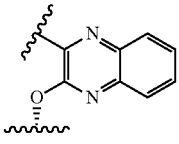 | 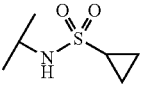 | VII |
| 7. | 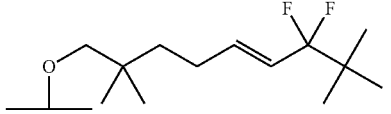 | Absent | 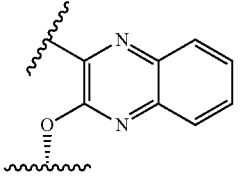 | OH | VI |
| 8. | 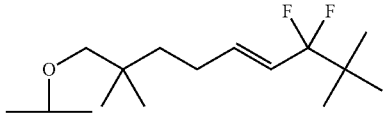 | Absent | 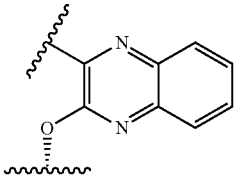 | 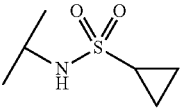 | VI |
| 9. | 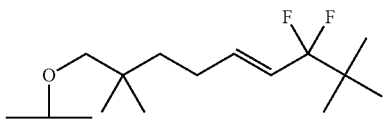 | Absent | 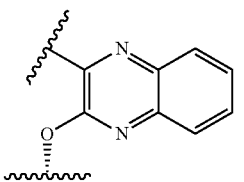 | 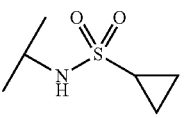 | VII |
| 10. | 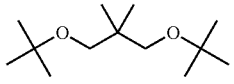 | 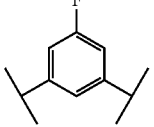 | 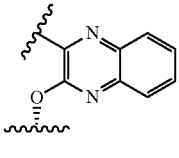 | OH | VI |
| 11. | 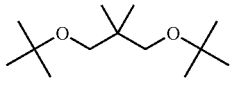 | 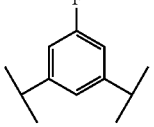 | 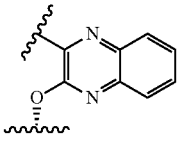 | 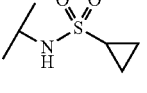 | VI |
| 12. | 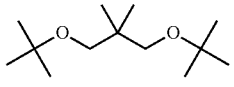 | 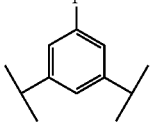 | 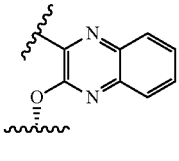 | 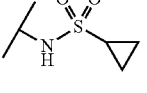 | VII |
| 13. | 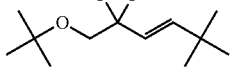 | 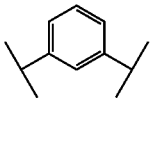 | 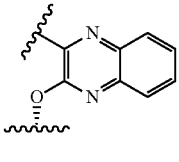 | OH | VI |

TABLE 1-continued
| Example # | M—L | Ar² | Ar¹ | G | Formula |
|---|---|---|---|---|---|
| 14. | 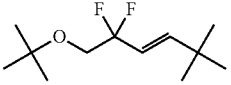 | 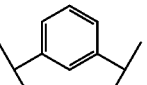 | 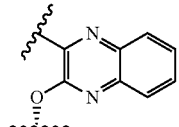 | 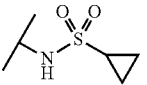 | VI |
| 15. | 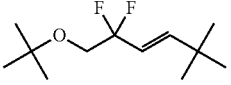 | 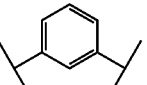 | 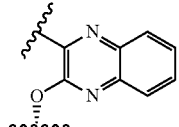 | 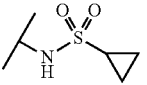 | VII |
| 16. | 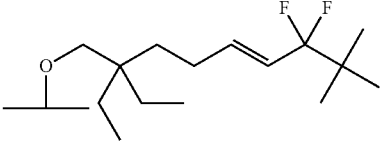 | Absent | 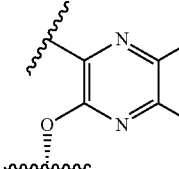 | 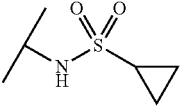 | VI |
| 17. | 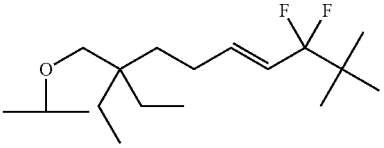 | Absent | 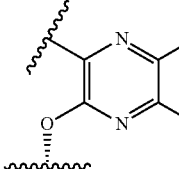 | 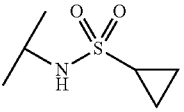 | VII |
| 18. | 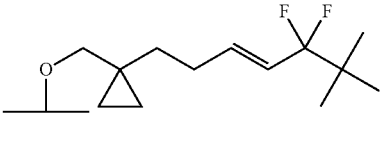 | Absent | 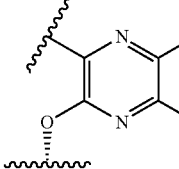 | 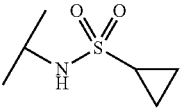 | VI |
| 19. | 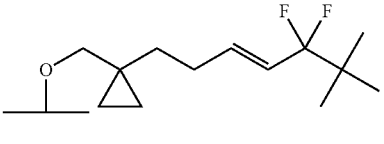 | Absent | 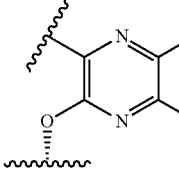 | 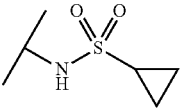 | VII |
| 20. | 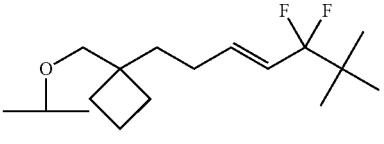 | Absent | 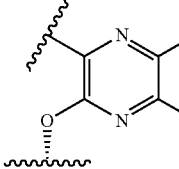 | 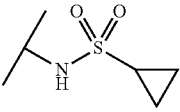 | VI |
| 21. | 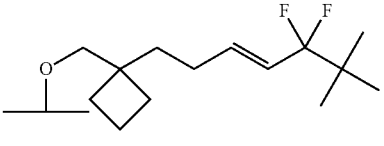 | Absent | 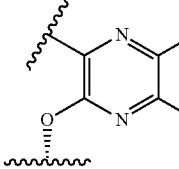 | 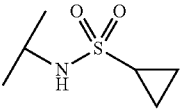 | VII |

TABLE 1-continued

| Example # | M—L | Ar² | Ar¹ | G | Formula |
|---|---|---|---|---|---|
| 22. | | Absent | | | VI |
| 23. | | Absent | | | VII |
| 24. | | Absent | | | VI |
| 25. | | Absent | | | VII |
| 26. | | Absent | | | VI |
| 27. | | Absent | | | VII |
| 28. | | Absent | | | VI |
| 29. | | Absent | | | VII |

TABLE 1-continued

| Example # | M—L | Ar² | Ar¹ | G | Formula |
|---|---|---|---|---|---|
| 30. | | Absent | | | VI |
| 31. | | Absent | | | VII |
| 32. | | Absent | | | VI |
| 33. | | Absent | | | VII |
| 34. | | Absent | | | VI |
| 35. | | Absent | | | VII |
| 36. | | Absent | | | VI |
| 37. | | Absent | | | VII |

TABLE 1-continued
| Example # | M—L | Ar² | Ar¹ | G | Formula |
|---|---|---|---|---|---|
| 38. | 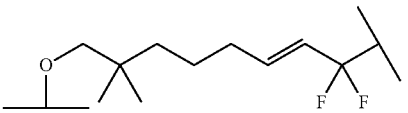 | Absent | 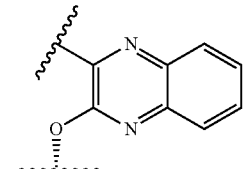 | 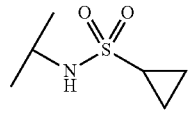 | VI |
| 39. | 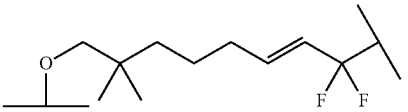 | Absent | 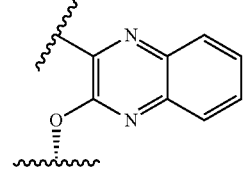 | 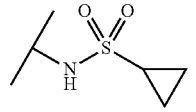 | VII |
| 40. | 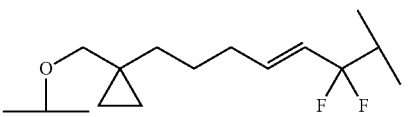 | Absent | 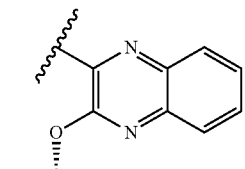 | 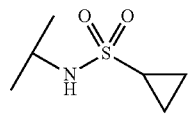 | VI |
| 41. | 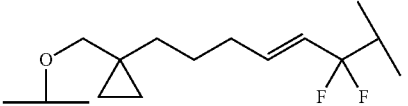 | Absent | 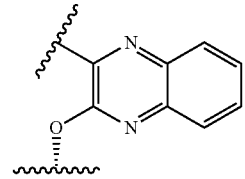 | 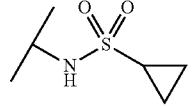 | VII |
| 42. | 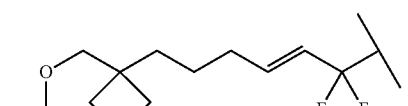 | Absent | 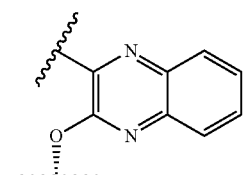 | 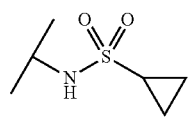 | VI |
| 43. | 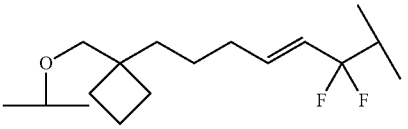 | Absent | 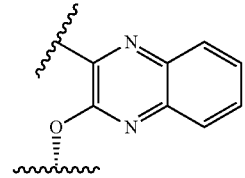 | 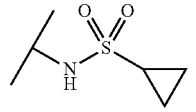 | VII |
| 44. | 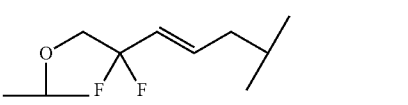 | Absent | 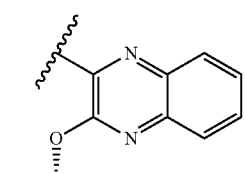 | 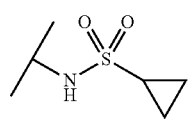 | VI |
| 45. | 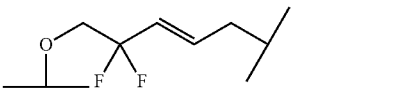 | Absent | 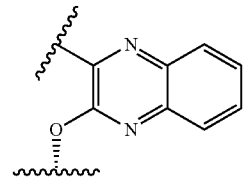 | 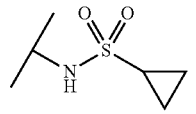 | VII |

TABLE 1-continued
| Example # | M—L | Ar² | Ar¹ | G | Formula |
|---|---|---|---|---|---|
| 46. | 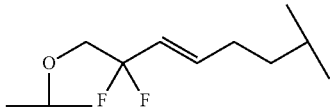 | Absent | 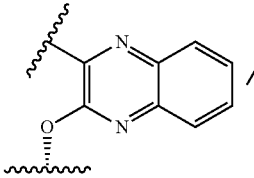 | 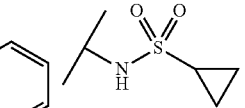 | VI |
| 47. | 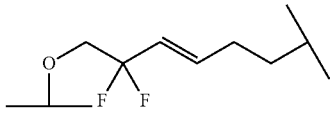 | Absent | 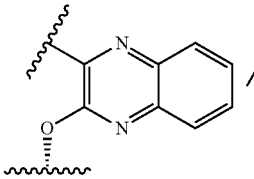 | 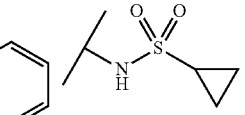 | VII |
| 48. | 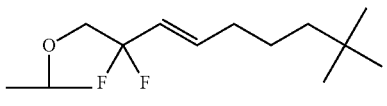 | Absent | 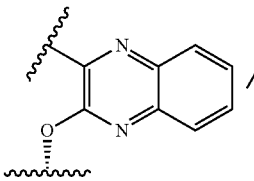 | 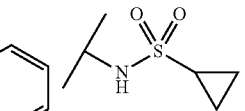 | VI |
| 49. | 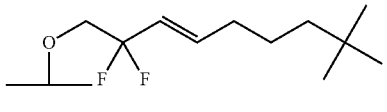 | Absent | 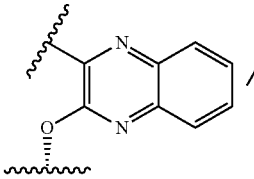 | 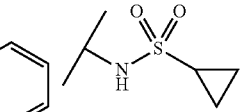 | VII |
| 50. | 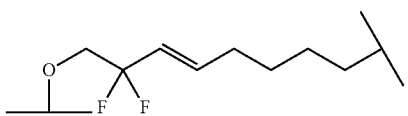 | Absent | 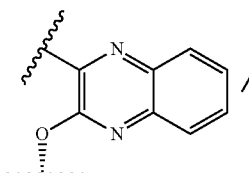 | 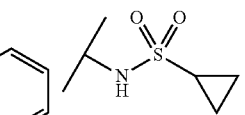 | VI |
| 51. | 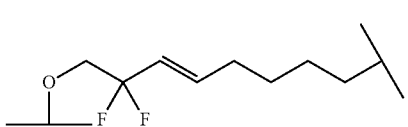 | Absent | 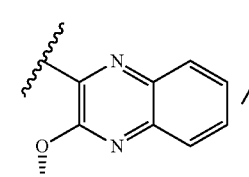 | 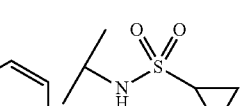 | VII |
| 52. | 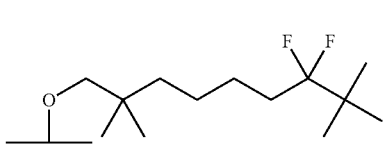 | Absent | 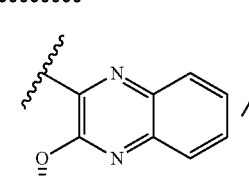 | 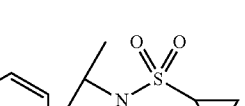 | VI |
| 53. | 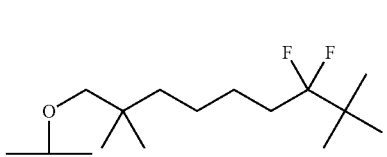 | Absent | 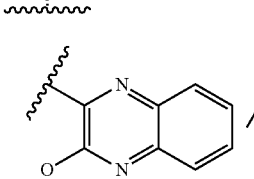 | 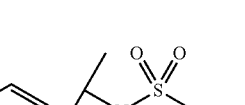 | VII |

TABLE 1-continued
| Example # | M—L | Ar² | Ar¹ | G | Formula |
|---|---|---|---|---|---|
| 54. | 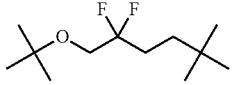 | 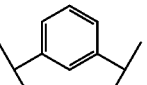 | 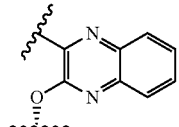 | 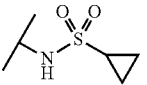 | VI |
| 55. | 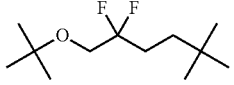 | 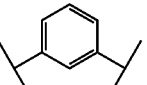 | 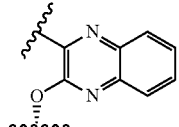 | 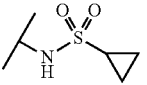 | VII |
| 56. | 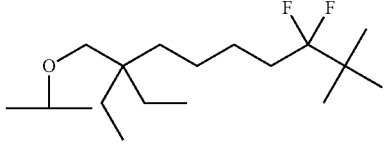 | Absent | 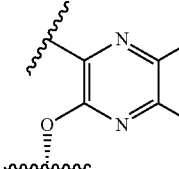 | 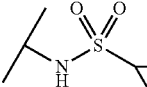 | VI |
| 57. | 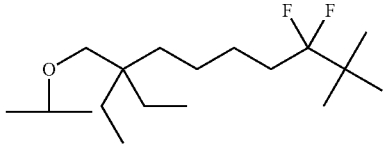 | Absent | 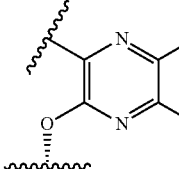 | 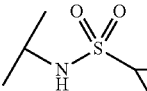 | VII |
| 58. | 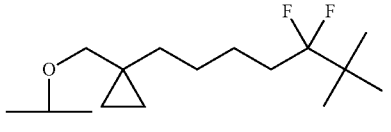 | Absent | 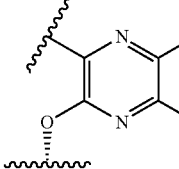 | 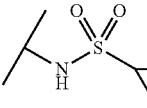 | VI |
| 59. | 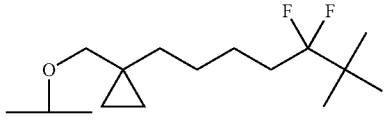 | Absent | 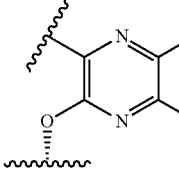 | 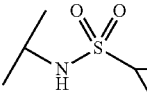 | VII |
| 60. | 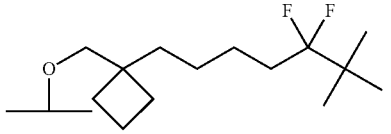 | Absent | 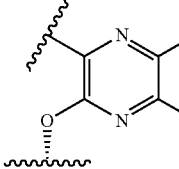 | 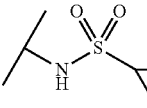 | VI |
| 61. | 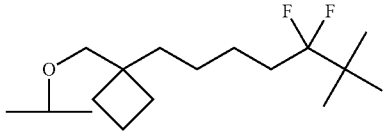 | Absent | 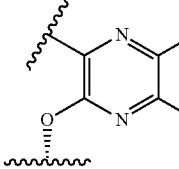 | 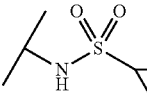 | VII |

TABLE 1-continued

| Example # | M—L | Ar² | Ar¹ | G | Formula |
|---|---|---|---|---|---|
| 62. | (cyclopentane with OCH₂ and chain to C(F)(F)C(CH₃)₃) | Absent | (quinoxaline with O) | (C(CH₃)NHSO₂-cyclopropyl) | VI |
| 63. | (cyclopentane with OCH₂ and chain to C(F)(F)C(CH₃)₃) | Absent | (quinoxaline with O) | (C(CH₃)NHSO₂-cyclopropyl) | VII |
| 64. | (cyclohexane with OCH₂ and chain to C(F)(F)C(CH₃)₃) | Absent | (quinoxaline with O) | (C(CH₃)NHSO₂-cyclopropyl) | VI |
| 65. | (cyclohexane with OCH₂ and chain to C(F)(F)C(CH₃)₃) | Absent | (quinoxaline with O) | (C(CH₃)NHSO₂-cyclopropyl) | VII |
| 66. | (gem-dimethyl with OCH₂ and chain to CF₂CH(CH₃)₂) | Absent | (quinoxaline with O) | (C(CH₃)NHSO₂-cyclopropyl) | VI |
| 67. | (gem-dimethyl with OCH₂ and chain to CF₂CH(CH₃)₂) | Absent | (quinoxaline with O) | (C(CH₃)NHSO₂-cyclopropyl) | VII |
| 68. | (cyclopropane with OCH₂ and chain to CF₂CH(CH₃)₂) | Absent | (quinoxaline with O) | (C(CH₃)NHSO₂-cyclopropyl) | VI |
| 69. | (cyclopropane with OCH₂ and chain to CF₂CH(CH₃)₂) | Absent | (quinoxaline with O) | (C(CH₃)NHSO₂-cyclopropyl) | VII |

TABLE 1-continued

| Example # | M—L | Ar² | Ar¹ | G | Formula |
|---|---|---|---|---|---|
| 70. | | Absent | | | VI |
| 71. | | Absent | | | VII |
| 72. | | Absent | | | VI |
| 73. | | Absent | | | VII |
| 74. | | Absent | | | VI |
| 75. | | Absent | | | VII |
| 76. | | Absent | | | VI |
| 77. | | Absent | | | VII |

TABLE 1-continued
| Example # | M—L | Ar² | Ar¹ | G | Formula |
|---|---|---|---|---|---|
| 78. | 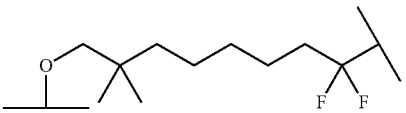 | Absent | 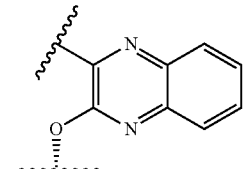 | 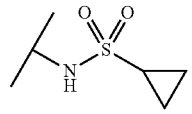 | VI |
| 79. | 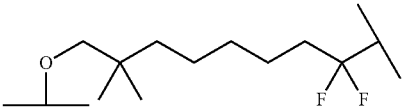 | Absent | 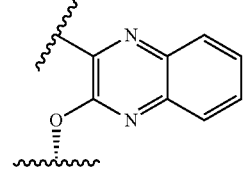 | 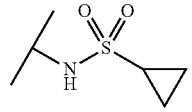 | VII |
| 80. | 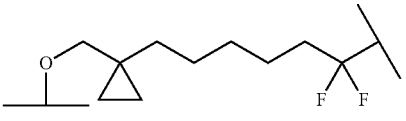 | Absent | 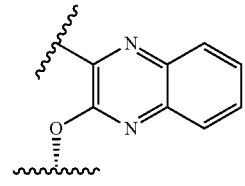 | 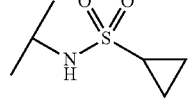 | VI |
| 81. | 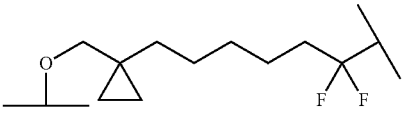 | Absent | 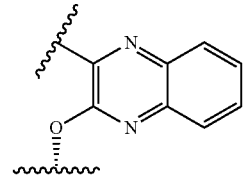 | 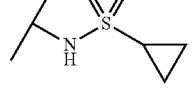 | VII |
| 82. | 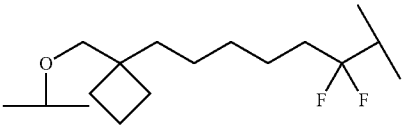 | Absent | 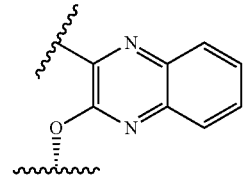 | 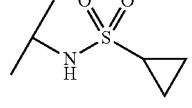 | VI |
| 83. | 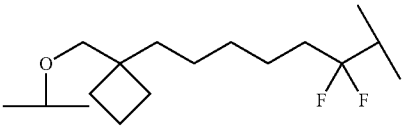 | Absent | 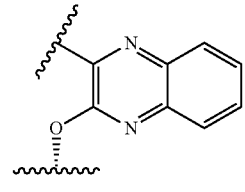 | 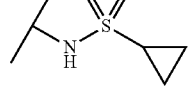 | VII |
| 84. | 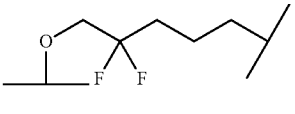 | Absent | 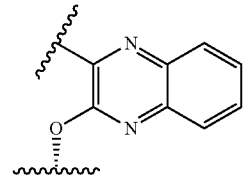 | 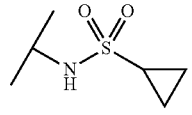 | VI |
| 85. | 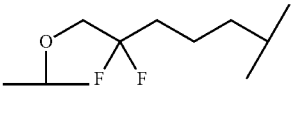 | Absent | 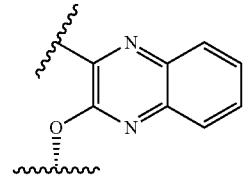 | 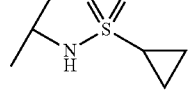 | VII |

TABLE 1-continued
| Example # | M—L | Ar² | Ar¹ | G | Formula |
|---|---|---|---|---|---|
| 86. | 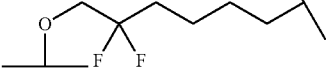 | Absent | 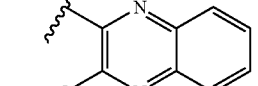 | 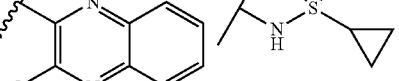 | VI |
| 87. |  | Absent |  |  | VII |
| 88. | 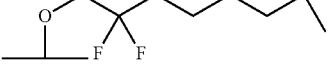 | Absent | 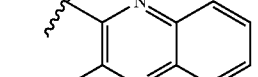 | 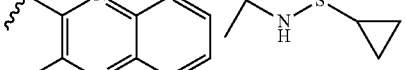 | VI |
| 89. |  | Absent |  |  | VII |
| 90. |  | Absent | 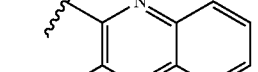 | 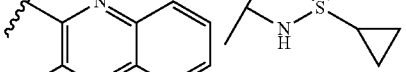 | VI |
| 91. |  | Absent |  |  | VII |
| 92. |  | 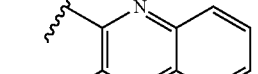 | 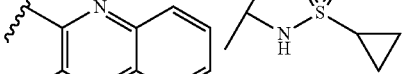 | OH | VI |
| 93. |  |  |  | 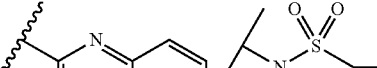 | VI |

TABLE 1-continued

| Example # | M—L | Ar² | Ar¹ | G | Formula |
|---|---|---|---|---|---|
| 94. | (gem-dimethyl diether with CF₂) | 1,3-phenylene | quinolin-3-yl, 2-O- | NHS(O)₂-cyclopropyl | VII |
| 95. | (gem-dimethyl diether) | 1,3-phenylene | quinolin-3-yl, 2-O- | OH | VI |
| 96. | (gem-dimethyl diether) | 1,3-phenylene | quinolin-3-yl, 2-O- | NHS(O)₂-cyclopropyl | VI |
| 97. | (gem-dimethyl diether) | 1,3-phenylene | quinolin-3-yl, 2-O- | NHS(O)₂-cyclopropyl | VII |
| 98. | (ether alkene CF₂ tBu chain) | Absent | quinolin-3-yl, 2-O- | OH | VI |
| 99. | (ether alkene CF₂ tBu chain) | Absent | quinolin-3-yl, 2-O- | NHS(O)₂-cyclopropyl | VI |
| 100. | (ether alkene CF₂ tBu chain) | Absent | quinolin-3-yl, 2-O- | NHS(O)₂-cyclopropyl | VII |
| 101. | (gem-dimethyl diether) | 5-fluoro-1,3-phenylene | quinolin-3-yl, 2-O- | OH | VI |
| 102. | (gem-dimethyl diether) | 5-fluoro-1,3-phenylene | quinolin-3-yl, 2-O- | NHS(O)₂-cyclopropyl | VI |

TABLE 1-continued

| Example # | M—L | Ar² | Ar¹ | G | Formula |
|---|---|---|---|---|---|
| 103. | | 3-F-phenylene | 3-quinolinyl, 2-O-linked | NHSO₂-cyclopropyl | VII |
| 104. | | 1,3-phenylene | 3-quinolinyl, 2-O-linked | OH | VI |
| 105. | | 1,3-phenylene | 3-quinolinyl, 2-O-linked | NHSO₂-cyclopropyl | VI |
| 106. | | 1,3-phenylene | 3-quinolinyl, 2-O-linked | NHSO₂-cyclopropyl | VII |
| 107. | | Absent | 3-quinolinyl, 2-O-linked | NHSO₂-cyclopropyl | VI |
| 108. | | Absent | 3-quinolinyl, 2-O-linked | NHSO₂-cyclopropyl | VII |
| 109. | | Absent | 3-quinolinyl, 2-O-linked | NHSO₂-cyclopropyl | VI |
| 110. | | Absent | 3-quinolinyl, 2-O-linked | NHSO₂-cyclopropyl | VII |

TABLE 1-continued

| Example # | M—L | Ar² | Ar¹ | G | Formula |
|---|---|---|---|---|---|
| 111. | | Absent | quinoline | cyclopropylsulfonamide | VI |
| 112. | | Absent | quinoline | cyclopropylsulfonamide | VII |
| 113. | | Absent | quinoline | cyclopropylsulfonamide | VI |
| 114. | | Absent | quinoline | cyclopropylsulfonamide | VII |
| 115. | | Absent | quinoline | cyclopropylsulfonamide | VI |
| 116. | | Absent | quinoline | cyclopropylsulfonamide | VII |
| 117. | | Absent | quinoline | cyclopropylsulfonamide | VI |
| 118. | | Absent | quinoline | cyclopropylsulfonamide | VII |

TABLE 1-continued

| Example # | M—L | Ar² | Ar¹ | G | Formula |
|---|---|---|---|---|---|
| 119. | | Absent | | | VI |
| 120. | | Absent | | | VII |
| 121. | | Absent | | | VI |
| 122. | | Absent | | | VII |
| 123. | | Absent | | | VI |
| 124. | | Absent | | | VII |
| 125. | | Absent | | | VI |
| 126. | | Absent | | | VII |

TABLE 1-continued

| Example # | M—L | Ar² | Ar¹ | G | Formula |
|---|---|---|---|---|---|
| 127. | (structure) | Absent | (quinoline structure) | (cyclopropanesulfonamide) | VI |
| 128. | (structure) | Absent | (quinoline structure) | (cyclopropanesulfonamide) | VII |
| 129. | (structure) | Absent | (quinoline structure) | (cyclopropanesulfonamide) | VI |
| 130. | (structure) | Absent | (quinoline structure) | (cyclopropanesulfonamide) | VII |
| 131. | (structure) | Absent | (quinoline structure) | (cyclopropanesulfonamide) | VI |
| 132. | (structure) | Absent | (quinoline structure) | (cyclopropanesulfonamide) | VII |
| 133. | (structure) | Absent | (quinoline structure) | (cyclopropanesulfonamide) | VI |
| 134. | (structure) | Absent | (quinoline structure) | (cyclopropanesulfonamide) | VII |

TABLE 1-continued
| Example # | M—L | Ar² | Ar¹ | G | Formula |
|---|---|---|---|---|---|
| 135. | 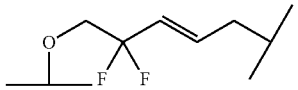 | Absent | 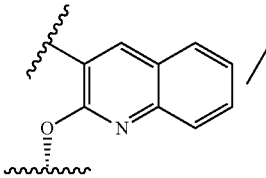 | 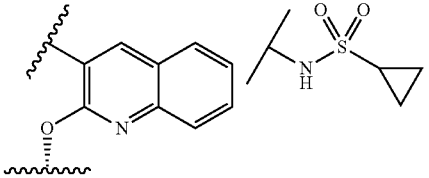 | VI |
| 136. | 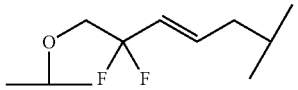 | Absent | 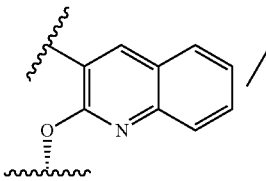 | 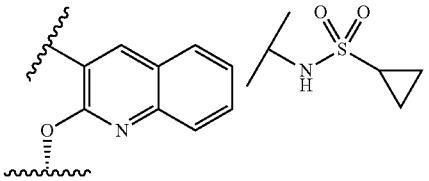 | VII |
| 137. | 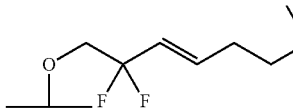 | Absent | 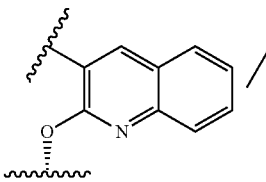 | 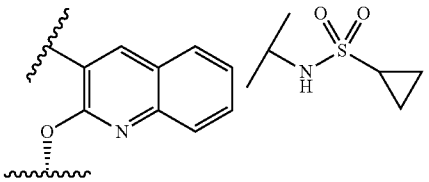 | VI |
| 138. | 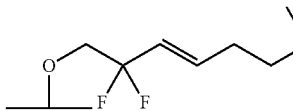 | Absent | 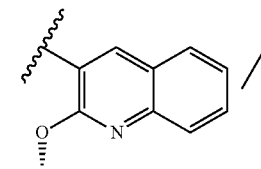 | 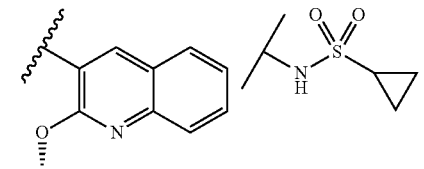 | VII |
| 139. | 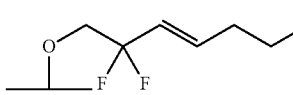 | Absent | 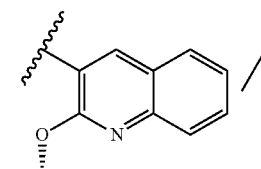 | 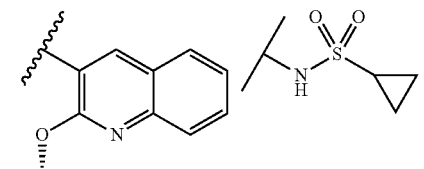 | VI |
| 140. | 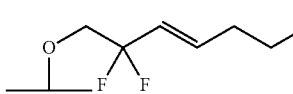 | Absent | 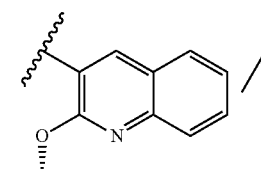 | 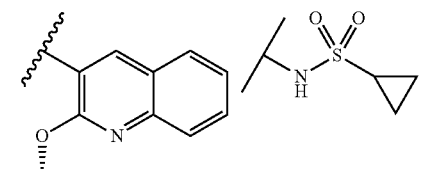 | VII |
| 141. | 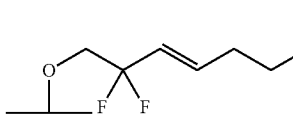 | Absent | 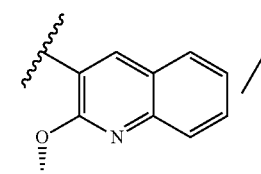 | 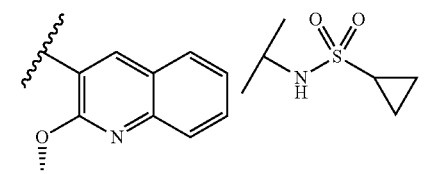 | VI |
| 142. | 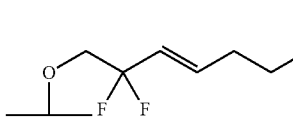 | Absent | 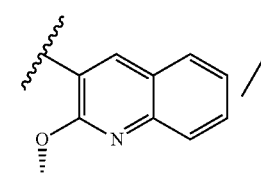 | 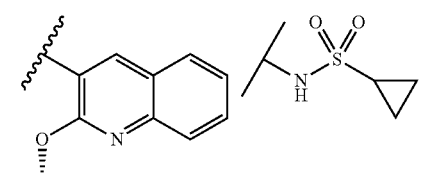 | VII |

TABLE 1-continued

| Example # | M—L | Ar² | Ar¹ | G | Formula |
|---|---|---|---|---|---|
| 143. | | Absent | | | VI |
| 144. | | Absent | | | VII |
| 145. | | | | | VI |
| 146. | | | | | VII |
| 147. | | Absent | | | VI |
| 148. | | Absent | | | VII |
| 149. | | Absent | | | VI |
| 150. | | Absent | | | VII |

TABLE 1-continued
| Example # | M—L | Ar² | Ar¹ | G | Formula |
|---|---|---|---|---|---|
| 151. | 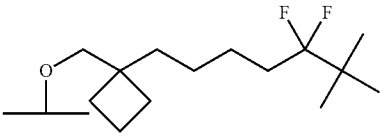 | Absent | 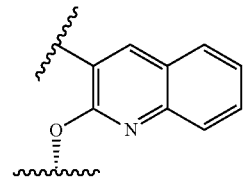 | 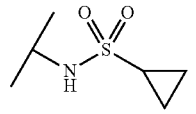 | VI |
| 152. | 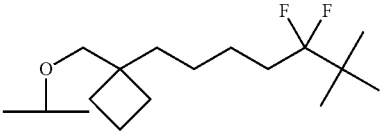 | Absent | 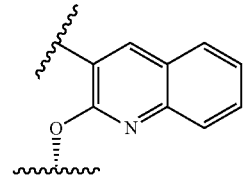 | 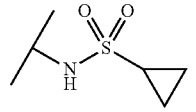 | VII |
| 153. | 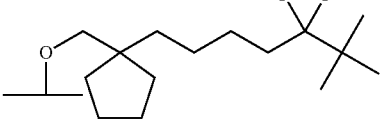 | Absent | 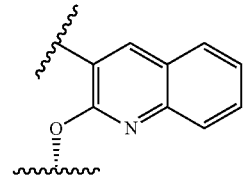 | 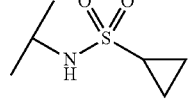 | VI |
| 154. | 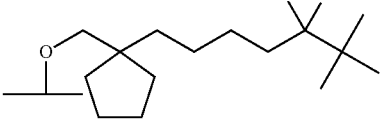 | Absent | 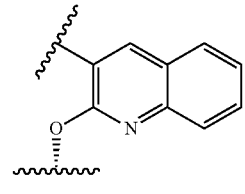 | 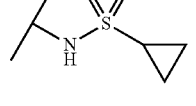 | VII |
| 155. | 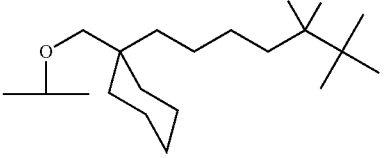 | Absent | 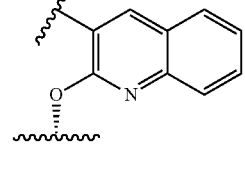 | 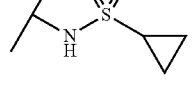 | VI |
| 156. | 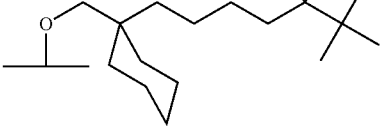 | Absent | 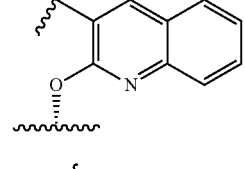 | 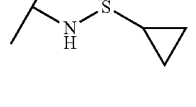 | VII |
| 157. | 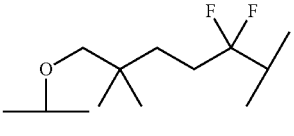 | Absent | 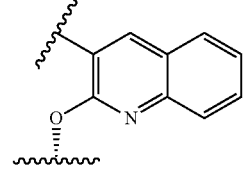 | 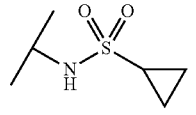 | VI |
| 158. | 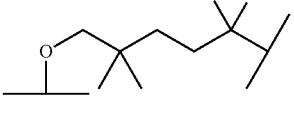 | Absent | 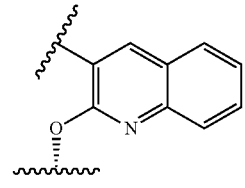 | 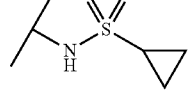 | VII |

TABLE 1-continued

| Example # | M—L | Ar² | Ar¹ | G | Formula |
|---|---|---|---|---|---|
| 159. | (structure) | Absent | (quinoline structure) | (cyclopropylsulfonamide structure) | VI |
| 160. | (structure) | Absent | (quinoline structure) | (cyclopropylsulfonamide structure) | VI |
| 161. | (structure) | Absent | (quinoline structure) | (cyclopropylsulfonamide structure) | VII |
| 162. | (structure) | Absent | (quinoline structure) | (cyclopropylsulfonamide structure) | VI |
| 163. | (structure) | Absent | (quinoline structure) | (cyclopropylsulfonamide structure) | VI |
| 164. | (structure) | Absent | (quinoline structure) | (cyclopropylsulfonamide structure) | VII |
| 165. | (structure) | Absent | (quinoline structure) | (cyclopropylsulfonamide structure) | VI |
| 166. | (structure) | Absent | (quinoline structure) | (cyclopropylsulfonamide structure) | VII |

TABLE 1-continued

| Example # | M—L | Ar² | Ar¹ | G | Formula |
|---|---|---|---|---|---|
| 167. | (structure) | Absent | (quinoline structure) | (cyclopropyl sulfonamide) | VI |
| 168. | (structure) | Absent | (quinoline structure) | (cyclopropyl sulfonamide) | VII |
| 169. | (structure) | Absent | (quinoline structure) | (cyclopropyl sulfonamide) | VI |
| 170. | (structure) | Absent | (quinoline structure) | (cyclopropyl sulfonamide) | VII |
| 171. | (structure) | Absent | (quinoline structure) | (cyclopropyl sulfonamide) | VI |
| 172. | (structure) | Absent | (quinoline structure) | (cyclopropyl sulfonamide) | VII |
| 173. | (structure) | Absent | (quinoline structure) | (cyclopropyl sulfonamide) | VI |
| 174. | (structure) | Absent | (quinoline structure) | (cyclopropyl sulfonamide) | VII |

TABLE 1-continued
| Example # | M—L | Ar² | Ar¹ | G | Formula |
|---|---|---|---|---|---|
| 175. | 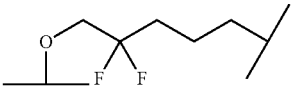 | Absent | 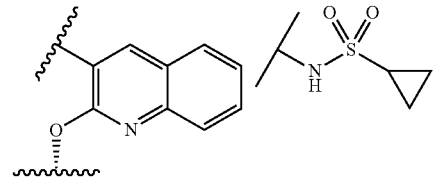 |  | VI |
| 176. | 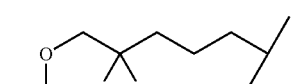 | Absent | 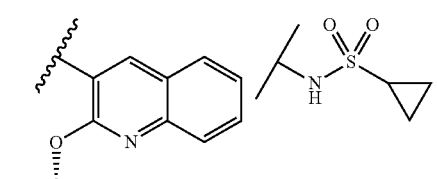 |  | VII |
| 177. | 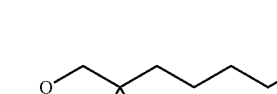 | Absent | 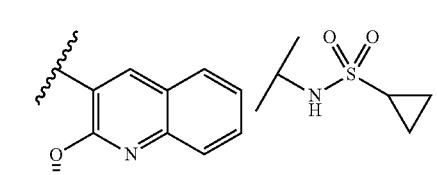 |  | VI |
| 178. | 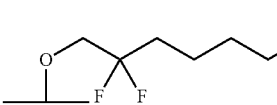 | Absent | 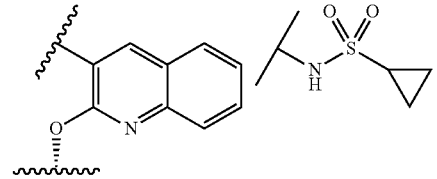 |  | VII |
| 179. | 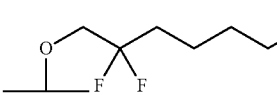 | Absent | 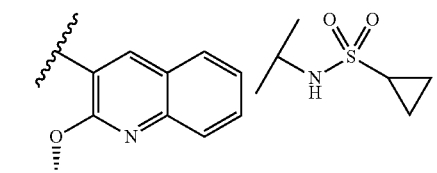 |  | VI |
| 180. | 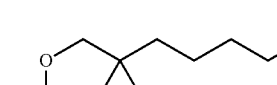 | Absent | 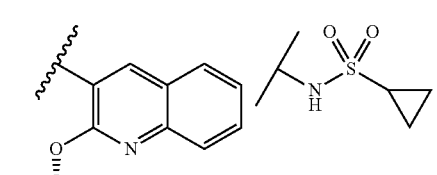 |  | VII |
| 181. | 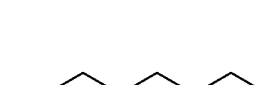 | Absent | 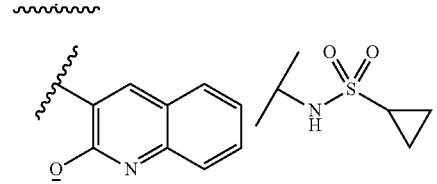 |  | VI |
| 182. | 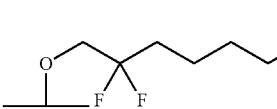 | Absent | 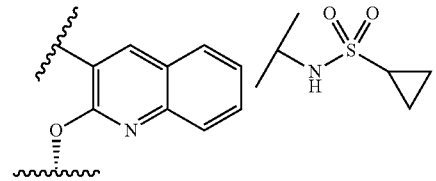 |  | VII |

TABLE 1-continued

| Example # | M—L | Ar² | Ar¹ | G | Formula |
|---|---|---|---|---|---|
| 183. | (structure) | (m-phenylene) | (quinoline) | OH | VI |
| 184. | (structure) | (m-phenylene) | (quinoline) | (cyclopropylsulfonamide) | VI |
| 185. | (structure) | (m-phenylene) | (quinoline) | (cyclopropylsulfonamide) | VII |
| 186. | (structure) | (m-phenylene) | (quinoline) | OH | VI |
| 187. | (structure) | (m-phenylene) | (quinoline) | (cyclopropylsulfonamide) | VI |
| 188. | (structure) | (m-phenylene) | (quinoline) | (cyclopropylsulfonamide) | VII |
| 189. | (structure) | Absent | (quinoline) | OH | VI |
| 190. | (structure) | Absent | (quinoline) | (cyclopropylsulfonamide) | VI |
| 191. | (structure) | Absent | (quinoline) | (cyclopropylsulfonamide) | VII |

TABLE 1-continued
| Example # | M—L | Ar² | Ar¹ | G | Formula |
|---|---|---|---|---|---|
| 192. | 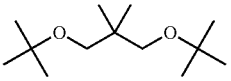 | 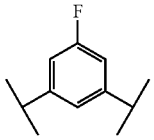 | 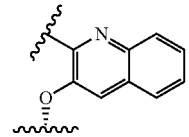 | OH | VI |
| 193. |  | 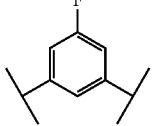 | 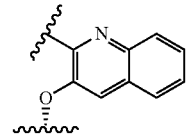 | 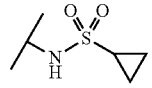 | VI |
| 194. | 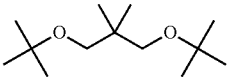 | 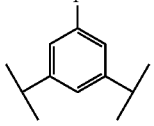 | 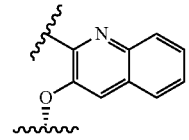 | 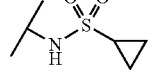 | VII |
| 195. | 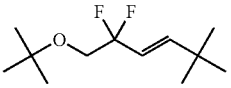 | 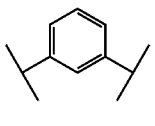 | 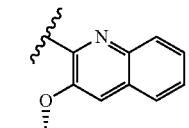 | OH | VI |
| 196. | 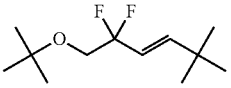 | 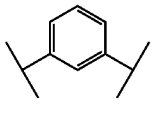 | 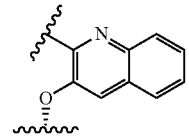 | 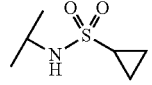 | VI |
| 197. | 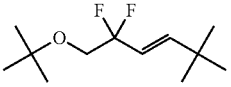 | 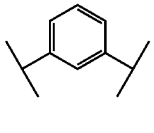 | 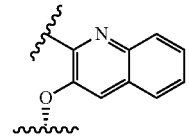 | 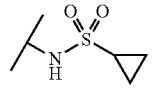 | VII |
| 198. | 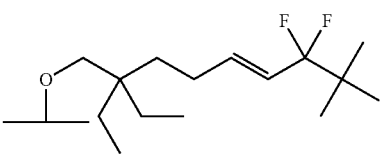 | Absent | 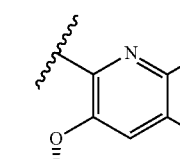 | | VI |
| 199. | 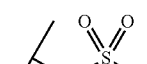 | Absent | 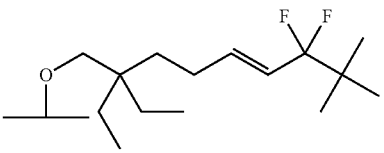 | | VII |
| 200. | 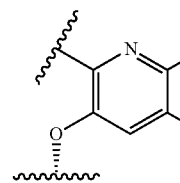 | Absent | 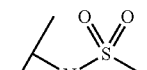 | | VI |

TABLE 1-continued

| Example # | M—L | Ar² | Ar¹ | G | Formula |
|---|---|---|---|---|---|
| 201. | | Absent | | | VII |
| 202. | | Absent | | | VI |
| 203. | | Absent | | | VII |
| 204. | | Absent | | | VI |
| 205. | | Absent | | | VII |
| 206. | | Absent | | | VI |
| 207. | | Absent | | | VII |
| 208. | | Absent | | | VI |

TABLE 1-continued

| Example # | M—L | Ar² | Ar¹ | G | Formula |
|---|---|---|---|---|---|
| 209. | | Absent | | | VII |
| 210. | | Absent | | | VI |
| 211. | | Absent | | | VII |
| 212. | | Absent | | | VI |
| 213. | | Absent | | | VII |
| 214. | | Absent | | | VI |
| 215. | | Absent | | | VII |
| 216. | | Absent | | | VI |

| Example # | M—L | Ar² | Ar¹ | G | Formula |
|---|---|---|---|---|---|
| 217. | (cyclopropyl-CH₂-O- linked to CH₂-CH=CH-C(F)(F)-CH(CH₃)₂) | Absent | quinoline with O-linker | CH(CH₃)-NH-SO₂-cyclopropyl | VII |
| 218. | (cyclobutyl-CH₂-O- linked to CH₂-CH=CH-C(F)(F)-CH(CH₃)₂) | Absent | quinoline with O-linker | CH(CH₃)-NH-SO₂-cyclopropyl | VI |
| 219. | (cyclobutyl-CH₂-O- linked to CH₂-CH=CH-C(F)(F)-CH(CH₃)₂) | Absent | quinoline with O-linker | CH(CH₃)-NH-SO₂-cyclopropyl | VII |
| 220. | (gem-dimethyl-O- linked to (CH₂)₃-CH=CH-C(F)(F)-CH(CH₃)₂) | Absent | quinoline with O-linker | CH(CH₃)-NH-SO₂-cyclopropyl | VI |
| 221. | (gem-dimethyl-O- linked to (CH₂)₃-CH=CH-C(F)(F)-CH(CH₃)₂) | Absent | quinoline with O-linker | CH(CH₃)-NH-SO₂-cyclopropyl | VII |
| 222. | (cyclopropyl-CH₂-O- linked to (CH₂)₃-CH=CH-C(F)(F)-CH(CH₃)₂) | Absent | quinoline with O-linker | CH(CH₃)-NH-SO₂-cyclopropyl | VI |
| 223. | (cyclopropyl-CH₂-O- linked to (CH₂)₃-CH=CH-C(F)(F)-CH(CH₃)₂) | Absent | quinoline with O-linker | CH(CH₃)-NH-SO₂-cyclopropyl | VII |
| 224. | (cyclobutyl-CH₂-O- linked to (CH₂)₃-CH=CH-C(F)(F)-CH(CH₃)₂) | Absent | quinoline with O-linker | CH(CH₃)-NH-SO₂-cyclopropyl | VI |

TABLE 1-continued

| Example # | M—L | Ar² | Ar¹ | G | Formula |
|---|---|---|---|---|---|
| 225. | | Absent | quinoline with O | N-sulfonyl cyclopropyl | VII |
| 226. | | Absent | quinoline with O | N-sulfonyl cyclopropyl | VI |
| 227. | | Absent | quinoline with O | N-sulfonyl cyclopropyl | VII |
| 228. | | Absent | quinoline with O | N-sulfonyl cyclopropyl | VI |
| 229. | | Absent | quinoline with O | N-sulfonyl cyclopropyl | VII |
| 230. | | Absent | quinoline with O | N-sulfonyl cyclopropyl | VI |
| 231. | | Absent | quinoline with O | N-sulfonyl cyclopropyl | VII |
| 232. | | Absent | quinoline with O | N-sulfonyl cyclopropyl | VI |

TABLE 1-continued

| Example # | M—L | Ar² | Ar¹ | G | Formula |
|---|---|---|---|---|---|
| 233. | | Absent | | | VII |
| 234. | | Absent | | | VI |
| 235. | | Absent | | | VII |
| 236. | | | | | VI |
| 237. | | | | | VII |
| 238. | | Absent | | | VI |
| 239. | | Absent | | | VII |
| 240. | | Absent | | | VI |

TABLE 1-continued

| Example # | M—L | Ar² | Ar¹ | G | Formula |
|---|---|---|---|---|---|
| 241. | | Absent | | | VII |
| 242. | | Absent | | | VI |
| 243. | | Absent | | | VII |
| 244. | | Absent | | | VI |
| 245. | | Absent | | | VII |
| 246. | | Absent | | | VI |
| 247. | | Absent | | | VII |
| 248. | | Absent | | | VI |

TABLE 1-continued
| Example # | M—L | Ar² | Ar¹ | G | Formula |
|---|---|---|---|---|---|
| 249. | 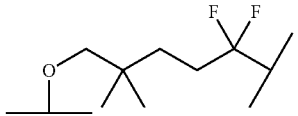 | Absent | 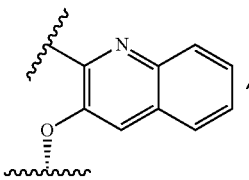 | 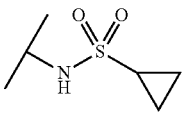 | VII |
| 250. | 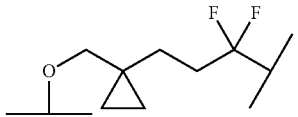 | Absent | 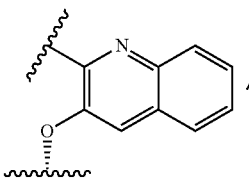 | 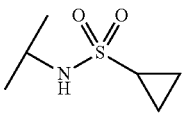 | VI |
| 251. | 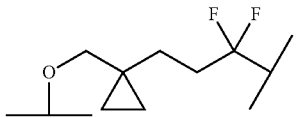 | Absent | 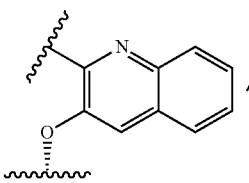 | 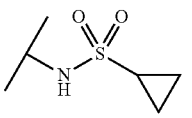 | VII |
| 252. | 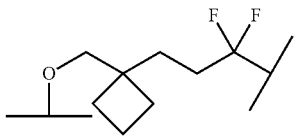 | Absent | 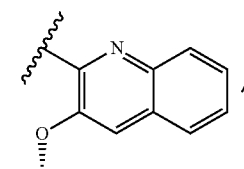 | 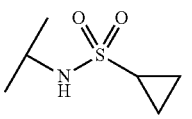 | VI |
| 253. | 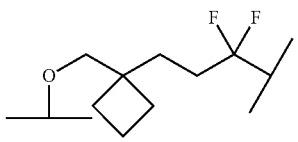 | Absent | 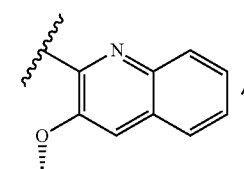 | 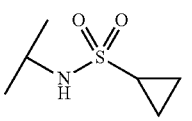 | VII |
| 254. | 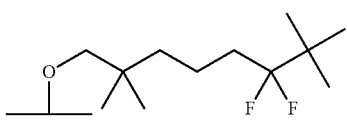 | Absent | 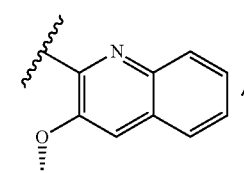 | 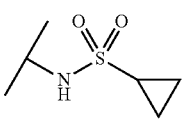 | VI |
| 255. | 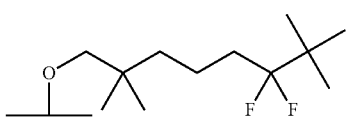 | Absent | 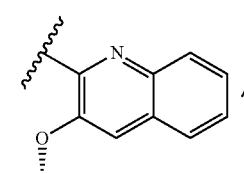 | 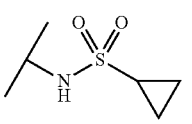 | VII |
| 256. | 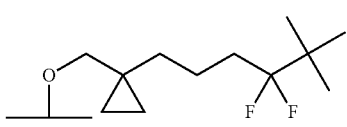 | Absent | 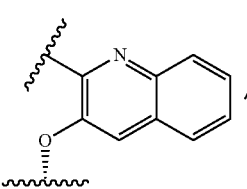 | 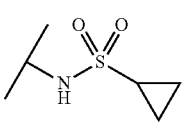 | VI |

TABLE 1-continued
| Example # | M—L | Ar² | Ar¹ | G | Formula |
|---|---|---|---|---|---|
| 257. | 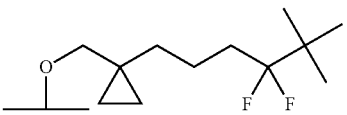 | Absent | 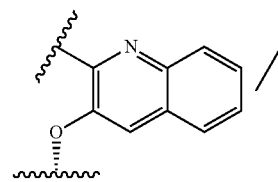 | 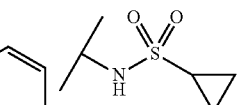 | VII |
| 258. | 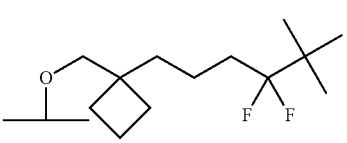 | Absent | 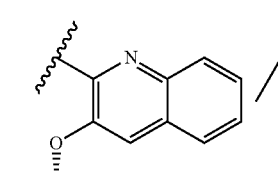 | 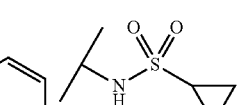 | VI |
| 259. | 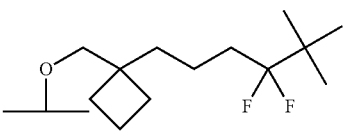 | Absent | 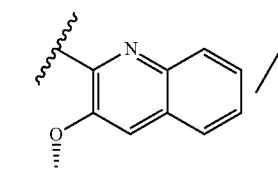 | 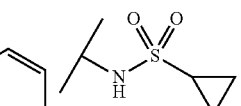 | VII |
| 260. | 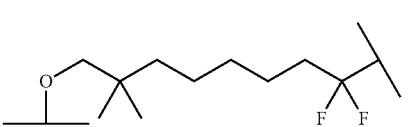 | Absent | 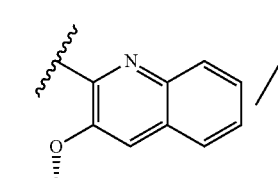 | 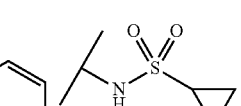 | VI |
| 261. | 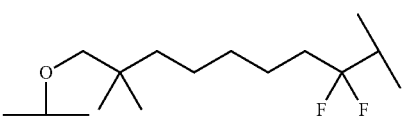 | Absent | 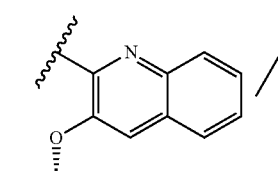 | 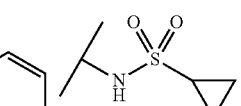 | VII |
| 262. | 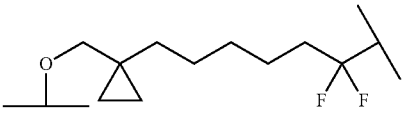 | Absent | 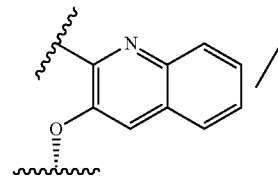 | 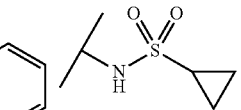 | VI |
| 263. | 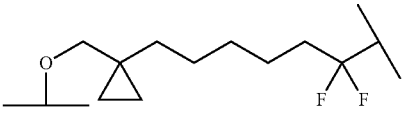 | Absent | 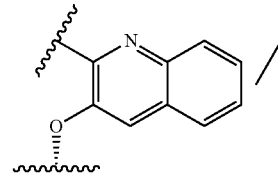 | 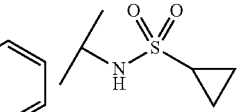 | VII |
| 264. | 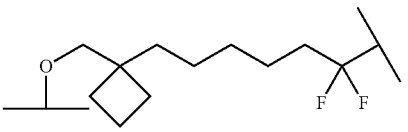 | Absent | 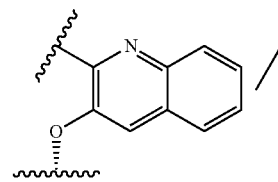 | 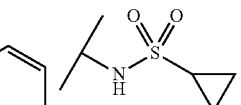 | VI |

TABLE 1-continued

| Example # | M—L | Ar² | Ar¹ | G | Formula |
|---|---|---|---|---|---|
| 265. | | Absent | | | VII |
| 266. | | Absent | | | VI |
| 267. | | Absent | | | VII |
| 268. | | Absent | | | VI |
| 269. | | Absent | | | VII |
| 270. | | Absent | | | VI |
| 271. | | Absent | | | VII |
| 272. | | Absent | | | VI |

TABLE 1-continued
| Example # | M—L | Ar² | Ar¹ | G | Formula |
|---|---|---|---|---|---|
| 273. | 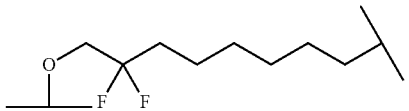 | Absent | 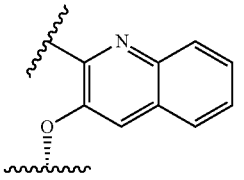 | 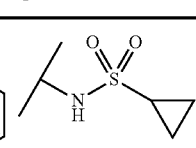 | VII |
| 274. | 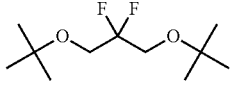 | 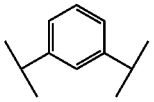 | 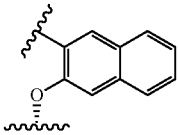 | OH | VI |
| 275. | 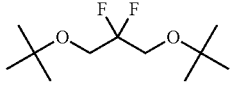 | 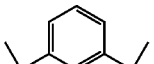 | 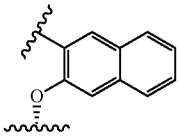 | 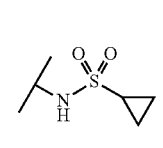 | VI |
| 276. | 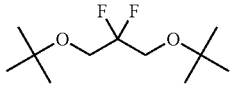 | 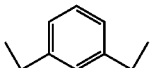 | 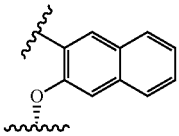 | 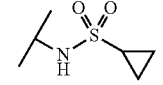 | VII |
| 277. |  | 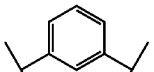 | 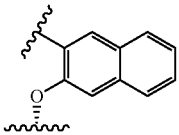 | OH | VI |
| 278. | 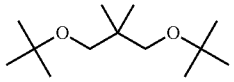 | 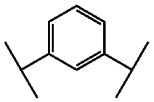 | 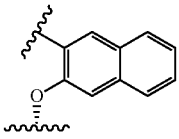 | 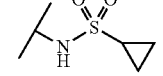 | VI |
| 279. | 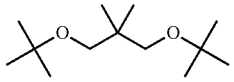 | 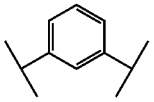 | 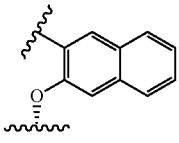 | 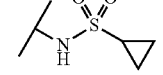 | VII |
| 280. | 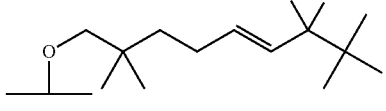 | Absent | 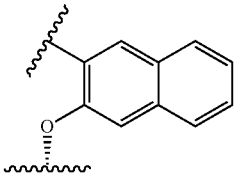 | OH | VI |
| 281. | 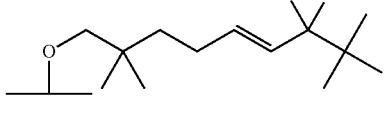 | Absent | 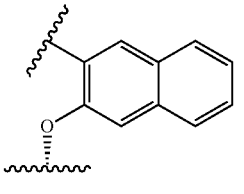 | 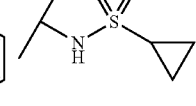 | VI |

TABLE 1-continued

| Example # | M—L | Ar² | Ar¹ | G | Formula |
|---|---|---|---|---|---|
| 282. | (structure) | Absent | naphthalene-O- | -NHSO₂-cyclopropyl | VII |
| 283. | (structure) | 3,5-F-phenyl | naphthalene-O- | OH | VI |
| 284. | (structure) | 3,5-F-phenyl | naphthalene-O- | -NHSO₂-cyclopropyl | VI |
| 285. | (structure) | 3,5-F-phenyl | naphthalene-O- | -NHSO₂-cyclopropyl | VII |
| 286. | (structure) | 1,3-phenyl | naphthalene-O- | OH | VI |
| 287. | (structure) | 1,3-phenyl | naphthalene-O- | -NHSO₂-cyclopropyl | VI |
| 288. | (structure) | 1,3-phenyl | naphthalene-O- | -NHSO₂-cyclopropyl | VII |
| 289. | (structure) | Absent | naphthalene-O- | -NHSO₂-cyclopropyl | VI |
| 290. | (structure) | Absent | naphthalene-O- | -NHSO₂-cyclopropyl | VII |

TABLE 1-continued

| Example # | M—L | Ar² | Ar¹ | G | Formula |
|---|---|---|---|---|---|
| 291. | | Absent | | | VI |
| 292. | | Absent | | | VII |
| 293. | | Absent | | | VI |
| 294. | | Absent | | | VII |
| 295. | | Absent | | | VI |
| 296. | | Absent | | | VII |
| 297. | | Absent | | | VI |
| 298. | | Absent | | | VII |

TABLE 1-continued
| Example # | M—L | Ar² | Ar¹ | G | Formula |
|---|---|---|---|---|---|
| 299. | 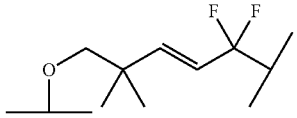 | Absent | 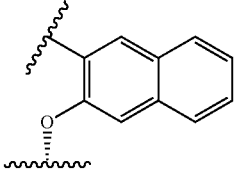 | 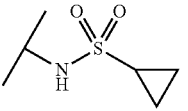 | VI |
| 300. | 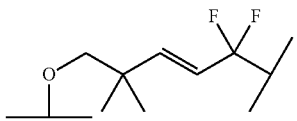 | Absent | 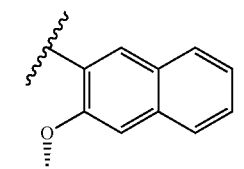 | 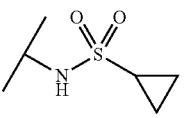 | VII |
| 301. | 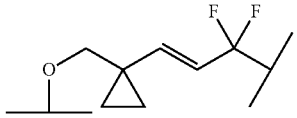 | Absent | 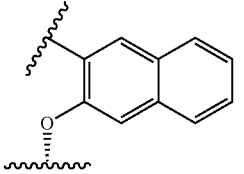 | 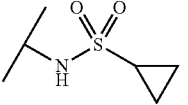 | VI |
| 302. | 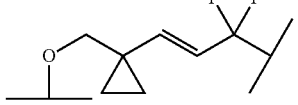 | Absent | 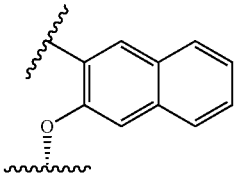 | 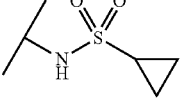 | VII |
| 303. | 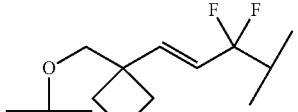 | Absent | 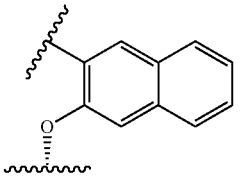 | 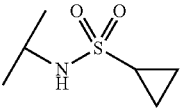 | VI |
| 304. | 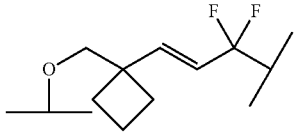 | Absent | 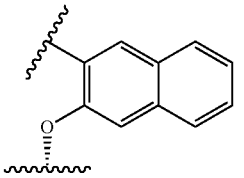 | 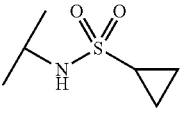 | VII |
| 305. |  | Absent | 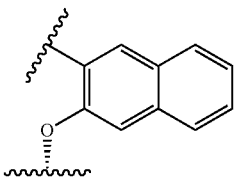 | 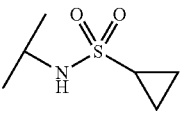 | VI |
| 306. | 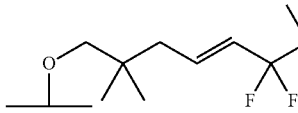 | Absent | 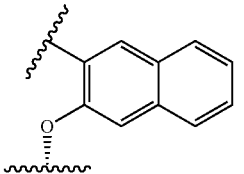 | 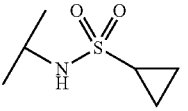 | VII |

TABLE 1-continued
| Example # | M—L | Ar² | Ar¹ | G | Formula |
|---|---|---|---|---|---|
| 307. | 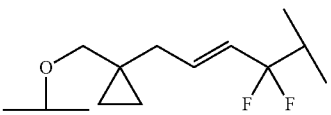 | Absent | 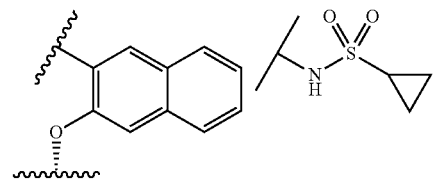 | 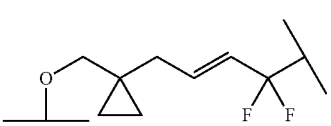 | VI |
| 308. | 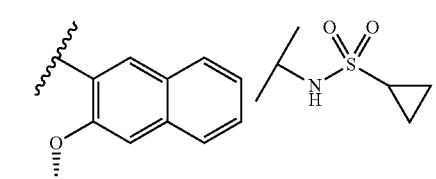 | Absent | 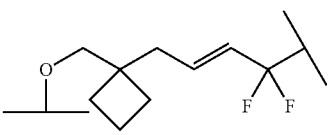 | 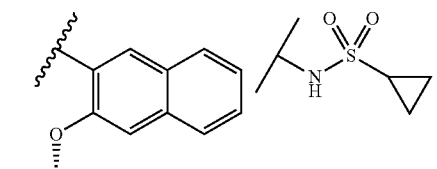 | VII |
| 309. | 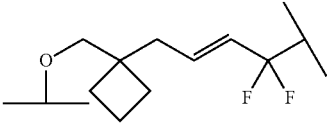 | Absent | 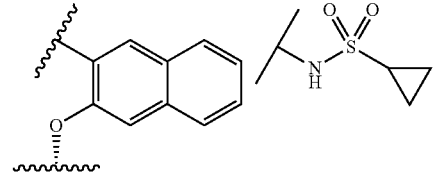 | 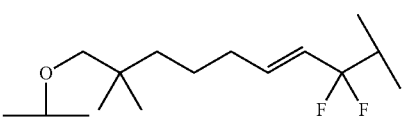 | VI |
| 310. | 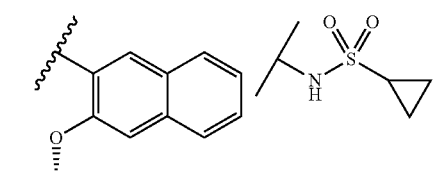 | Absent | 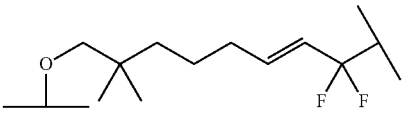 | 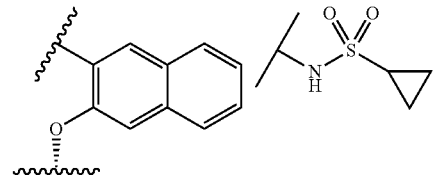 | VII |
| 311. | 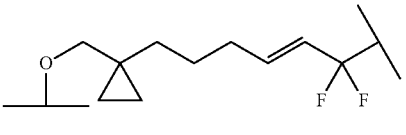 | Absent | 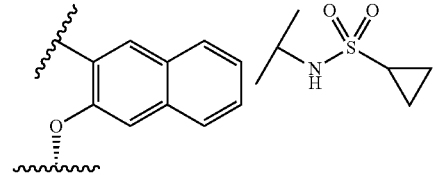 | 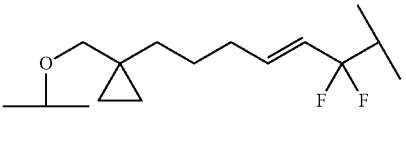 | VI |
| 312. | 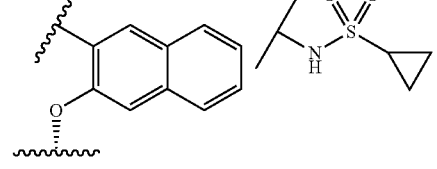 | Absent | | | VII |
| 313. | | Absent | | | VI |
| 314. | | Absent | | | VII |

TABLE 1-continued

| Example # | M—L | Ar² | Ar¹ | G | Formula |
|---|---|---|---|---|---|
| 315. | | Absent | | | VI |
| 316. | | Absent | | | VII |
| 317. | | Absent | | | VI |
| 318. | | Absent | | | VII |
| 319. | | Absent | | | VI |
| 320. | | Absent | | | VII |
| 321. | | Absent | | | VI |
| 322. | | Absent | | | VII |

TABLE 1-continued

| Example # | M—L | Ar² | Ar¹ | G | Formula |
|---|---|---|---|---|---|
| 323. | (structure) | Absent | (naphthalene structure) | (cyclopropyl sulfonamide) | VI |
| 324. | (structure) | Absent | (naphthalene structure) | (cyclopropyl sulfonamide) | VII |
| 325. | (structure) | Absent | (naphthalene structure) | (cyclopropyl sulfonamide) | VI |
| 326. | (structure) | Absent | (naphthalene structure) | (cyclopropyl sulfonamide) | VII |
| 327. | (structure) | (phenyl structure) | (naphthalene structure) | (cyclopropyl sulfonamide) | VI |
| 328. | (structure) | (phenyl structure) | (naphthalene structure) | (cyclopropyl sulfonamide) | VII |
| 329. | (structure) | Absent | (naphthalene structure) | (cyclopropyl sulfonamide) | VI |
| 330. | (structure) | Absent | (naphthalene structure) | (cyclopropyl sulfonamide) | VII |

TABLE 1-continued

| Example # | M—L | Ar² | Ar¹ | G | Formula |
|---|---|---|---|---|---|
| 331. | | Absent | | | VI |
| 332. | | Absent | | | VII |
| 333. | | Absent | | | VI |
| 334. | | Absent | | | VII |
| 335. | | Absent | | | VI |
| 336. | | Absent | | | VII |
| 337. | | Absent | | | VI |
| 338. | | Absent | | | VII |

TABLE 1-continued

| Example # | M—L | Ar² | Ar¹ | G | Formula |
|---|---|---|---|---|---|
| 339. | | Absent | naphthalene-O- | -C(CH₃)H-NH-SO₂-cyclopropyl | VI |
| 340. | | Absent | naphthalene-O- | -C(CH₃)H-NH-SO₂-cyclopropyl | VII |
| 341. | | Absent | naphthalene-O- | -C(CH₃)H-NH-SO₂-cyclopropyl | VI |
| 342. | | Absent | naphthalene-O- | -C(CH₃)H-NH-SO₂-cyclopropyl | VII |
| 343. | | Absent | naphthalene-O- | -C(CH₃)H-NH-SO₂-cyclopropyl | VI |
| 344. | | Absent | naphthalene-O- | -C(CH₃)H-NH-SO₂-cyclopropyl | VII |
| 345. | | Absent | naphthalene-O- | -C(CH₃)H-NH-SO₂-cyclopropyl | VI |
| 346. | | Absent | naphthalene-O- | -C(CH₃)H-NH-SO₂-cyclopropyl | VII |

TABLE 1-continued

| Example # | M—L | Ar² | Ar¹ | G | Formula |
|---|---|---|---|---|---|
| 347. | | Absent | | | VI |
| 348. | | Absent | | | VII |
| 349. | | Absent | | | VI |
| 350. | | Absent | | | VII |
| 351. | | Absent | | | VI |
| 352. | | Absent | | | VII |
| 353. | | Absent | | | VI |
| 354. | | Absent | | | VII |

TABLE 1-continued

| Example # | M—L | Ar² | Ar¹ | G | Formula |
|---|---|---|---|---|---|
| 355. | (oxetane-cyclobutyl chain with CF₂ and gem-dimethyl) | Absent | naphthalene with O linker | cyclopropylsulfonamide with methyl | VI |
| 356. | (oxetane-cyclobutyl chain with CF₂ and gem-dimethyl) | Absent | naphthalene with O linker | cyclopropylsulfonamide with methyl | VII |
| 357. | (oxetane chain with CF₂ and gem-dimethyl) | Absent | naphthalene with O linker | cyclopropylsulfonamide with methyl | VI |
| 358. | (oxetane chain with CF₂ and gem-dimethyl) | Absent | naphthalene with O linker | cyclopropylsulfonamide with methyl | VII |
| 359. | (oxetane chain with CF₂ and gem-dimethyl) | Absent | naphthalene with O linker | cyclopropylsulfonamide with methyl | VI |
| 360. | (oxetane chain with CF₂ and gem-dimethyl) | Absent | naphthalene with O linker | cyclopropylsulfonamide with methyl | VII |
| 361. | (oxetane chain with CF₂ and gem-dimethyl) | Absent | naphthalene with O linker | cyclopropylsulfonamide with methyl | VI |
| 362. | (oxetane chain with CF₂ and gem-dimethyl) | Absent | naphthalene with O linker | cyclopropylsulfonamide with methyl | VII |

TABLE 1-continued
| Example # | M—L | Ar² | Ar¹ | G | Formula |
|---|---|---|---|---|---|
| 363. | 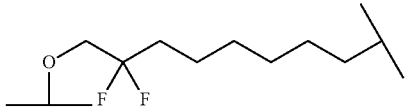 | Absent | 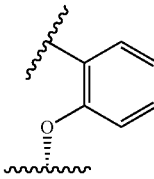 | 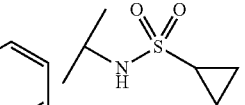 | VI |
| 364. | 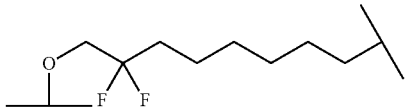 | Absent | 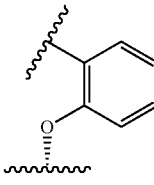 | 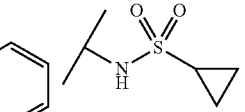 | VII |
| 365. | 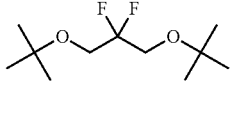 | 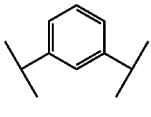 | 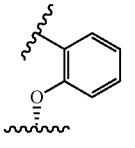 | OH | VI |
| 366. | 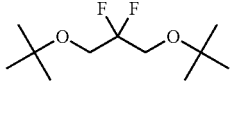 | 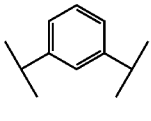 | 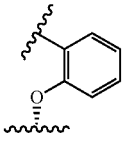 | 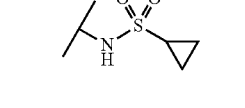 | VI |
| 367. | 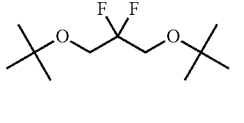 | 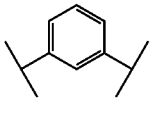 | 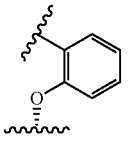 | 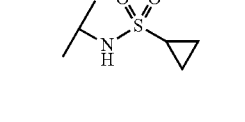 | VII |
| 368. | 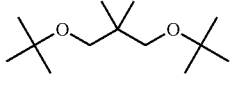 | 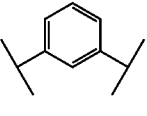 | 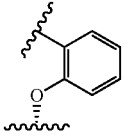 | OH | VI |
| 369. | 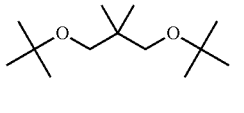 | 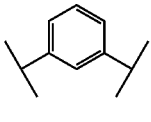 | 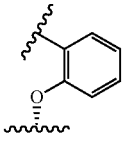 | 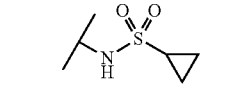 | VI |
| 370. | 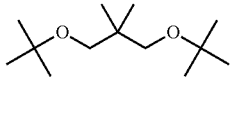 | 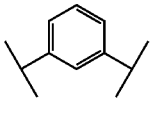 | 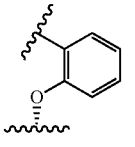 | 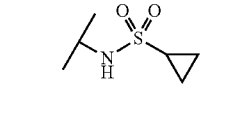 | VII |
| 371. | 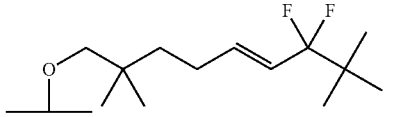 | Absent | 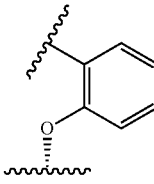 | OH | VI |

TABLE 1-continued

| Example # | M—L | Ar² | Ar¹ | G | Formula |
|---|---|---|---|---|---|
| 372. | | Absent | | | VI |
| 373. | | Absent | | | VII |
| 374. | | | | OH | VI |
| 375. | | | | | VI |
| 376. | | | | | VII |
| 377. | | | | OH | VI |
| 378. | | | | | VI |
| 379. | | | | | VII |
| 380. | | Absent | | | VI |

TABLE 1-continued

| Example # | M—L | Ar² | Ar¹ | G | Formula |
|---|---|---|---|---|---|
| 381. | | Absent | | | VII |
| 382. | | Absent | | | VI |
| 383. | | Absent | | | VII |
| 384. | | Absent | | | VI |
| 385. | | Absent | | | VII |
| 386. | | Absent | | | VI |
| 387. | | Absent | | | VII |
| 388. | | Absent | | | VI |

TABLE 1-continued

| Example # | M—L | Ar² | Ar¹ | G | Formula |
|---|---|---|---|---|---|
| 389. | (structure) | Absent | (structure) | (structure) | VII |
| 390. | (structure) | Absent | (structure) | (structure) | VI |
| 391. | (structure) | Absent | (structure) | (structure) | VII |
| 392. | (structure) | Absent | (structure) | (structure) | VI |
| 393. | (structure) | Absent | (structure) | (structure) | VII |
| 394. | (structure) | Absent | (structure) | (structure) | VI |
| 395. | (structure) | Absent | (structure) | (structure) | VII |
| 396. | (structure) | Absent | (structure) | (structure) | VI |

TABLE 1-continued

| Example # | M—L | Ar² | Ar¹ | G | Formula |
|---|---|---|---|---|---|
| 397. | (structure) | Absent | (structure) | (structure) | VII |
| 398. | (structure) | Absent | (structure) | (structure) | VI |
| 399. | (structure) | Absent | (structure) | (structure) | VII |
| 400. | (structure) | Absent | (structure) | (structure) | VI |
| 401. | (structure) | Absent | (structure) | (structure) | VII |
| 402. | (structure) | Absent | (structure) | (structure) | VI |
| 403. | (structure) | Absent | (structure) | (structure) | VII |
| 404. | (structure) | Absent | (structure) | (structure) | VI |

TABLE 1-continued

| Example # | M—L | Ar² | Ar¹ | G | Formula |
|---|---|---|---|---|---|
| 405. | | Absent | | | VII |
| 406. | | Absent | | | VI |
| 407. | | Absent | | | VII |
| 408. | | Absent | | | VI |
| 409. | | Absent | | | VII |
| 410. | | Absent | | | VI |
| 411. | | Absent | | | VII |
| 412. | | Absent | | | VI |

TABLE 1-continued
| Example # | M—L | Ar² | Ar¹ | G | Formula |
|---|---|---|---|---|---|
| 413. | 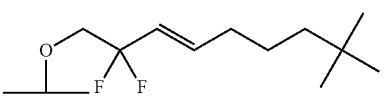 | Absent | 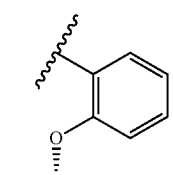 | 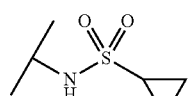 | VII |
| 414. | 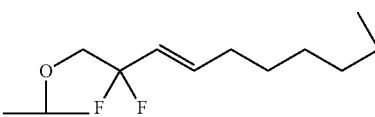 | Absent | 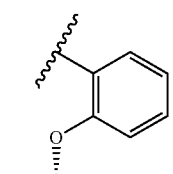 | 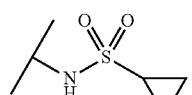 | VI |
| 415. | 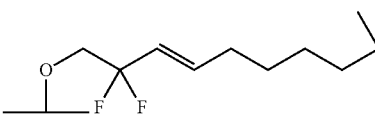 | Absent | 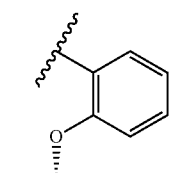 | 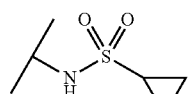 | VII |
| 416. | 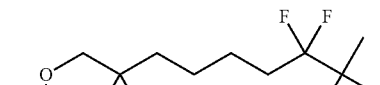 | Absent | 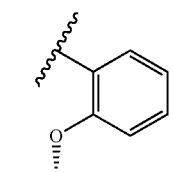 | 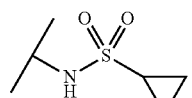 | VI |
| 417. | 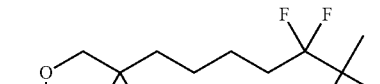 | Absent | 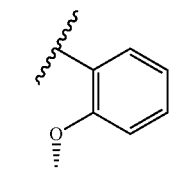 | 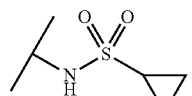 | VII |
| 418. |  | 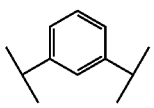 | 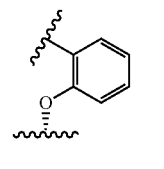 | 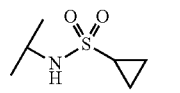 | VI |
| 419. |  | 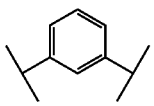 | 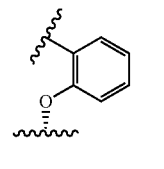 | 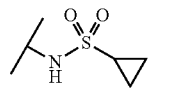 | VII |
| 420. | 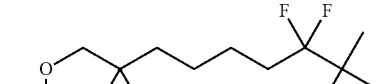 | Absent | 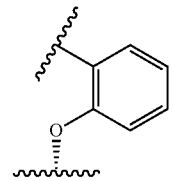 | 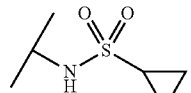 | VI |

TABLE 1-continued

| Example # | M—L | Ar² | Ar¹ | G | Formula |
|---|---|---|---|---|---|
| 421. | | Absent | | | VII |
| 422. | | Absent | | | VI |
| 423. | | Absent | | | VII |
| 424. | | Absent | | | VI |
| 425. | | Absent | | | VII |
| 426. | | Absent | | | VI |
| 427. | | Absent | | | VII |
| 428. | | Absent | | | VI |

TABLE 1-continued

| Example # | M—L | Ar² | Ar¹ | G | Formula |
|---|---|---|---|---|---|
| 429. | | Absent | | | VII |
| 430. | | Absent | | | VI |
| 431. | | Absent | | | VII |
| 432. | | Absent | | | VI |
| 433. | | Absent | | | VII |
| 434. | | Absent | | | VI |
| 435. | | Absent | | | VII |
| 436. | | Absent | | | VI |

TABLE 1-continued
| Example # | M—L | Ar² | Ar¹ | G | Formula |
|---|---|---|---|---|---|
| 437. | 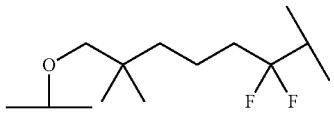 | Absent | 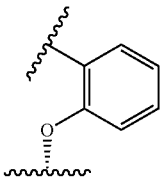 | 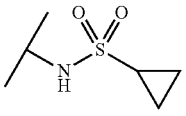 | VII |
| 438. | 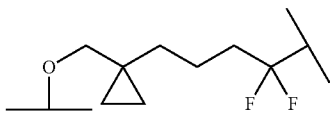 | Absent | 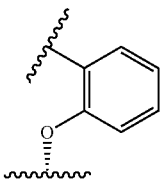 | 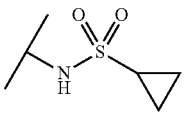 | VI |
| 439. | 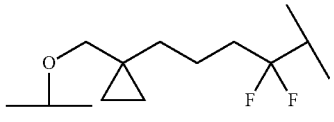 | Absent | 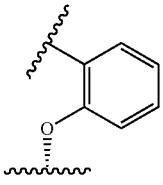 | 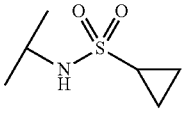 | VII |
| 440. | 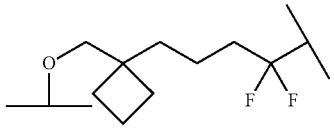 | Absent | 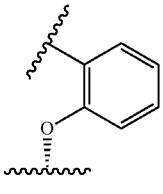 | 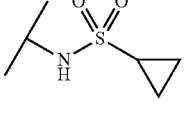 | VI |
| 441. | 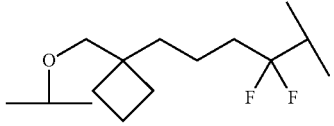 | Absent | 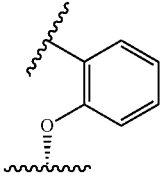 | 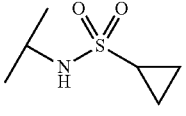 | VII |
| 442. | 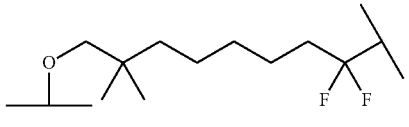 | Absent | 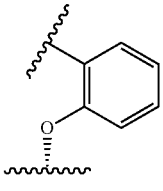 | 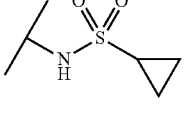 | VI |
| 443. | 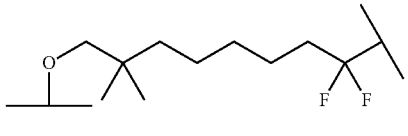 | Absent | 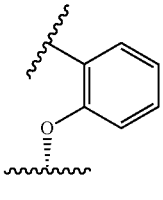 | 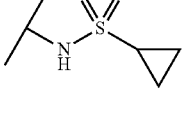 | VII |
| 444. | 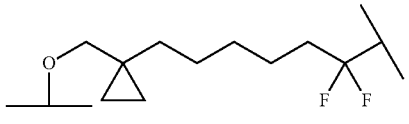 | Absent | 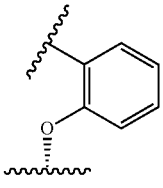 | 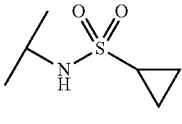 | VI |

TABLE 1-continued

| Example # | M—L | Ar² | Ar¹ | G | Formula |
|---|---|---|---|---|---|
| 445. | (structure: oxetane-CH₂-C(cyclopropyl)-(CH₂)₅-CF₂-C(CH₃)₂-) | Absent | phenyl with O-linker | cyclopropanesulfonamide | VII |
| 446. | (structure: oxetane-CH₂-C(cyclobutyl)-(CH₂)₅-CF₂-C(CH₃)₂-) | Absent | phenyl with O-linker | cyclopropanesulfonamide | VI |
| 447. | (structure: oxetane-CH₂-C(cyclobutyl)-(CH₂)₅-CF₂-C(CH₃)₂-) | Absent | phenyl with O-linker | cyclopropanesulfonamide | VII |
| 448. | (structure: oxetane-CH₂-CF₂-(CH₂)₃-CH(CH₃)-) | Absent | phenyl with O-linker | cyclopropanesulfonamide | VI |
| 449. | (structure: oxetane-CH₂-CF₂-(CH₂)₃-CH(CH₃)-) | Absent | phenyl with O-linker | cyclopropanesulfonamide | VII |
| 450. | (structure: oxetane-CH₂-CF₂-(CH₂)₄-CH(CH₃)-) | Absent | phenyl with O-linker | cyclopropanesulfonamide | VI |
| 451. | (structure: oxetane-CH₂-CF₂-(CH₂)₄-CH(CH₃)-) | Absent | phenyl with O-linker | cyclopropanesulfonamide | VII |
| 452. | (structure: oxetane-CH₂-CF₂-(CH₂)₄-C(CH₃)₂-) | Absent | phenyl with O-linker | cyclopropanesulfonamide | VI |

TABLE 1-continued

| Example # | M—L | Ar² | Ar¹ | G | Formula |
|---|---|---|---|---|---|
| 453. | 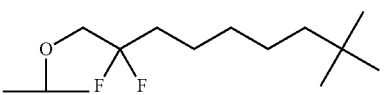 | Absent | 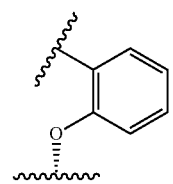 | 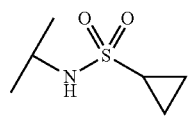 | VII |
| 454. | 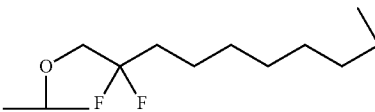 | Absent | 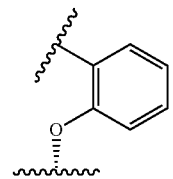 | 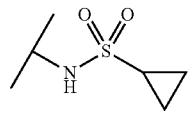 | VI |
| 455. | 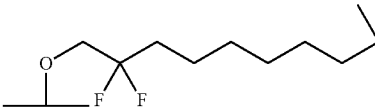 | Absent | 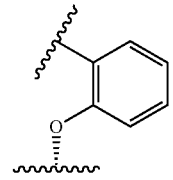 | 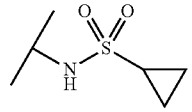 | VII |

The present invention also features pharmaceutical compositions comprising a compound of the present invention, or a pharmaceutically acceptable salt, ester or prodrug thereof and a pharmaceutically acceptable carrier or excipient.

Compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), or antiviral compounds that inhibit host cellular functions such as inosine monophosphate dehydrogenase (for example, ribavirin and the like). Also included are cytokines that modulate immune function. Also included are vaccines comprising HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO 01/90121(A2), or U.S. Pat. No. 6,348,587B1 or WO 01/60315 or WO 01/32153 or non-nucleoside inhibitors such as, for example, benzimidazole polymerase inhibitors described in EP 1162196A1 or WO 02/04425 or inhibitors of HCV protease such as, for example, peptidomimetic type inhibitors such as BILN2061 and the like or inhibitors of HCV helicase.

Other agents to be administered in combination with a compound of the present invention include any agent or combination of agents that inhibit the replication of other viruses for co-infected individuals. These agent include but are not limited to therapies for disease caused by hepatitis B (HBV) infection such as, for example, adefovir, lamivudine, and tenofovir or therapies for disease caused by human immunodeficiency virus (HIV) infection such as, for example, protease inhibitors: ritonavir, lopinavir, indinavir, nelfinavir, saquinavir, amprenavir, atazanavir, tipranavir, TMC-114, fosamprenavir; reverse transcriptase inhibitors: zidovudine, lamivudine, didanosine, stavudine, tenofovir, zalcitabine, abacavir, efavirenz, nevirapine, delavirdine, TMC-125; integrase inhibitors: L-870812, S-1360, or entry inhibitors: enfuvirtide (T-20), T-1249.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of the invention, or a pharmaceutically acceptable salt, stereoisomer, tautomer, prodrug, salt of a prodrug, or combination thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

Further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the invention, or a pharmaceutically acceptable salt, stereoisomer, tautomer, prodrug, salt of a prodrug, or combination thereof. Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the invention, or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenofovir, or any combination thereof. Example of the RNA-containing virus includes, but not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the invention, or a pharmaceutically acceptable salt, stereoisomer, tautomer, prodrug, salt of a prodrug, or combination thereof. The agent that treats patients for disease caused by human immunodeficiency virus (HIV) infection may include, but is not limited thereto, ritonavir, lopinavir, indinavir, nelfmavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. Example of the RNA-containing virus includes, but not limited to, hepatitis C virus (HCV). In addition, the present invention provides the use of a compound or a combination of compounds of the invention, or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined herein above, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amount of the compound or combination of compounds of interest, or their pharmaceutically acceptable salt form, prodrugs, or salts of the prodrug, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO03/099274, WO 03/099316, WO 2004/032827, WO 2004/043339, WO 2004/094452, WO 2005/

046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to another embodiment, the pharmaceutical compositions of the present invention may further comprise another anti-viral, anti-bacterial, anti-fungal or anti-cancer agent, or an immune modulator, or another therapeutic agent.

According to still another embodiment, the present invention includes methods of treating viral infection such as, but not limited to, hepatitis C infections in a subject in need of such treatment by administering to said subject an effective amount of a compound of the present invention or a pharmaceutically acceptable salt, ester, or prodrug thereof.

According to a further embodiment, the present invention includes methods of treating hepatitis C infections in a subject in need of such treatment by administering to said subject an anti-HCV virally effective amount or an inhibitory amount of a pharmaceutical composition of the present invention.

An additional embodiment of the present invention includes methods of treating biological samples by contacting the biological samples with the compounds of the present invention.

Yet a further aspect of the present invention is a process of making any of the compounds delineated herein employing any of the synthetic means delineated herein.

The cytochrome P450 monooxygenase inhibitor used in this invention is expected to inhibit metabolism of the compounds of the invention. Therefore, the cytochrome P450 monooxygenase inhibitor would be in an amount effective to inhibit metabolism of the protease inhibitor. Accordingly, the CYP inhibitor is administered in an amount such that the bioavailiablity of the protease inhibitor is increased in comparison to the bioavailability in the absence of the CYP inhibitor.

In one embodiment, the invention provides methods for improving the pharmacokinetics of compounds of the invention. The advantages of improving the pharmacokinetics of drugs are recognized in the art (US 2004/0091527; US 2004/0152625; US 2004/0091527). Accordingly, one embodiment of this invention provides a method for administering an inhibitor of CYP3A4 and a compound of the invention. Another embodiment of this invention provides a method for administering a compound of the invention and an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1"). In a preferred embodiment, the CYP inhibitor preferably inhibits CYP3A4. Any CYP inhibitor that improves the pharmacokinetics of the relevant NS3/4A protease may be used in a method of this invention. These CYP inhibitors include, but are not limited to, ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole.

It will be understood that the administration of the combination of the invention by means of a single patient pack, or patient packs of each formulation, containing within a package insert instructing the patient to the correct use of the invention is a desirable additional feature of this invention.

According to a further aspect of the invention is a pack comprising at least a compound of the invention and a CYP inhibitor of the invention and an information insert containing directions on the use of the combination of the invention. In an alternative embodiment of this invention, the pharmaceutical pack further comprises one or more of additional agent as described herein. The additional agent or agents may be provided in the same pack or in separate packs.

Another aspect of this invention is a packaged kit for a patient to use in the treatment of HCV infection or in the prevention of HCV infection, comprising: a single or a plurality of pharmaceutical formulation of each pharmaceutical component; a container housing the pharmaceutical formulation (s) during storage and prior to administration; and instructions for carrying out drug administration in a manner effective to treat or prevent HCV infection.

Accordingly, this invention provides kits for the simultaneous or sequential administration of a NS3/4A protease inhibitor of the invention and a CYP inhibitor (and optionally an additional agent) or derivatives thereof are prepared in a conventional manner. Typically, such a kit will comprise, e.g. a composition of each inhibitor and optionally the additional agent (s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

DEFINITIONS

Listed below are definitions of various terms used to describe this invention. These definitions apply to the terms as they are used throughout this specification and claims, unless otherwise limited in specific instances, either individually or as part of a larger group.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

The term "anti-cancer agent" refers to a compound or drug capable of preventing or inhibiting the advancement of cancer. Examples of such agents include cis-platin, actinomycin D, doxorubicin, vincristine, vinblastine, etoposide, amsacrine, mitoxantrone, tenipaside, taxol, colchicine, cyclosporin A, phenothiazines or thioxantheres.

The term "anti-fungal agent" shall used to describe a compound which may be used to treat a fungus infection other than 3-AP, 3-AMP or prodrugs of 3-AP and 3-AMP according to the present invention. Anti-fungal agents according to the present invention include, for example, terbinafine, fluconazole, itraconazole, posaconazole, clotrimazole, griseofulvin, nystatin, tolnaftate, caspofungin, amphotericin B, liposomal amphotericin B, and amphotericin B lipid complex.

The term "antibacterial agent" refers to both naturally occurring antibiotics produced by microorganisms to suppress the growth of other microorganisms, and agents synthesized or modified in the laboratory which have either bactericidal or bacteriostatic activity, e.g., β-lactam antibacterial agents, glycopeptides, macrolides, quinolones, tetracyclines, and aminoglycosides. In general, if an antibacterial agent is bacteriostatic, it means that the agent essentially stops bacterial cell growth (but does not kill the bacteria); if the agent is bacteriocidal, it means that the agent kills the bacterial cells (and may stop growth before killing the bacteria).

The term "immune modulator" refers to any substance meant to alter the working of the humoral or cellular immune system of a subject. Such immune modulators include inhibitors of mast cell-mediated inflammation, interferons, interleukins, prostaglandins, steroids, cortico-steroids, colony-stimulating factors, chemotactic factors, etc.

The term "$C_1$-$C_6$ alkyl," or "$C_1$-$C_8$ alkyl," as used herein, refer to saturated, straight- or branched-chain hydrocarbon radicals containing between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "$C_2$-$C_6$ alkenyl," or "$C_2$-$C_8$ alkenyl," as used herein, denote a group derived from a hydrocarbon moiety, wherein the hydrocarbon moiety has at least one carbon-carbon double bond and contains from two to six or two to eight carbon atoms, respectively. Alkenyl groups include, but are not limited to, for example, ethenyl, propenyl, butenyl, 1-methyl-2-buten-1-yl, heptenyl, octenyl and the like.

The term "$C_2$-$C_6$ alkynyl," or "$C_2$-$C_8$ alkynyl," as used herein, denote a group derived from a hydrocarbon moiety, wherein the hydrocarbon moiety has at least one carbon-carbon triple bond and contains from two to six or two to eight carbon atoms, respectively. Representative alkynyl groups include, but are not limited to, for example, ethynyl, 1-propynyl, 1-butynyl, heptynyl, octynyl and the like.

The term "$C_3$-$C_8$-cycloalkyl", or "$C_3$-$C_{12}$-cycloalkyl," as used herein, denotes a group derived from a monocyclic or polycyclic saturated carbocyclic ring, where the saturated carbocyclic ring compound has from 3 to 8, or from 3 to 12, ring atoms, respectively. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_8$-cycloalkenyl", or "$C_3$-$C_{12}$-cycloalkenyl" as used herein, denote a group derived from a monocyclic or polycyclic carbocyclic ring compound having at least one carbon-carbon double, where the carbocyclic ring compound has from 3 to 8, or from 3 to 12, ring atoms, respectively. Examples of $C_3$-$C_8$-cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or two aromatic rings including, but not limited to, phenyl, naphthyl, tetrahydronaphthyl, indanyl, indenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue attached to a heteroaryl ring. Examples include, but are not limited to, pyridinylmethyl, pyrimidinylethyl and the like.

The term "substituted" as used herein, refers to independent replacement of one, two, or three or more of the hydrogen atoms thereon with substituents including, but not limited to, —F, —Cl, —Br, —I, —OH, protected hydroxyl, —NO$_2$, —CN, —NH$_2$, N$_3$, protected amino, alkoxy, thioalkoxy, oxo, -halo-$C_1$-$C_{12}$-alkyl, -halo-$C_2$-$C_{12}$-alkenyl, -halo-$C_2$-$C_{12}$- alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —$COO_2$—$C_1$-$C_{12}$-alkyl, —$COO_2$—$C_2$-$C_{12}$-alkenyl, —$COO_2$—$C_2$-$C_{12}$-alkynyl, —$OCO_2$—$C_3$-$C_{12}$-cycloalkyl, —$OCO_2$-aryl, —$OCO_2$-heteroaryl, —$COO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH— aryl, —OCONH— heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$— aryl, —$NHCO_2$— heteroaryl, —$NHCO_2$— heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2NH$—$C_1$-$C_{12}$-alkyl, —$SO_2NH$—$C_2$-$C_{12}$-alkenyl, —$SO_2NH$—$C_1$-$C_{12}$-alkynyl, —$SO_2NH$—$C_3$-$C_{12}$-cycloalkyl, —$SO_2NH$—aryl, —$SO_2NH$— heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —$NO_2$, —CN, or —$NH_2$. When there is at least two replacements of the hydrogen atoms with substituents, the two substitutents can be taken together to form a cycloalkyl, cycloalkenyl or heterocyclic ring.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a group derived from a monocyclic or polycyclic saturated carbocyclic ring compound. Examples include, but are not limited to, cyclopropyl, cyclobutyl, cyclopentyl, cyclohexyl, bicyclo [2.2.1]heptyl, and bicyclo[2.2.2]octyl. Such alicyclic groups may be further substituted.

The term "heterocycloalkyl" and "heterocyclic" can be used interchangeably and refer to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (v) any of the above rings may be fused to a benzene ring, and (vi) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycoaklylene, cycloalkenylene, cycloalkynylene, arylalkylene, hetoerarylalkylene and heterocycloalkylene groups are to be included in the above definitions, and are applicable to provide the formulas herein with proper valency.

The term "hydroxyl activating group", as used herein, refers to a labile chemical moiety which is known in the art to activate a hydroxyl group so that it will depart during synthetic procedures such as in a substitution or elimination reactions. Examples of hydroxyl activating group include, but not limited to, mesylate, tosylate, triflate, p-nitrobenzoate, phosphonate and the like.

The term "activated hydroxyl", as used herein, refers to a hydroxyl group activated with a hydroxyl activating group, as defined above, including mesylate, tosylate, triflate, p-nitrobenzoate, phosphonate groups, for example.

The term "protected hydroxyl," as used herein, refers to a hydroxyl group protected with a hydroxyl protecting group, as defined above, including benzoyl, acetyl, trimethylsilyl, triethylsilyl, methoxymethyl groups.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

The term "hydroxyl protecting group," as used herein, refers to a labile chemical moiety which is known in the art to protect a hydroxyl group against undesired reactions during synthetic procedures. After said synthetic procedure(s) the hydroxyl protecting group as described herein may be selectively removed. Hydroxyl protecting groups as known in the are described generally in T. H. Greene and P. G., S. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$). Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobronic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development," Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, mean a sufficient amount of the compound so as to decrease the viral load in a biological sample or in a subject (e.g., resulting in at least 10%, preferably at least 50%, more preferably at least 80%, and most preferably at least 90% or 95%, reduction in viral load). As well understood in the medical arts, an anti-hepatitis C virally effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject (e.g., resulting in at least 10%, preferably at least 50%, more preferably at least 80%, and most preferably at least 90% or 95%, reduction in viral load). It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Unless otherwise defined, all technical and scientific terms used herein are accorded the meaning commonly known to one with ordinary skill in the art. All publications, patents, published patent applications, and other references mentioned herein are hereby incorporated by reference in their entirety.

ABBREVIATIONS

Abbreviations which have been used in the descriptions of the schemes and the examples that follow are:

ACN for acetonitrile;

BME for 2-mercaptoethanol;

BOP for benzotriazol-1-yloxy-tris(dimethylamino)phosphonium hexafluorophosphate;

COD for cyclooctadiene;

DAST for diethylaminosulfur trifluoride;

DABCYL for 6-(N-4'-carboxy-4-(dimethylamino)azobenzene)-aminohexyl-1-O-(2-cyanoethyl)-(N,N-diisopropyl)-phosphoramidite;

DCM for dichloromethane;

DIAD for diisopropyl azodicarboxylate;

DIBAL-H for diisobutylaluminum hydride;

DIEA for diisopropyl ethylamine;

DMAP for N,N-dimethylaminopyridine;

DME for ethylene glycol dimethyl ether;

DMEM for Dulbecco's Modified Eagles Media;

DMF for N,N-dimethyl formamide;

DMSO for dimethylsulfoxide;

DUPHOS for

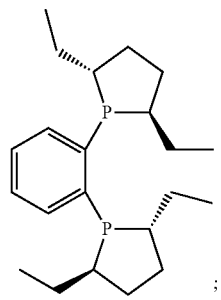 [SMILES: CC[C@@H]1CC[C@@H](CC)P1c1ccccc1P1[C@H](CC)CC[C@H]1CC]

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
HATU for O(7-Azabenzotriazole-1-yl)-N,N,N,N'-tetramethyluronium hexafluorophosphate;
Hoveyda's Cat. for Dichloro(o-isopropoxyphenylmethylene) (tricyclohexylphosphine)ruthenium(II);
KHMDS is potassium bis(trimethylsilyl)amide;
Ms for mesyl;
NMM for N-4-methylmorpholine;
PyBrOP for Bromo-tri-pyrrolidino-phosphonium hexafluorophosphate;
Ph for phenyl;
RCM for ring-closing metathesis;
RT for reverse transcription;
RT-PCR for reverse transcription-polymerase chain reaction;
TEA for triethyl amine;
TFA for trifluoroacetic acid;
THF for tetrahydrofuran;
TLC for thin layer chromatography;
TPP or PPh$_3$ for triphenylphosphine;
tBOC or Boc for tert-butyloxy carbonyl; and
Xantphos for 4,5-Bis-diphenylphosphanyl-9,9-dimethyl-9H-xanthene.

Synthetic Methods

The present invention also includes synthetic methods and processes for making compounds of formula I. The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

The general synthetic strategy is to construct one macrocyclic ring (either northwest or southeast macrocyclic ring) followed by another one. The synthesis of northwest macrocyclic ring can be achieved by intramolecular cross-coupling ring closure reaction, intramolecular alkylation, Mitsunobu ring closure reaction, intramolecular amide formation ring closure reaction or metathesis ring closure reaction. The southeast macrocyclic ring is usually constructed by ring closure metathesis reaction or intramolecular amide formation ring closure reaction.

Scheme 1

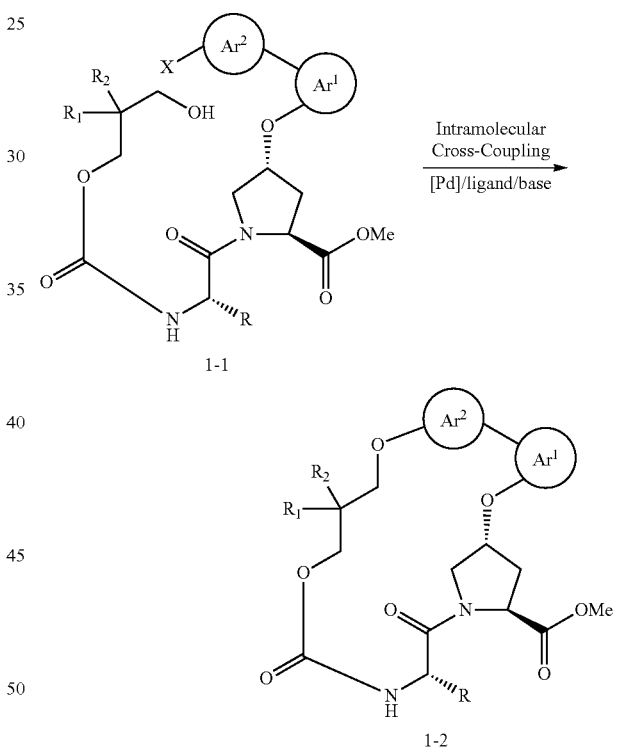

The synthesis of northwest macrocyclic ring 1-2 via intramolecular cross-coupling reaction is shown in Scheme 1. The precursor 1-1 (where X is a leaving group, such as a halogen, mesylate, tosylate or triflate and Ar$^1$ and Ar$^2$ are aryl or heteroaryl rings) closes the macrocyclic ring in the presence of transition metal such as palladium derivates, a ligand and a base. For a similar smaller ring (5 to 7 membered) closure reaction, see Karen E. Torraca, Shin-Itsu Kuwab, Stephen L. Buchwald, *J. Amer. Chem. Soc.*, 2000, 122, 12907-12908.

Scheme 2

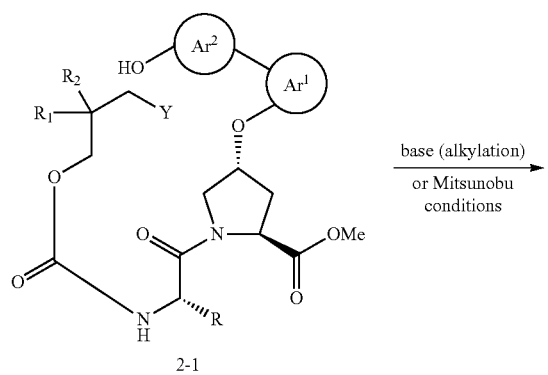
2-1 base (alkylation) or Mitsunobu conditions →

-continued

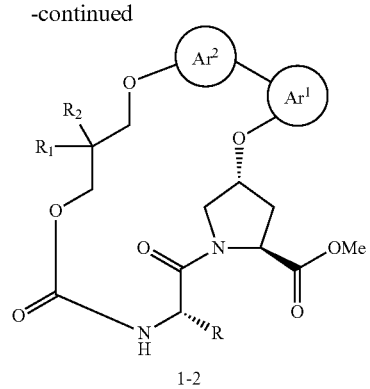
1-2

The intramolecular amide formation strategy is shown in Scheme 3. The precursor amino acid 3-1 is subjected to normal coupling reagents such as HATU/DIPEA, giving the desired macrocyclic ring 1-2.

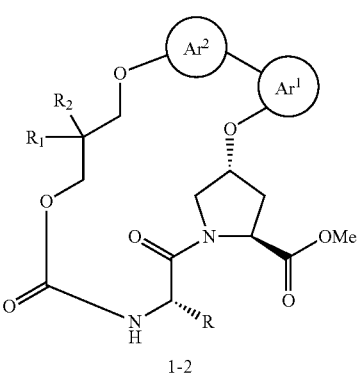
1-2

The northwest macrocyclic ring 1-2 can also be prepared from intramolecular alkylation or Mituonobu reaction of the precursor 2-1, as shown in Scheme 2. Y is a leaving group, such as a halogen, mesylate, tosylate or triflate when the intramolecular alkylation conditions are used. Y is hydroxyl group for the intramolecular Mitunobu reaction.

Scheme 3

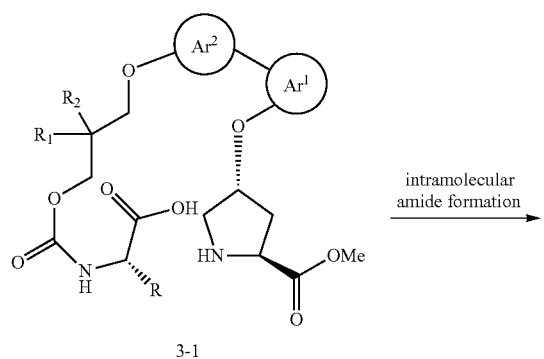
3-1 intramolecular amide formation →

Scheme 4

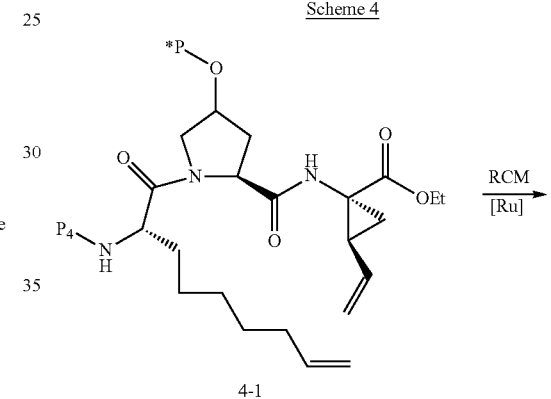
4-1

RCM [Ru] →

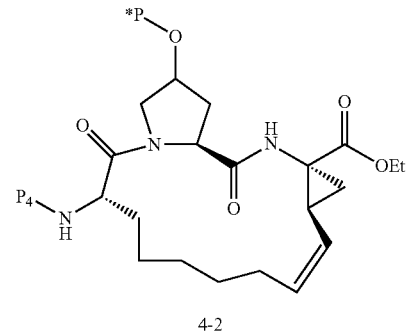
4-2

The construction of southeast macrocyclic ring via ring closure metathesis is illustrated in Scheme 4. The southeast macrocyclic ring precursor 4-1 is subjected to ring closure metathesis in the presence of a ruthenium-based catalyst to give the desired southeast macrocyclic ring core intermediate 4-2 (for further details on ring closing metathesis see recent reviews: Grubbs et al., *Acc. Chem. Res.*, 1995, 28, 446; Shrock et al., *Tetrahedron* 1999, 55, 8141; Furstner, A. *Angew. Chem. Int. Ed.* 2000, 39, 3012; Trnka et al., *Acc. Chem. Res.* 2001, 34, 18; and Hoveyda et al., *Chem. Eur. J.* 2001, 7, 945).

Scheme 5

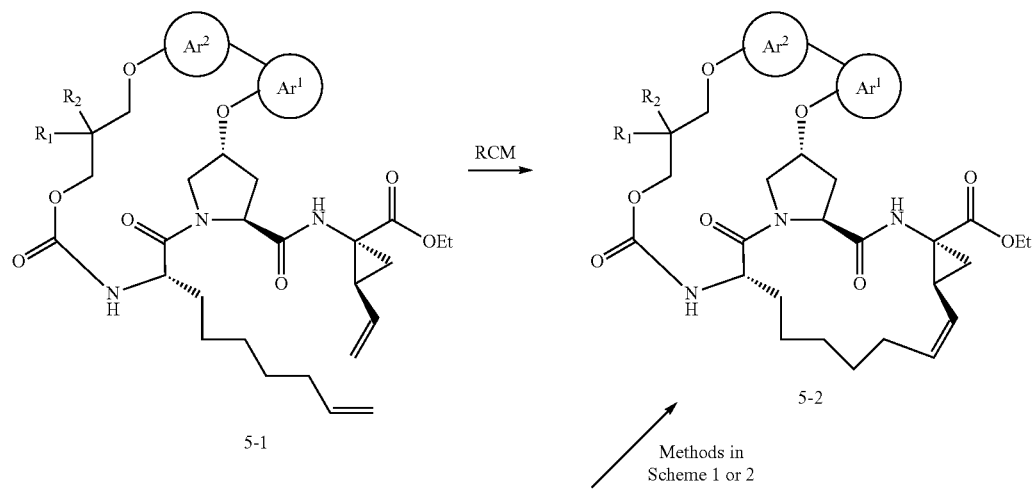

The second ring closure to assembly the bismacrocyclic core structure is illustrated in Scheme 5. The bismacrocyclic precursor 5-1, which is prepared according to Scheme 1-3, is subjected to ring closure metathesis in the presence of a ruthenium-based catalyst to give the desired bismacrocyclic ring core 5-2. Alternatively, the bismacrocyclic precursor 5-3,

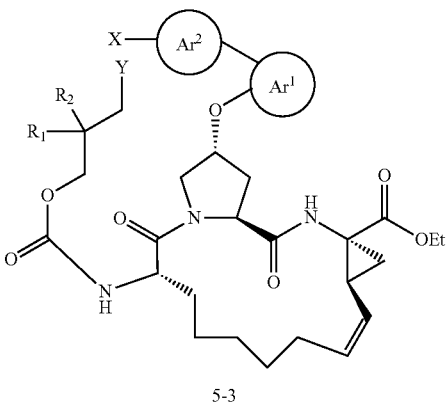

which is prepared as shown in Scheme 4, undergoes ring closure reaction as described in Scheme 1 or 2, to give the core 5-2.

The synthesis of bismacrocyclic core structure 5-2 is exemplified in Scheme 6 and 7.

Scheme 6

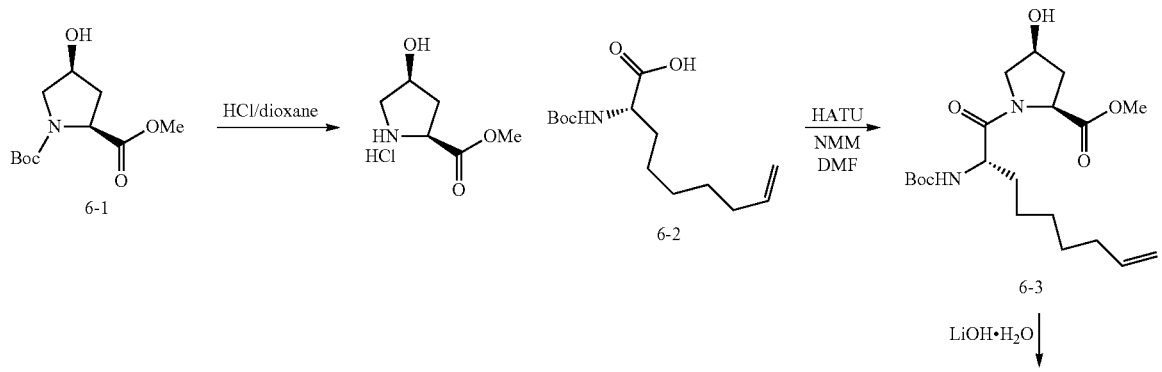

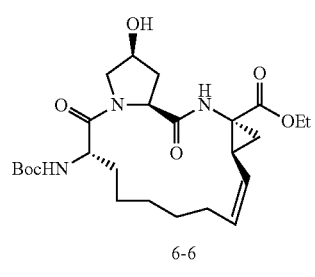
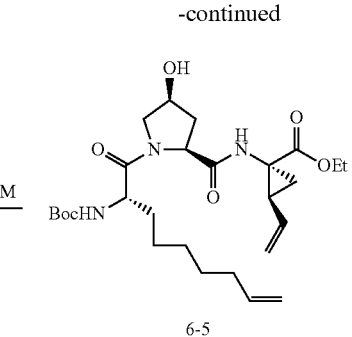
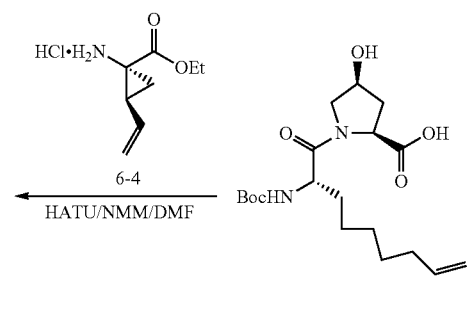

The synthesis of compound 1-6 (southeast macrocyclic ring) is outlined in Scheme 6. Deprotection of commercially available Boc-hydroxyproline 6-1 with HCl in dioxane followed by coupling with acid 6-2 using HATU, afforded intermediate 6-3. Other amino acid derivatives containing a terminal alkene may be used in place of 6-2 in order to generate varied macrocyclic structures (for further details see WO/0059929). Hydrolysis of 6-3 with LiOH followed by subsequent peptide coupling with cyclopropyl-containing amine 6-4 yielded tri-peptide 6-5. Finally, ring-closing metathesis with a ruthenium-based catalyst gave the desired intermediate 1-6.

Scheme 7

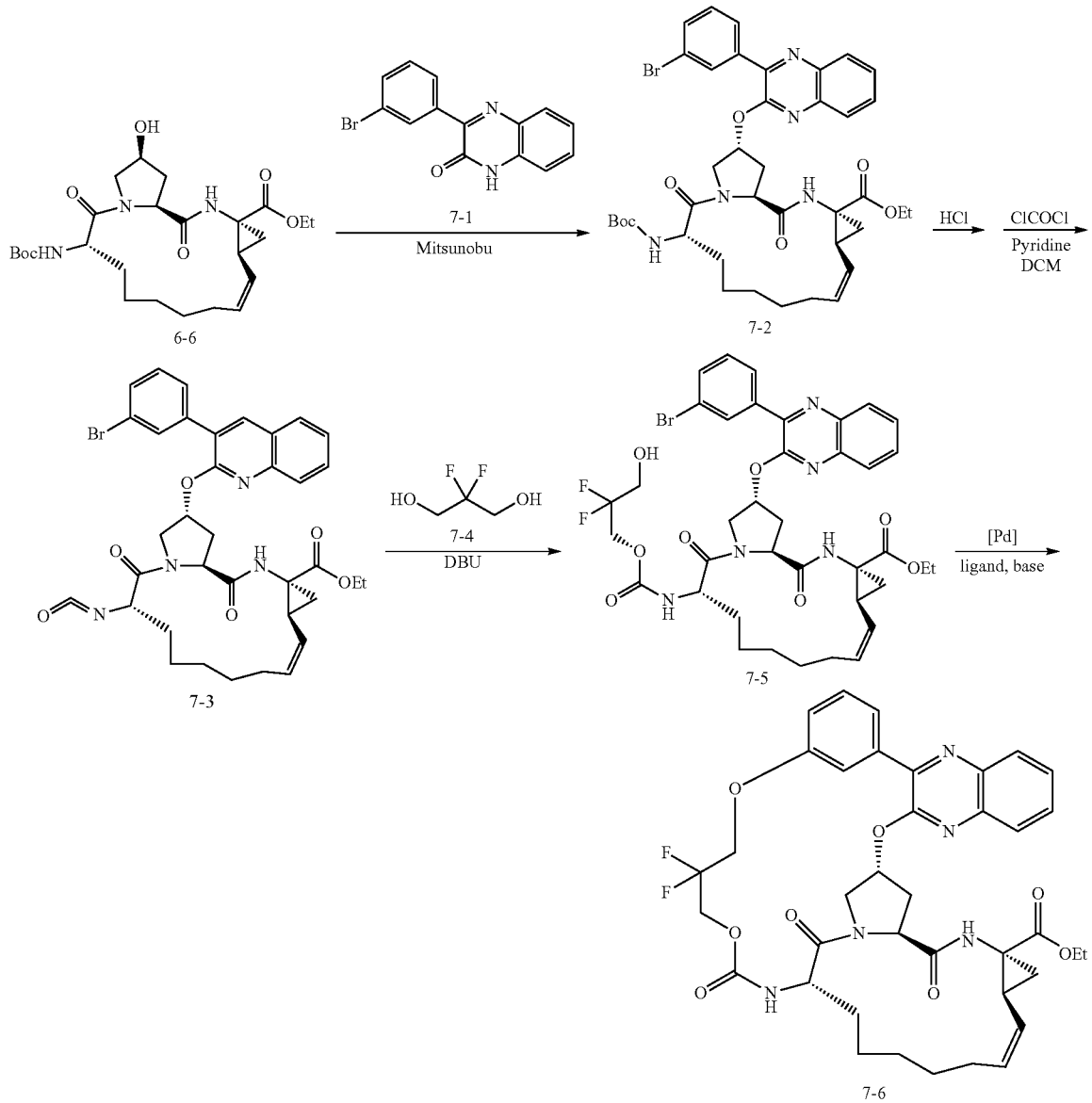

The bismacrocyclic ring core 7-6 (an example of general structure 5-2) was then prepared according to Scheme 7. The intermediate 6-6 was coupled with quionxaline derivative 7-1 under Mitsunobu conditions (such as using DIAD/Ph3P) giving compound 7-2. Attachment at the carbonyl oxygen was observed to form the desired compound. For further details on the Mitsunobu reaction, see O. Mitsunobu, *Synthesis*, 1981, 1-28; D. L. Hughes, *Org. React.*, 29, 1-162 (1983); D. L. Hughes, *Organic Preparations and Procedures Int.*, 28, 127-164 (1996); and J. A. Dodge, S. A. Jones, *Recent Res. Dev. Org. Chem.*, 1, 273-283 (1997). Compound 7-2 was subjected to acidic deprotection (such as 4N HCl) to remove Boc group, followed by the reaction with phosgene in the presence of pyridine as base to form the intermediate isocyanate 7-3. The coupling reaction of compound 7-3 with diol 7-4 in the presence of DBU resulted in the bismacrocyclic ring precursor 7-5. Finally, compound 7-5 underwent intramolecular cross-coupling reaction catalyzed by transition metal such as a palladium-based catalyst (such as palladium acetate or $Pd_2(dba)_3$, in the presence of a ligand (such as [1,1'-binaphthalen]-2-ylbis(1,1-dimethylethyl)phosphine, or bis(1,1-dimethylethyl)[2',4',6'-tris(1-methylethyl)[1,1'-biphenyl]-2-yl]phosphine) to give the bismacrocyclic compound 7-6.

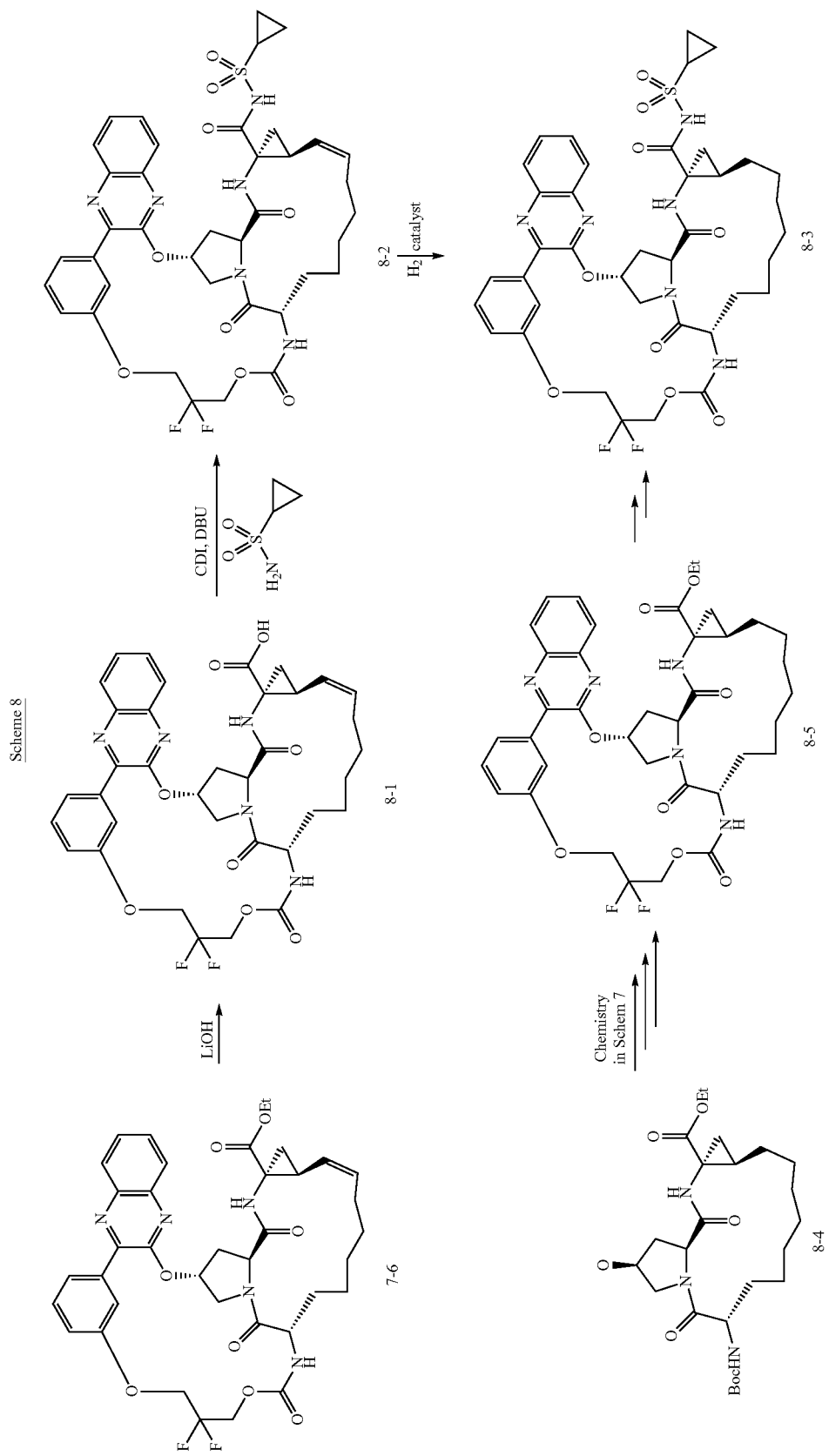

The syntheses of bismacrocyclic compounds as HCV protease inhibitors are exemplified in Scheme 8. Hydrolysis of bismacrocyclic core compound 7-6 gave the corresponding carboxylic acid 8-1 (example 1), which reacted with cyclopropylsulfonamide in the presence of CDI/DBU or other coupling reagents to afford compound 8-2 (example 2). Hydrogenation of compound 8-2 in the presence of a catalyst (such as Pd—C 10%) gave compound 8-3 (example 3). Alternatively, compound 8-3 can be prepared from compound 8-4 (the saturated analog of intermediate 6-6) using the same chemistry as described in Scheme 7 and 8.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula VI, wherein,

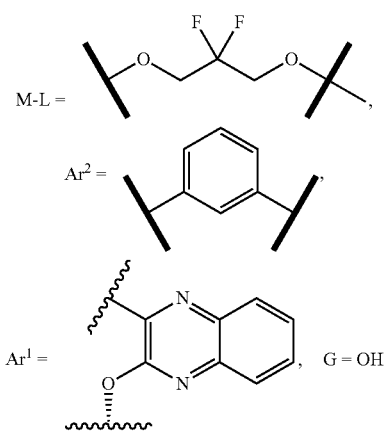

Step 1A

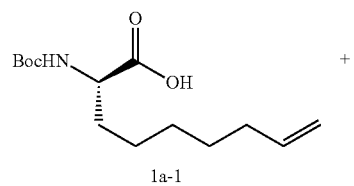

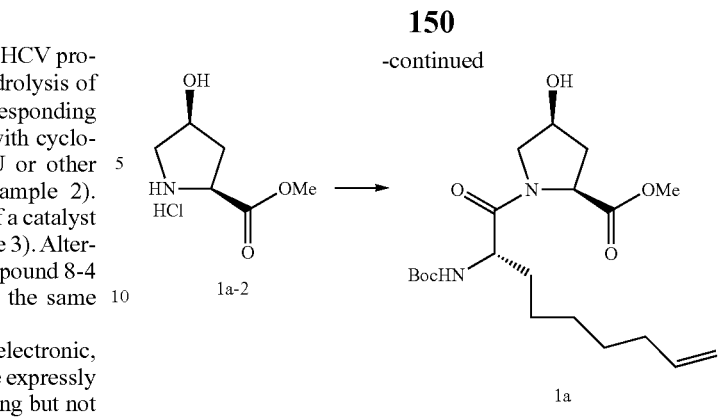

To a solution of Boc-L-2-amino-8-nonenoic acid 1a-1 (1.36 g, 5 mol) and the commercially available cis-L-hydroxyproline methyl ester 1a-2 (1.09 g, 6 mmol) in 15 ml DMF, DIEA (4 ml, 4 eq.) and HATU (4 g, 2 eq) were added. The coupling was carried out at 0° C. over a period of 1 hour. The reaction mixture was diluted with 100 mL EtOAc, and directly washed with 5% citric acid (2×20 ml), water (2×20 ml), 1M NaHCO$_3$ (4×20 ml) and brine (2×10 ml). The organic phase was dried over anhydrous Na$_2$SO$_4$, filtered, and then concentrated in vacuo, affording the dipeptide 1a (1.91 g, 95.8%) that was identified by HPLC (Retention time=8.9 min, 30-70%, 90% B), and MS (found 421.37, M+Na$^+$).

Step 1B

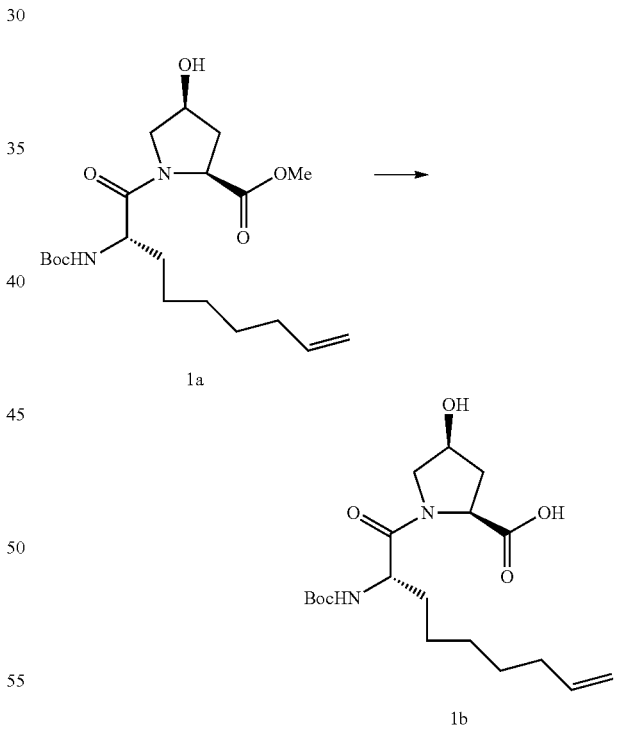

Dipeptide 1a (1.91 g) was dissolved in 15 mL of dioxane and 15 mL of 1 N LiOH aqueous solution, and the resulting mixture was stirred at room temperature for 4 hours. The reaction mixture was acidified by 5% citric acid and extracted with 100 mL EtOAc. The organic portion was then washed with water (2×20 ml), 1M NaHCO$_3$ (2×20 ml) and brine (2×20 ml). The organic phase was dried over anhydrous Na$_2$SO$_4$, filtered, and then concentrated in vacuo, yielding the free carboxylic acid compound 1b (1.79 g, 97%), which was used directly without further purification.

Step 1C

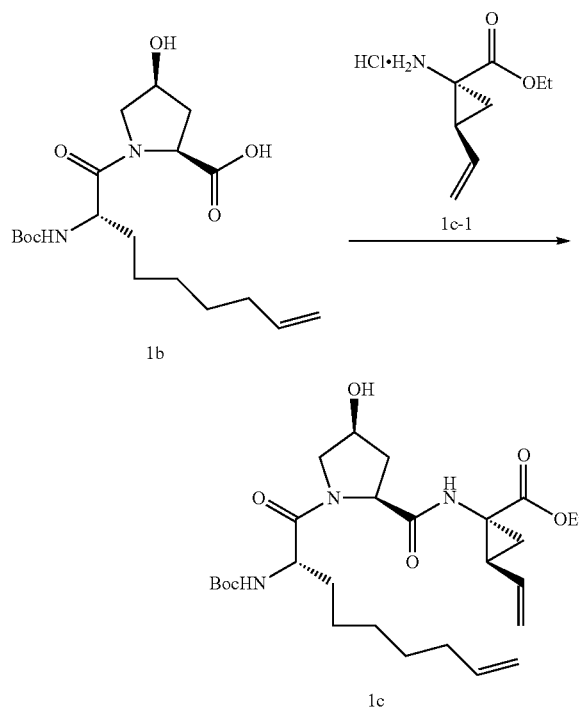

To a solution of the free acid 1b obtained above (1.77, 4.64 mmol) in 5 ml DMF, D-β-vinyl cyclopropane amino acid ethyl ester 1c-1 (0.95 g, 5 mmol), DIPEA (4 ml, 4 eq.) and HATU (4 g, 2 eq) were added. The coupling was carried out at 0° C. over a period of 5 hours. The reaction mixture was diluted with 80 mL EtOAc, and washed with 5% citric acid (2×20 ml), water (2×20 ml), 1M NaHCO$_3$ (4×20 ml), and brine (2×10 ml). The organic phase was dried over anhydrous Na$_2$SO$_4$, filtered, and then concentrated in vacuo. The residue was purified by silica gel flash chromatography using gradient elution with hexanes:EtOAc (5:1→3:1→1:1→1:2→1:5). The linear tripeptide 1c was isolated as an oil (1.59 g, 65.4%) and identified by HPLC (Retention time=11.43 min) and MS (found 544.84, M+Na$^+$).

Step 1D

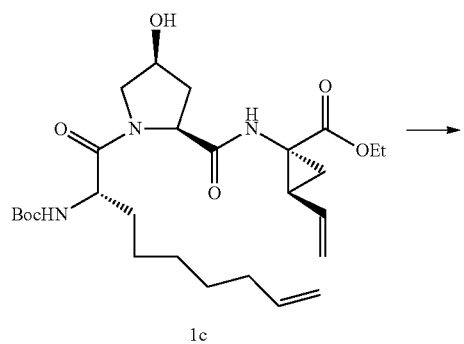

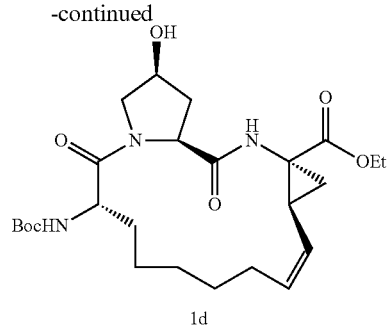

A solution of the linear tripeptide 1c (1.51 g, 2.89 mmol) in 200 ml dry DCM was deoxygenated by N$_2$ bubbling. Hoveyda's 1$^{st}$ generation catalyst (5 mol % eq.) was then added as a solid. The reaction was refluxed under N$_2$ atmosphere for 12 hours. The solvent was evaporated and the residue was purified by silica gel flash chromatography using gradient elution (hexanes/EtOAc 9:1 to 3:1 to 1:1 to 1:2 to 1:5) to give 1d as a white powder (1.24 g, 87%). MS (found 516.28, M+Na$^+$). For further details of the synthetic methods employed to produce the cyclic peptide precursor 1, see WO 00/059929 (2000).

Step 1E

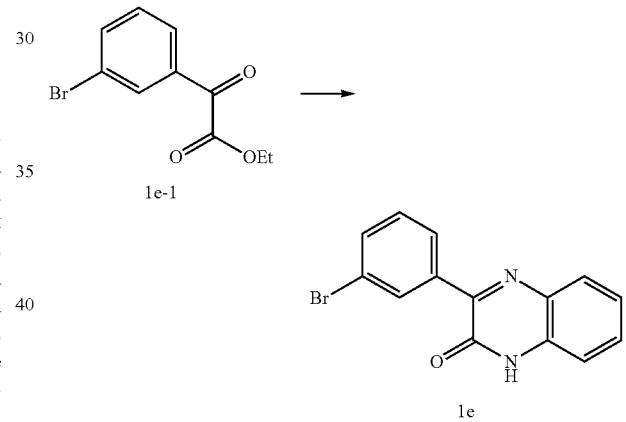

A mixture of compound 1e-1 (0.84 g, 7.77 mmol), 1,2-diaminobenzene (2 g, 7.77 mmol) and ethanol (10 m) was heated under reflux for 2 h, cooled to room temperature, filtered, washed with cold ethanol and dried under reduced pressure to afford compound 1e (2.12 g).

Step 1F

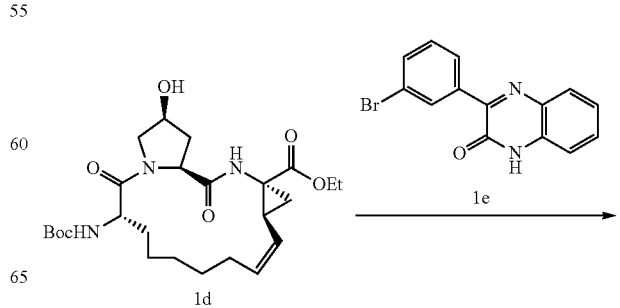

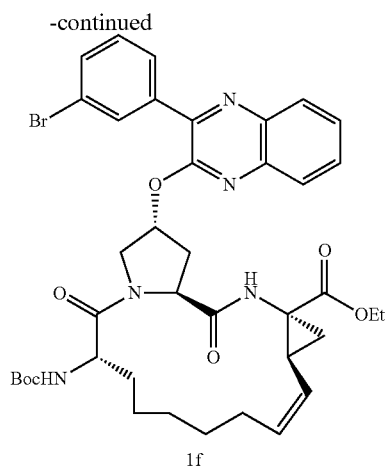

1f

To a mixture of 1d (1.4 g, 2.84 mmol), 1e (0.854 g, 2.84 mmol) and triphenylphosphine (1.4 g, 5.34 mmol) in THF at 5-10° C. was added dropwise DIAD (1.1 ml, 5.34 mmol). The resulting mixture was stirred at room temperature for 18 hours. The resulting solution was concentrated under vacuum and the residue was purified by chromatography (EtOAc/Hex: 0% to 30%) to give 1f (1.59 g). MS (ESI): m/z 776.29 (M+H), 778.29.

Step 1G

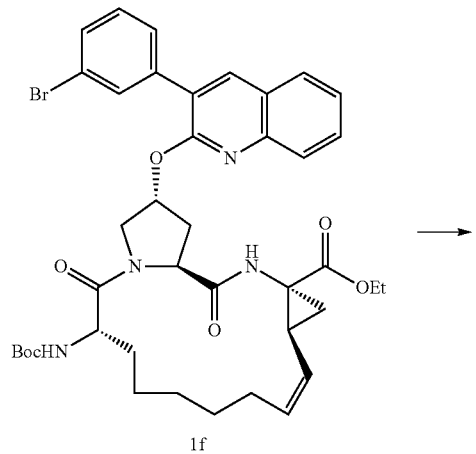

1f

A solution of compound 1f (0.6 g, 94% purity, 0.72 mmol) in dichloromethane (2 ml) was treated with 4M HCl/dioxane (3 ml, 12 mmol). The resulting mixture was stirred at room temperature for 1.5 hour, and concentrated in vacuo to dryness to afford compound 1g (100%). MS (ESI): m/z 676.07 (M+H), 678.07.

Step 1H

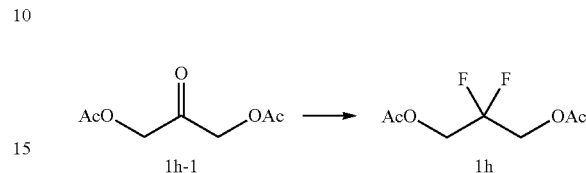

A solution of compound 1h-1 (9 g, 51.7 mmol) and DAST in a sealed vessel was stirred at room temperature for 2 days. The reaction mixture was diluted with EtOAc and added slowly to a cold sat. aq. sodium bicarbonate solution. The mixture was stirred at room temperature for 15 min. The separated organic layer was washed with brine, dried (Na2SO4) and concentrated to dryness to give the crude 1 h.

Step 1I

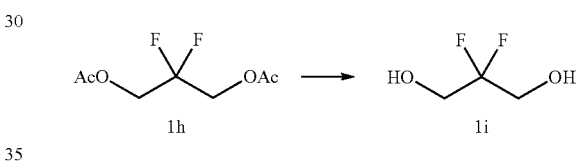

The above crude 1 h was dissolved in methanol (300 ml) and treated with a solution of sodium methoxide (25~30% in MeOH, 25 g, 117 mmol). The mixture was stirred at room temperature for 3 h and neutralized with resin Dowex C-211 H+ form (40 g) and $N HCl/dioxane (~9 ml) to pH 6~7, concentrated, filtered. The filtrate was diluted with EtOAc (150 ml), dried (Na2SO4) and concentrated to dryness to afford crude 1i (3.5 g), which can be crystallized from toluene-ether.

Step 1J

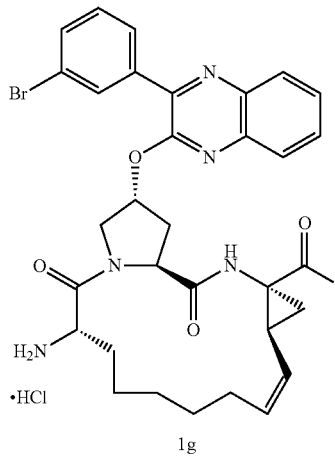

1g

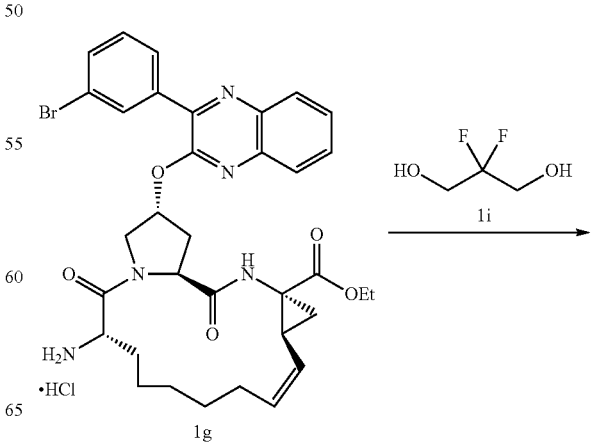

1g

-continued

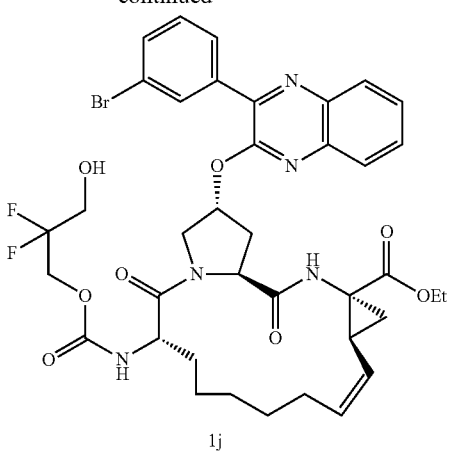

1j

-continued

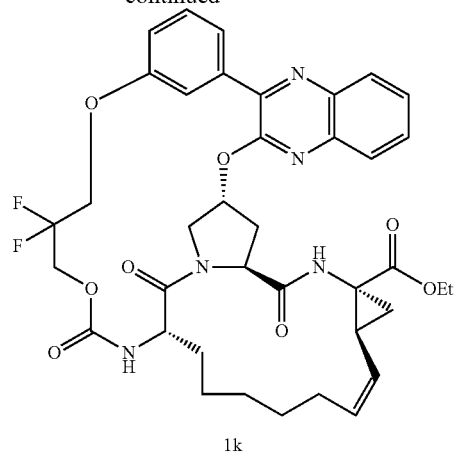

1k

To a solution of 1g (0.413 g, 0.58 mmol) in DCM (10 m) at 0° C. was added phosgene (~20% in toluene, 0.9 ml, 1.7 mmol) followed by dropwise addition of pyridine (0.75 ml, 9.3 mmol). The mixture was stirred at 0° C. for 0.5 h and at room temperature for 15 min, diluted with EtOAc, washed with water, brine (2×), dried (Na2SO4) and concentrated to dryness. The residue (the crude intermediate isocyanate) was dissolved in THF (15 ml). To this solution were added compound 1i (0.24 g, 3 eq.) and 4 A molecular sieve (~1 g). After the mixture was stirred at room temperature for 0.5 h, DBU (0.135 ml, 1.3 eq.) was added. The resulting mixture was stirred at room temperature for 1 h, diluted with EtOAc, washed with water, brine (4×), dried (Na2SO4) and concentrated. The residue was purified by silica gel column chromatography (EtOAc/Hex: 0% to 40%) to give 1j (0.238 g). MS (ESI): m/z 813.93 (M+H), 815.93.

Step 1K

A mixture of compound 1j (0.208 g, 0.256 mmol), cesium carbonate (0.167 g, 0.512 mmol) and toluene (21 ml) was purged with nitrogen for 5-10 min. Palladium acetate (12 mg, 0.051 mmol) and ligand [1,1'-binaphthalen]-2-ylbis(1,1-dimethylethyl)phosphine (26 mg, 0.064 mmol) were added. The mixture was stirred at 90° C. for 24 h, cooled to room temperature, filtered, washed with EtOAc and concentrated. The residue was purified by silica gel chromatography (EtOAc/Hexane 0% to 35% to 40%) to afford 1j (62 mg). MS (ESI); m/z 733.76 (M+H).

Step 1L

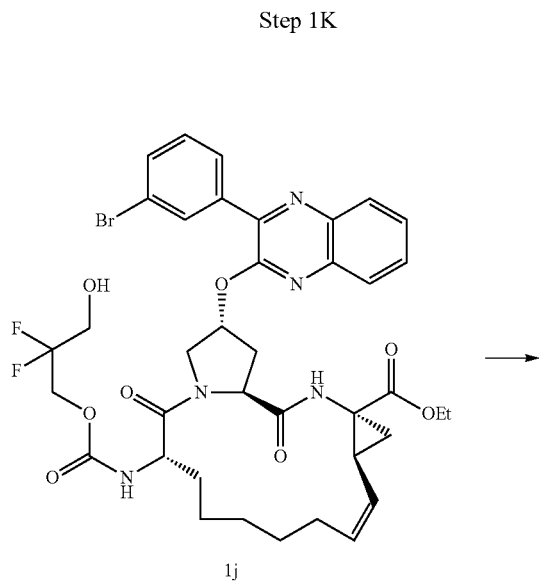

1j

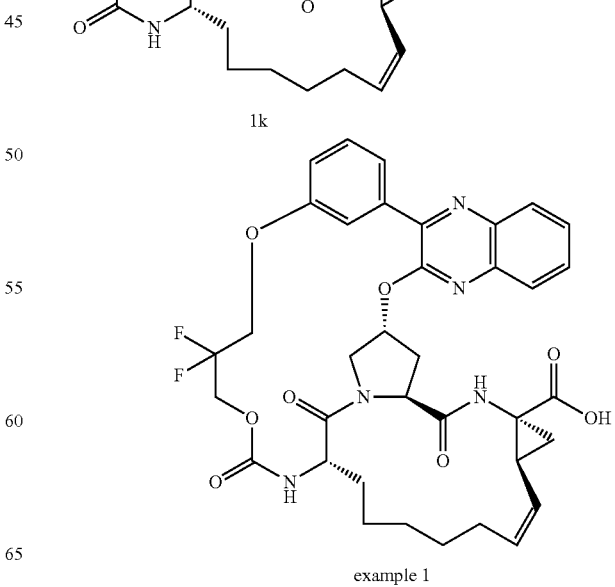

example 1

To a solution of compound 1k (59 mg, 0.08 mmol) in THF/MeOH (3 ml/1.5 ml) was added 1N lithium hydroxide (1.5 ml, 1.5 mmol). The mixture was stirred at room temperature for 20 hours. Most organic solvents were evaporated in vacuo, and the resulting residue was diluted with water and acidified to pH 3 to 4. The mixture was extracted with EtOAc three times. The combined organic extracts were dried (Na2SO4), filtered and concentrated in vacuo to afford the title compound (55 mg). MS (ESI): m/z 706.33 (M+H).

Example 2

Compound of Formula VI, wherein,

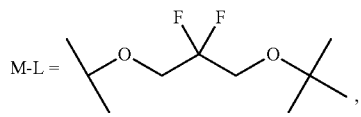

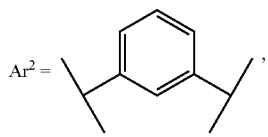

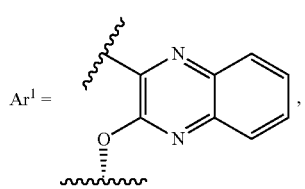

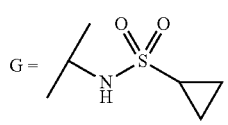

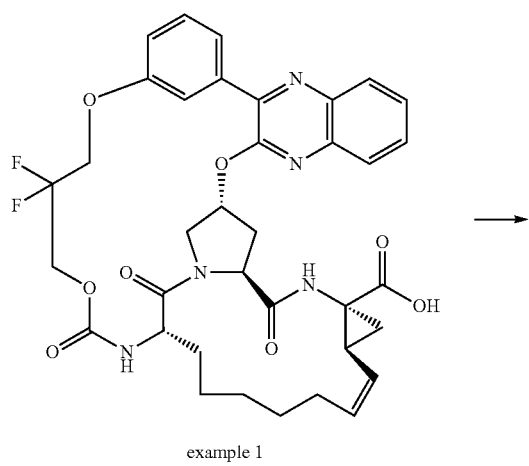

example 1

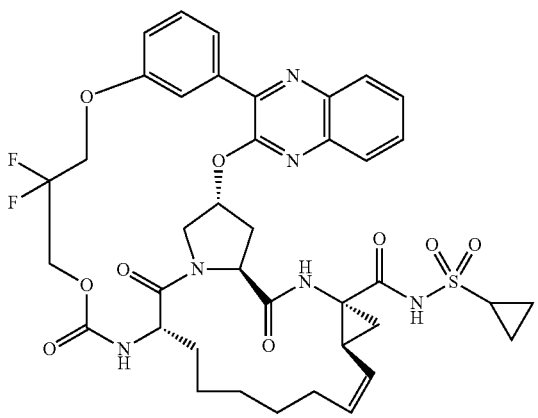

example 2

The title compound from Example 1 (38 mg, 0.0547 mmol) and carbonyldiimidazole (19 mg, 1.15 mmol) were dissolved in 2 ml anhydrous DMF and the resulting solution was heated to 40° C. for 1 hour. Cyclopropylsulfonamide (19 mg, 0.157 mmol) was added to the reaction followed by DBU (0.025 ml, 0.164 mmol). The reaction mixture was stirred at 40° C. for 18 hours. The reaction was cooled down and diluted with ethyl acetate, washed with water, 0.5M aq. KH$_2$PO$_4$, brine, dried over anhydrous sodium sulfate and concentrated in vacuo. The residue was purified by preparative HPLC to afford the title compound (17 mg). MS (ESI): m/z 809.29 (M+H).

Example 3

Compound of Formula VII, wherein,

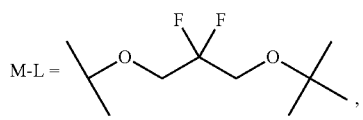

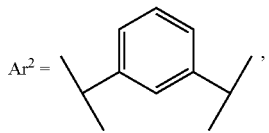

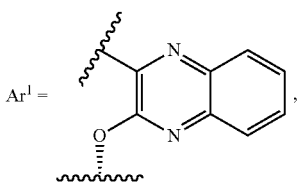

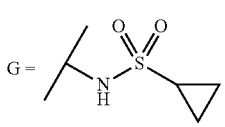

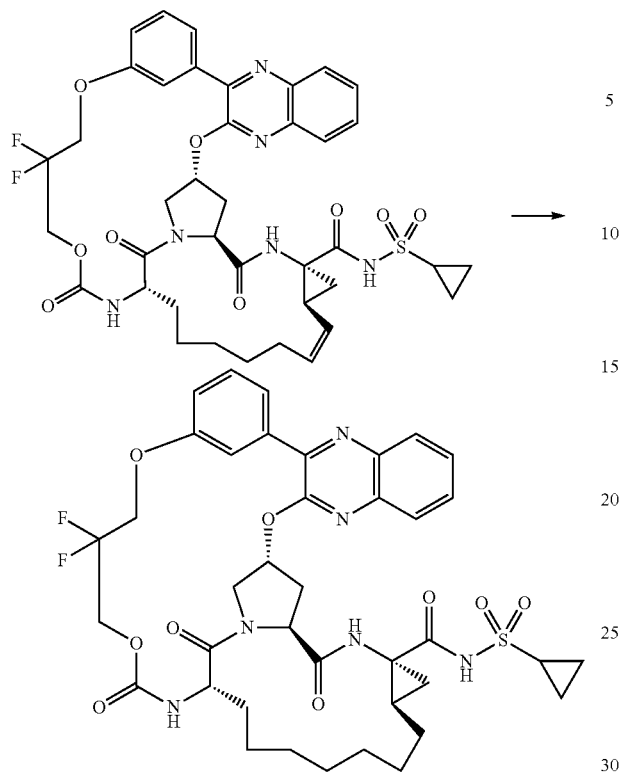

Example 2

Example 3

A mixture of the title compound from Example 2 (10 mg), Pd—C (10%, 5 mg), DIPEA (0.03 ml) and EtOAc (4 ml) was hydrogenated (1 atm) for ~2 h, filtered and concentrated. The residue was purified by preparative HPLC to afford the title compound (2.5 mg). MS (ESI): m/z 811.30 (M+H).

Example 4

Compound of Formula VI, wherein,

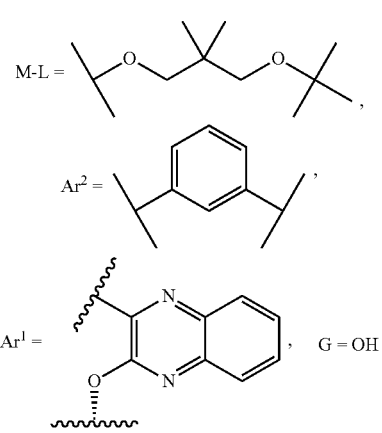

The title compound was prepared by the same procedures as described in Example 1 MS (ESI): m/z 698.38 (M+H).

Example 5

Compound of Formula VI, wherein,

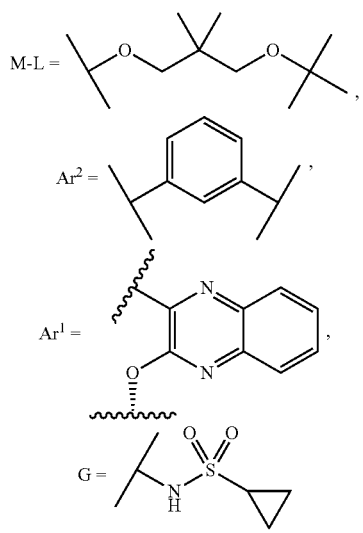

The title compound was prepared by the same procedures as described in Example 2 MS (ESI): m/z 801.38 (M+H).

Example 6

Compound of Formula VII, wherein,

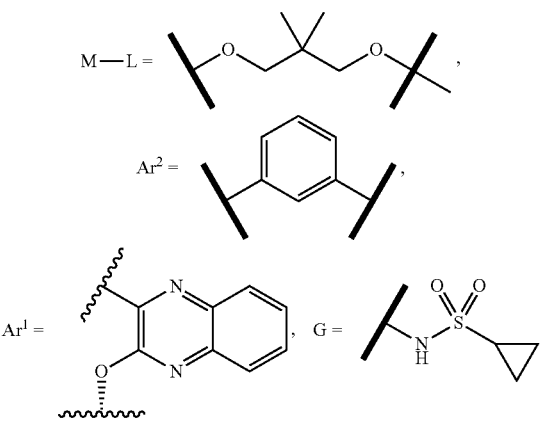

The title compound was prepared by the same procedures as described in Example 3 MS (ESI): m/z 803.16 (M+H).

Example 7

Compound of Formula VI, wherein,

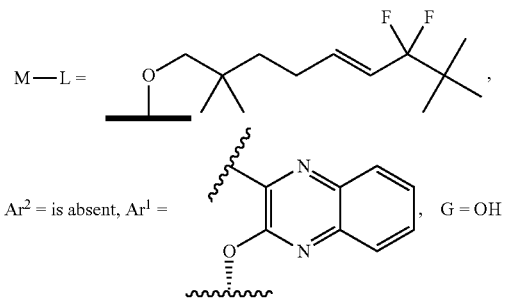

Step 7A

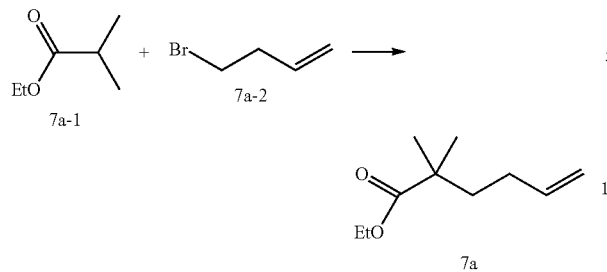

To DIPEA (10.3 ml, 72.8 mmol) in THF (40 ml) at −78° C. was added n-BuLi (28 ml, 70 mmol, 2.5M in hexane) dropwise. The resulting solution was warmed up to 0° C. and stir for 15 min then cooled down to −70° C. A solution of ester 7a-1 (8.5 ml, 63.6 mmol) in THF (40 ml) was added over 1 h, the resulting solution was stirred at −70° C. for 1 h. Compound 7a-2 (7.1 ml, 70 mmol) in HMPA (16 ml) was then added slowly with the internal temperature maintained below −50° C. and the mixture was stirred at −50° C. for 5 h. HCl (8 ml, 1N) and water (80 ml) was added, the resulting mixture was extracted with ethyl ether. The organic solvents were combined and evaporated in vacuo to give 7a (9.8 g).

Step 7B

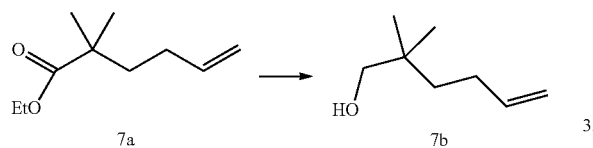

To a solution of LAH in ethyl ether at 0° C. was added slowly 7a (9.79 g) in ethyl ether (80 ml) over 1 h. The resulting mixture was warmed up to r.t. and stirred for 2 h. The mixture was cooled down to 0° C., and quenched with EtOAc (20 ml) and HCl (6N) and extracted with EtOAc. The organic layers were combined, washed with brine, dried ($Na_2SO_4$) and evaporated in vacuo to give 7b (6.77 g).

Step 7C

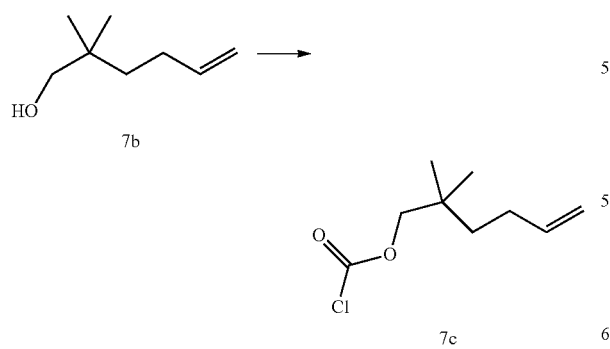

To a solution of phosgene (20 ml, 20% in toluene) at 10° C. to 20° C. was added 7b (3.03 g) dropwise. The resulting mixture was stirred at r.t. for up to 3 h. The mixture was evaporated in vacuo to remove half of toluene, the resulting solution was diluted with DCM and the solvents were removed in vacuo to give 7c (4.4 g).

Step 7D

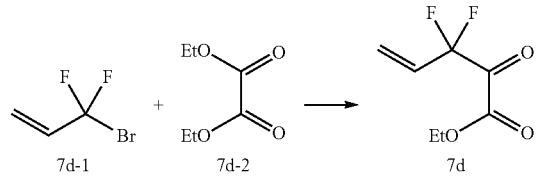

To a solution of 7d-1 (5.8 g, 36.88 mmol) and 7d-2 (5.0 ml, 36.88 mmol) in THF (174 ml), ethyl ether (44 ml) and n-pentane (44 ml) at −100° C. to −95° C. was added dropwise n-BuLi (15.6 ml, 39 mmol, 2.5M in hexane) over 30 min. The resulting mixture was stirred at −95° C. for 1 h, and −78° C. for 2 h, and then quenched with aq. $NH_4Cl$ (2.5 g in 30 ml water). The mixture was extracted with MTBE (300 ml), and the organic layer was washed with 1N HCl, brine and dried ($Na_2SO_4$) and evaporated in vacuo to give crude 7d (6.32 g). A portion of the crude 7d (1.8 g) was purified by silica gel column chromatography (EtOAc/Hex: 0% to 40%) to give 7d (1.02 g).

Step 7E

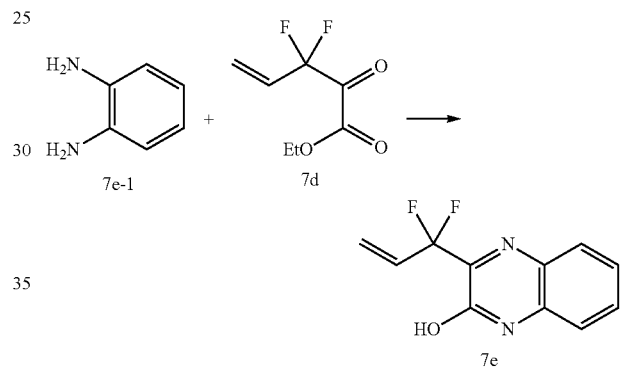

To a solution of 7d (1.02 g, 5.73 mmol) in EtOH (22 ml) was added 7e-1 (0.65 g, 1.07 mmol) and the resulting mixture was stirred at 80° C. for 2 h. The mixture was cooled down to r.t., concentrated in vacuo, and the resulting residue was purified by silica gel column chromatography (EtOAc/Hex: 0% to 35%) to give 7e (618 mg).

Step 7F

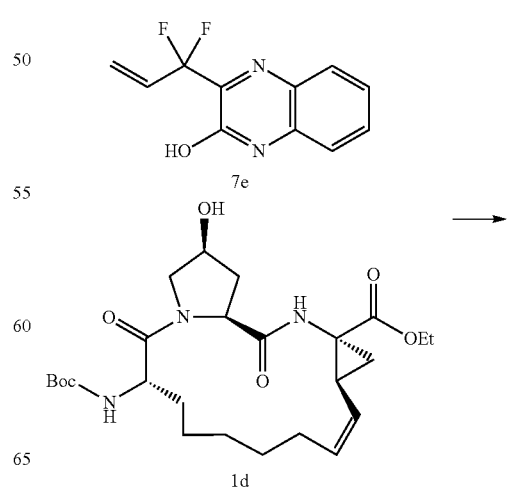

Step 7G

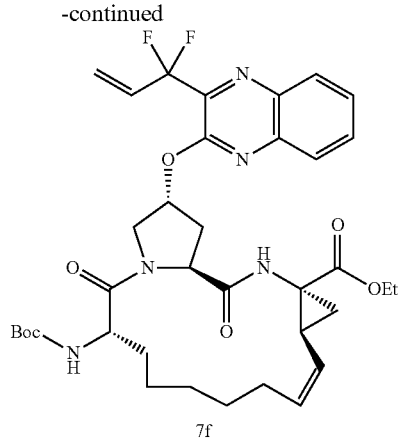

7f

A solution of compound 7e (229 mg, 1.03 mmol), 1d (509 mg, 1.03 mmol) and PPh$_3$ (586 mg, 2.06 mmol) in THF (8 ml) was added DIAD (0.45 ml). The resulting mixture was stirred at r.t. for 14 h and the organic solvents were evaporated in vacuo. The residue was purified by silica gel column chromatography (EtOAc/Hex: 0% to 35%) to give 7f (413 mg). MS (ESI): m/z 698.33 (M+H).

Step 7G

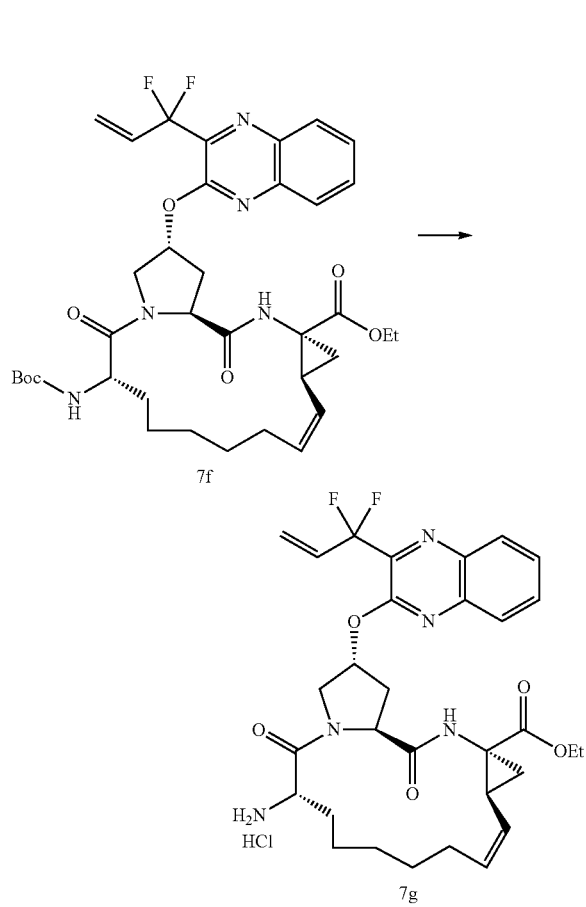

7f

7g

A solution of compound 7f (409 mg, 0.586 mmol) in DCM (1 ml) was added HCl (2 ml, 4N in dioxane). The resulting mixture was stirred at r.t. for 2 h. The organic solvents were evaporated in vacuo to give 7g. MS (ESI): m/z 598.29 (M+H).

Step 7H

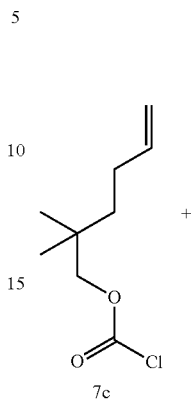

7c

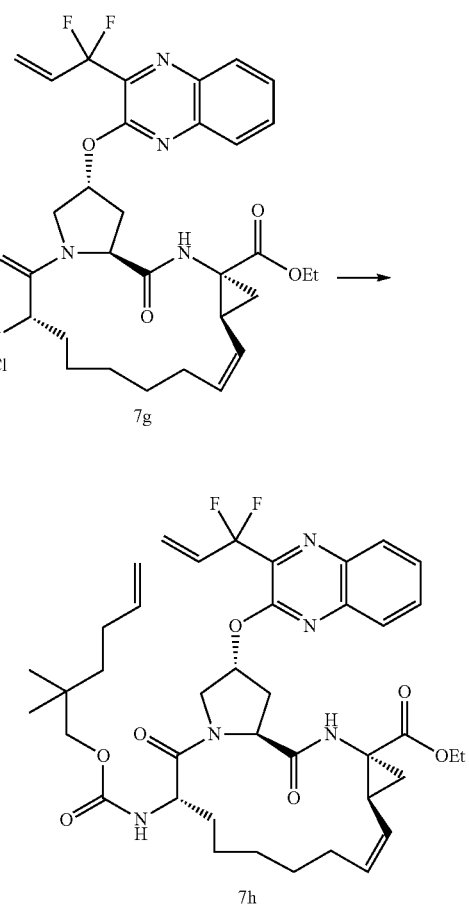

7g

7h

To a solution of compound 7g (~0.586 mmol) in DCM (5 ml) at 0° C. was added Et$_3$N (0.25 ml) and 7c (150 mg). The resulting mixture was stirred at 0° C. for 20 min and then r.t. for 30 min. This was followed by addition of another portion of 7c (15 mg) and stirred for another 1 h. The mixture was diluted with EtOAc, washed with water, brine and dried (Na$_2$SO$_4$) and evaporated in vacuo. The residue was purified by silica gel column chromatography (EtOAc/Hex: 0% to 100%) to give 7h (0.23 g). MS (ESI): m/z 752.41 (M+H).

Step 7I

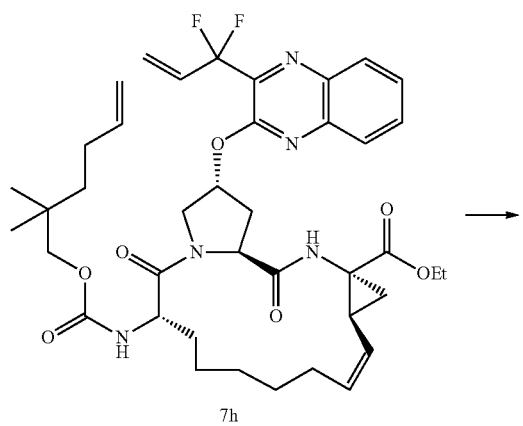

7h

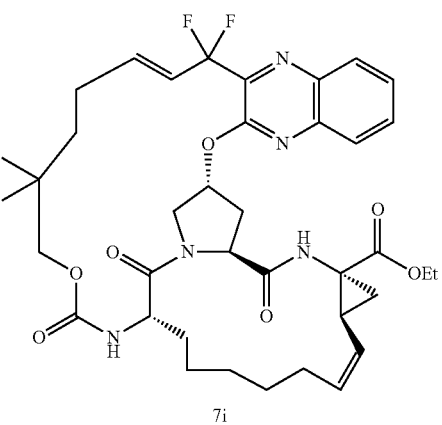

7i

A solution of compound 7h (222 mg, 0.295 mmol) in toluene (60 ml) was degassed and Zhan 1B catalyst (22 mg, 0.03 mmol) was added. The resulting mixture was degassed and stirred at 100° C. under nitrogen gas for 5 h. The organic solvents were evaporated in vacuo, and the resulting residue was purified by silica gel column chromatography (EtOAc/Hex: 0% to 35%) to give 7i (0.106 g). MS (ESI): m/z 724.31 (M+H).

Step 7J

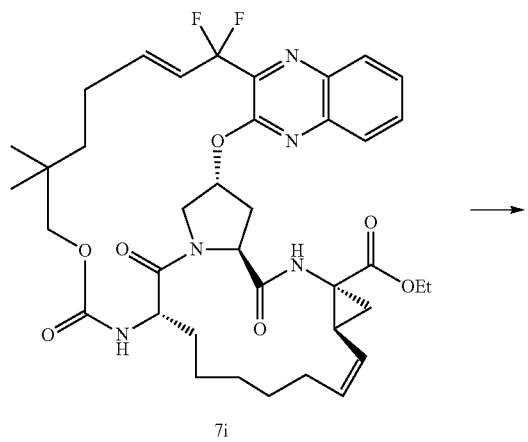

7i

-continued

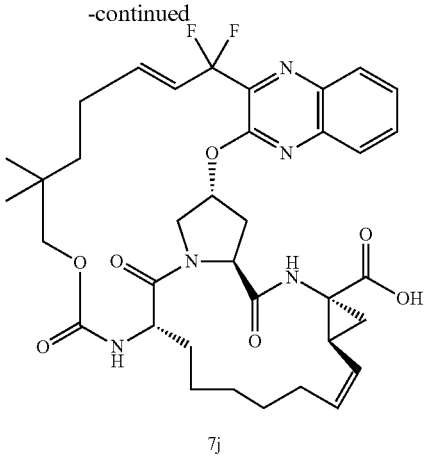

7j

To a solution of compound 7i (73 mg, 0.1 mmol) in THF/MeOH (4 ml/2 ml) was added 1N lithium hydroxide (2 ml, 2.0 mmol). The mixture was stirred at room temperature for 24 hours. Most organic solvents were evaporated in vacuo, and the resulting residue was diluted with water and acidified to pH 4 to 5. The mixture was extracted with EtOAc three times. The combined organic extracts were dried (Na2SO4), filtered and concentrated in vacuo to afford the title compound (70 mg). MS (ESI): m/z 696.18 (M+H).

Example 8

Compound of Formula VI, wherein,

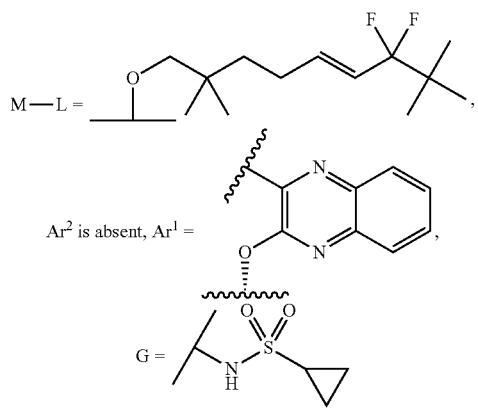

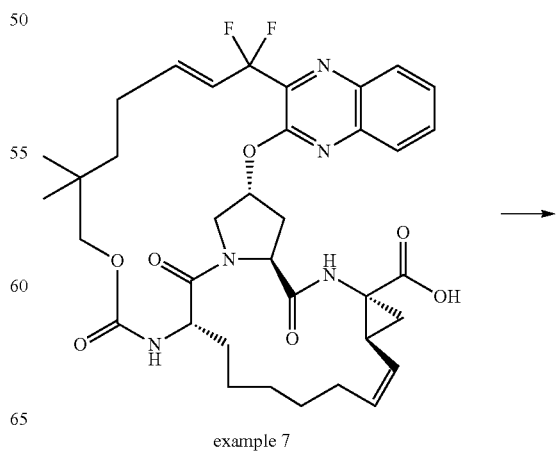

example 7

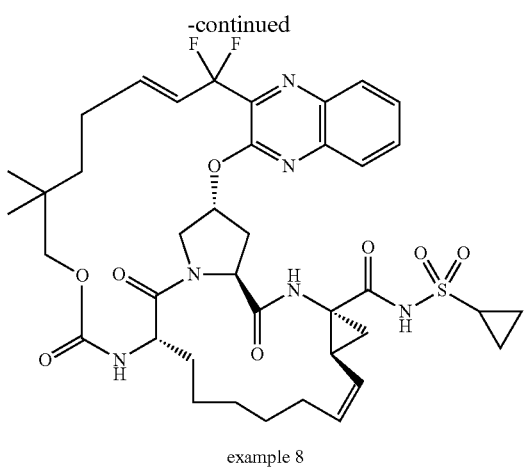

example 8

The title compound from Example 7 (70 mg, 0.1 mmol) and carbonyldiimidazole (34 mg, 0.21 mmol) were dissolved in 2 ml anhydrous DMF and the resulting solution was heated to 40° C. for 1 hour. Cyclopropylsulfonamide (29 mg, 0.24 mmol) was added to the reaction followed by DBU (0.039 ml, 0.26 mmol). The reaction mixture was stirred at 40° C. for 18 hours. The reaction was cooled down and diluted with ethyl acetate, washed with water, 0.5M aq. $KH_2PO_4$, brine, dried over anhydrous sodium sulfate and concentrated in vacuo. The residue was purified by preparative HPLC to afford the title compound (45 mg). MS (ESI): m/z 799.37 (M+H). Examples 9 to 455, compounds of Formula VI or VII in Table 1, are made following the procedures described in Examples 1 to 8 and the Synthetic Methods section.

The compounds of the present invention exhibit potent inhibitory properties against the HCV NS3 protease. The following examples describe assays in which the compounds of the present invention can be tested for anti-HCV effects.

Example 456

NS3/NS4a Protease Enzyme Assay

The ability of the compounds to inhibit the HCV NS3 protease is determined using the assay described in published US patent application 2010/0003214, incorporated herein by reference in its entirety.

Example 457

Cell-Based Replicon Assay

The anti-HCV activity of the compounds is determined using the cell-based replicon assay and the HCV replication assay described in US Publication No: 2010/0003214, incorporated herein by reference in its entirety.
HCV Replicon Assay—Luciferase Since clinical drug resistance often develops in viral infections following single agent therapies, there is a need to assess the additive, antagonistic, or synergistic properties of combination therapies. We use the HCV replicon system to assess the potential use of the compound of the present invention or in combination therapies with Interferon alpha, cyclosporine analogs and inhibitors targeting other HCV proteins. The acute effects of a single or combinations of drugs are studied in the "Huh-luc/neo-ET" replicon with each chemical agent titrated in an X or Y direction in a 6 point two-fold dilution curve centered around the EC50 of each drug. Briefly, replicon cells are seeded at 7,000 cells per well in 90 ul DMEM (without phenol red, Invitrogen Cat.#31053-036) per well with 10% FCS, 1% non-essential amino acids, 1% of Glutamax and 1% of 100× penicillin/streptomycin and incubated overnight at 37° C., 5% $CO_2$, 100% relative humidity. 16-20 h after seeding cells, test compounds previously solubilized and titrated in dimethyl sulfoxide ("DMSO") from each X plate and Y plate are diluted 1:100 in DMEM (without phenol red, Invitrogen Cat.#31053-036) with 10% FCS, 1% non-essential amino acids, 1% of Glutamax and 1% of 100× penicillin/streptomycin and added directly to the 96-well plate containing cells and growth medium at a 1:10 dilution for a final dilution of compound and DMSO of 1:1000 (0.2% DMSO final concentration). Drug treated cells are incubated at 37° C., 5% $CO_2$, 100% relative humidity for 72 hours before performing a luciferase assay using 100 ul per well BriteLite Plus (Perkin Elmer) according to the manufacturer's instructions. Data analysis utilizes the method published by Prichard and Shipman (Antiviral Research, 1990. 14:181-205). Using this method, the combination data are analyzed for antagonistic, additive, or synergistic combination effects across the entire combination surface created by the diluted compounds in combination.

The compounds of the present invention can be effective against the HCV 1b genotype. It should also be understood that the compounds of the present invention can inhibit multiple genotypes of HCV. In one embodiment compound of the present invention are active against the 1a, 1b, 2a, 2b, 3a, 4a, and 5a genotypes. Table 2 shows the $EC_{50}$ values of representative compounds of the present invention against the HCV 1b genotype from the above described qRT-PCR or luciferase assay. $EC_{50}$ ranges against HCV 1b are as follows: A>10 nM; B1-10 nM; C<1 nM.

TABLE 2

| Genotype-1b replicon $EC_{50}$ | | | | | |
|---|---|---|---|---|---|
| Example | Range | Example | Range | Example | Range |
| 2 | C | 5 | C | 6 | C |
| 8 | C | | | | |

While this invention has been particularly shown and described with references to preferred embodiments thereof, it will be understood by those skilled in the art that various changes in form and details may be made therein without departing from the scope of the invention encompassed by the appended claims.

What is claimed:
1. A compound of Formula III:

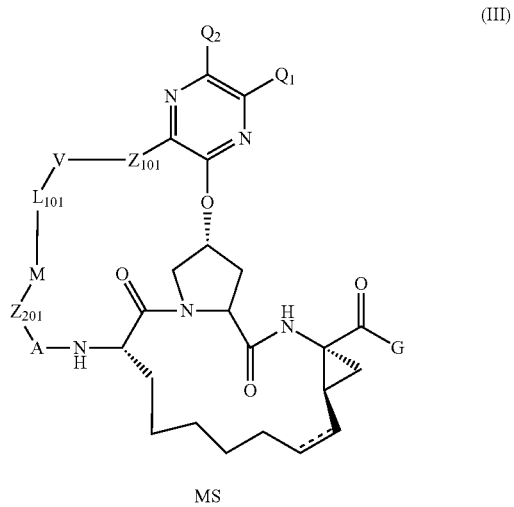

(III)

MS or a pharmaceutically acceptable salt, ester or prodrug thereof, wherein:

A is —C(O);

—$Z_{201}$-M-$L_{101}$-V— is

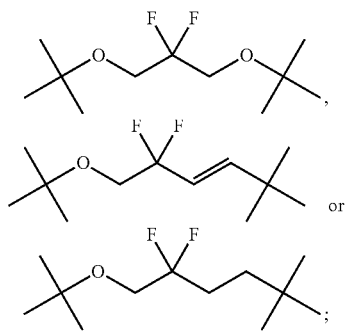

$Z_{101}$ is selected from aryl, substituted aryl, heteroaryl, and substituted heteroaryl;

$Q_1$ is selected from the group consisting of:
(i) hydrogen;
(ii) aryl; substituted aryl; heteroaryl; substituted heteroaryl;
(iii) heterocycloalkyl or substituted heterocycloalkyl;
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

Q2 is selected from the group consisting of:
(i) hydrogen, halogen, CN, $CF_3$, $N_3$, $NO_2$, $OR_1$, $SR_1$, $SO_2R_2$, —$NHS(O)_2$—$R_2$, —$NH(SO_2)NR_3R_4$, $NR_3R_4$, $CO_2R_1$, $COR_1$, $CONR_1R_2$, $N(R_1)COR_2$; where $R_1$, $R_2$, $R_3$ and $R_4$ are as previously defined;
(ii) aryl; substituted aryl; heteroaryl; substituted heteroaryl;
(iii) heterocycloalkyl or substituted heterocycloalkyl;
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;

or $Q_1$ and $Q_2$, taken together with the carbon atoms to which they are attached, form a carbocyclic moiety or a heterocyclic moiety;

G is selected from —OH, —$NHS(O)_2$—$R_2$, —$NH(SO_2)NR_3R_4$, and $NR_3R_4$;

$R_2$ is selected from:
(i) aryl; substituted aryl; heteroaryl; substituted heteroaryl;
(ii) heterocycloalkyl; substituted heterocycloalkyl;
(iii) —$C_1$-$C_8$ alkyl, —$C_2$-$C_8$ alkenyl, or —$C_2$-$C_8$ alkynyl each containing 0, 1, 2, or 3 heteroatoms selected from O, S or N, substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl; heterocylic; substituted heterocyclic;

$R_3$ and $R_4$ are independently selected from:
(i) hydrogen;
(ii) aryl; substituted aryl; heteroaryl; substituted heteroaryl;
(iii) heterocycloalkyl or substituted heterocycloalkyl;
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl; heterocyclic, or substituted heterocyclic;

alternatively, $R_3$ and $R_4$ are taken together with the nitrogen atom to which they are attached form a heterocyclic or substituted heterocyclic; and $=$ denotes a carbon-carbon single or double bond.

2. The compound of claim 1, wherein the compound is of Formula IV:

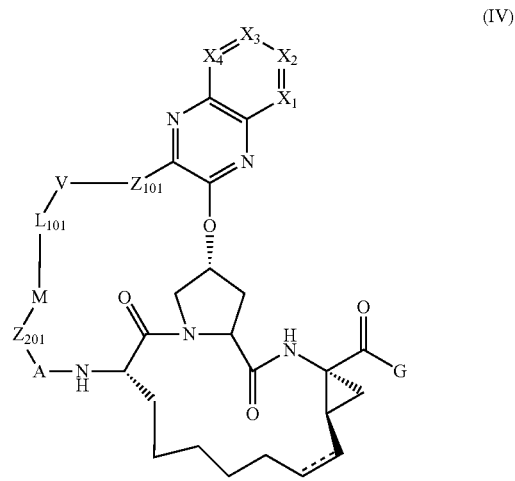

(IV)

or a pharmaceutically acceptable salt, ester or prodrug thereof, where $X_1$-$X_4$ are independently selected from —$CR_5$ and N, wherein $R_5$ is independently selected from:

(i) hydrogen; halogen; —$NO_2$; —CN; $N_3$; $CF_3$;
(ii) -M-$R_4$, M is O, S, NH;
(iii) $NR_3R_4$;
(iv) —$C_1$-$C_8$ alkyl, —$C_2$-$C_8$ alkenyl, or —$C_2$-$C_8$ alkynyl each containing 0, 1, 2, or 3 heteroatoms selected from O, S, or N; substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl;
(v) aryl; substituted aryl; heteroaryl; substituted heteroaryl;
(vi) heterocycloalkyl or substituted heterocycloalkyl;

where A, $Z_{201}$, M, $L_{101}$, V, $Z_{101}$ and G are as defined in claim 1, and $=$ denotes a carbon-carbon single or double bond.

3. The compound of claim 1, wherein the compound is of Formula V:

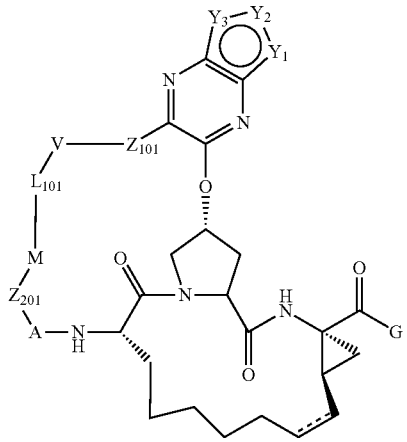

(V)

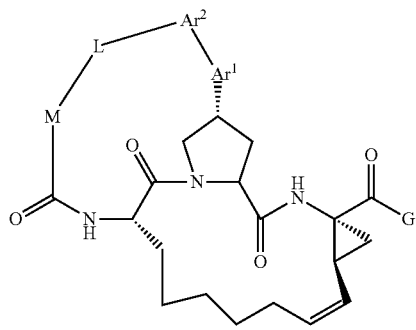

(VI)

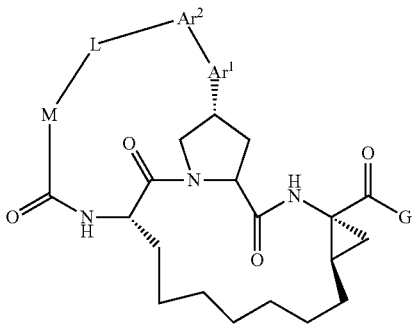

(VII)

or a pharmaceutically acceptable salt, ester or prodrug thereof, where $Y_1$-$Y_3$ are independently selected from $CR_5$, N, $NR_5$, S and O; where $R_5$, A, $Z_{201}$, M, $L_{101}$, V, $Z_{101}$ and G are as defined in claim 1, and ═ denotes a carbon-carbon single or double bond.

4. A compound selected from compounds of Formula VI or VII wherein M-L, $Ar^2$, $Ar^1$ and G are delineated in Table 1:

TABLE 1

| Example # | M-L | $Ar^2$ | $Ar^1$ | G | Formula |
|---|---|---|---|---|---|
| 1. | ![M-L structure] | ![Ar2 structure] | ![Ar1 structure] | OH | VI |
| 2. | ![M-L structure] | ![Ar2 structure] | ![Ar1 structure] | ![G structure sulfonamide cyclopropyl] | VI |
| 3. | ![M-L structure] | ![Ar2 structure] | ![Ar1 structure] | ![G structure sulfonamide cyclopropyl] | VII |
| 13. | ![M-L structure] | ![Ar2 structure] | ![Ar1 structure] | OH | VI |

TABLE 1-continued
| Example # | M-L | Ar² | Ar¹ | G | Formula |
|---|---|---|---|---|---|
| 14. | 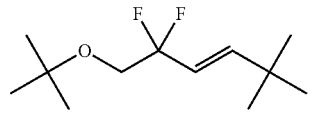 | 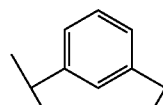 | 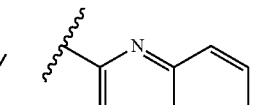 | 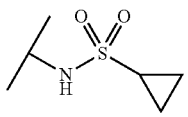 | VI |
| 15. | 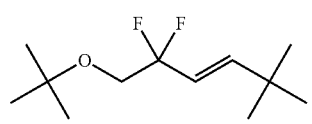 | 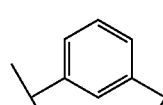 | 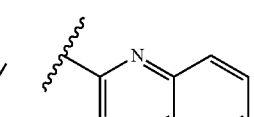 | 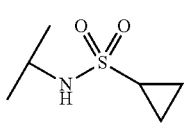 | VII |
| 54. | 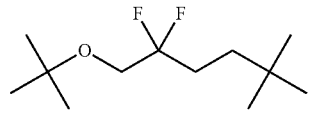 | 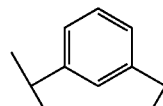 | 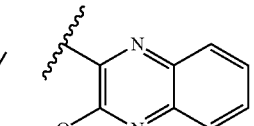 | 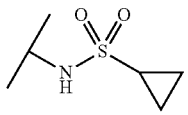 | VI |
| 55. | 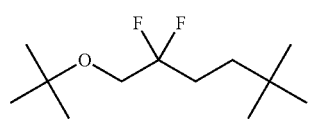 | 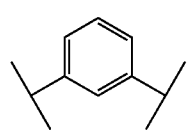 | 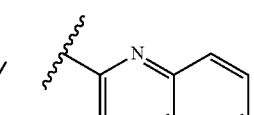 | 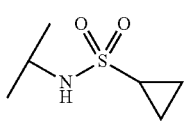 | VII |
| 92. | 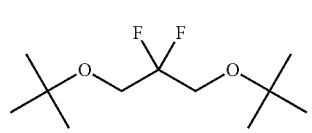 | 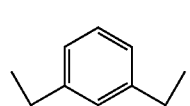 | 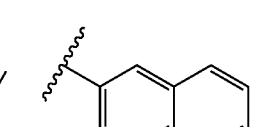 | OH | VI |
| 93. | 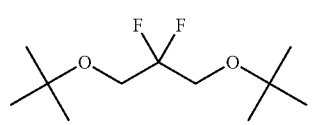 | 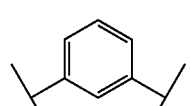 | 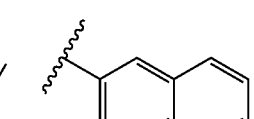 | 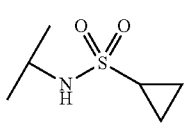 | VI |
| 94. | 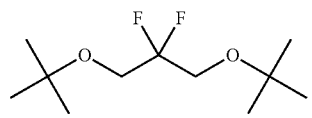 | 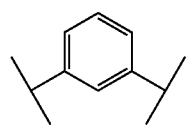 | 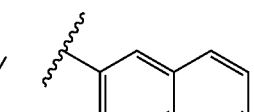 | 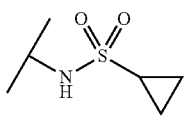 | VII |
| 104. | 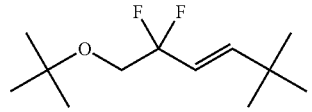 | 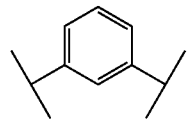 | 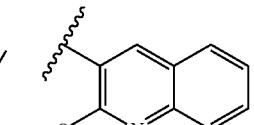 | OH | VI |

TABLE 1-continued
| Example # | M-L | Ar² | Ar¹ | G | Formula |
|---|---|---|---|---|---|
| 105. | 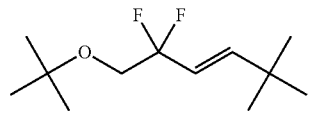 | 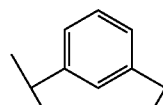 | 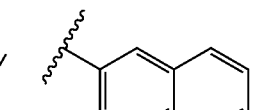 | 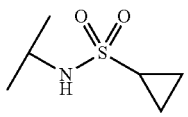 | VI |
| 106. | 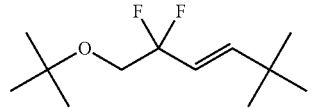 | 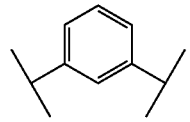 | 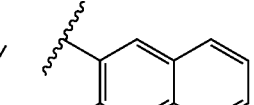 | 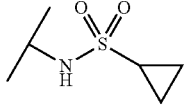 | VII |
| 145. | 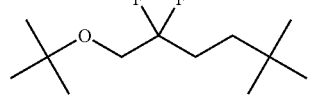 | 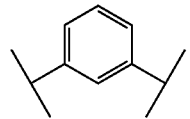 | 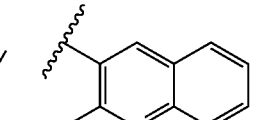 | 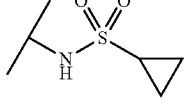 | VI |
| 146. | 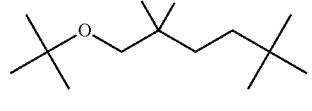 | 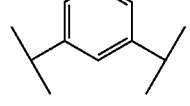 | 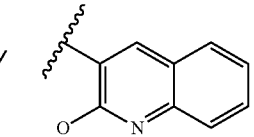 | 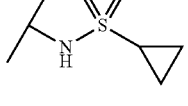 | VII |
| 183. | 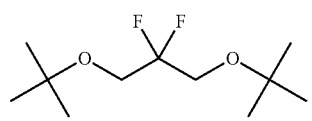 | 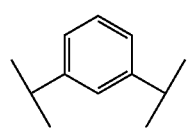 | 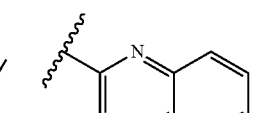 | OH | VI |
| 184. |  | 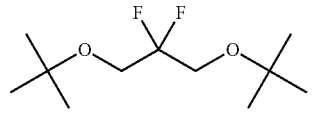 | 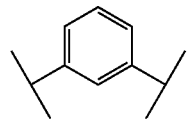 | 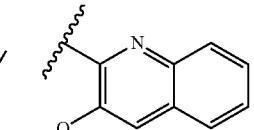 | VI |
| 185. | 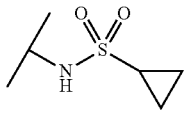 | 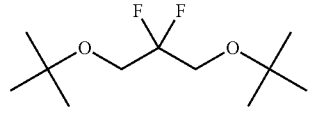 | 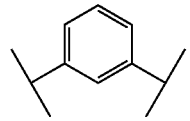 | 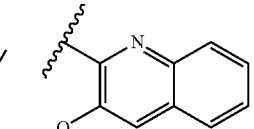 | VII |
| 195. | 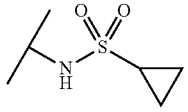 | 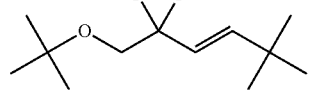 | 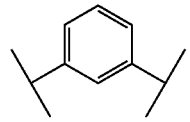 | OH | VI |

TABLE 1-continued
| Example # | M-L | Ar² | Ar¹ | G | Formula |
|---|---|---|---|---|---|
| 196. | 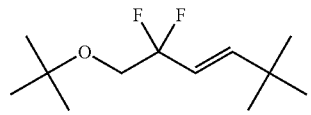 | 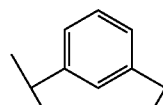 | 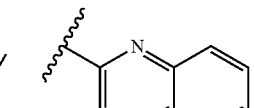 | 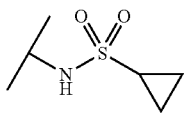 | VI |
| 197. | 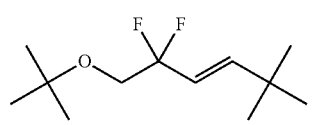 | 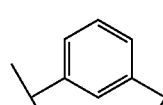 | 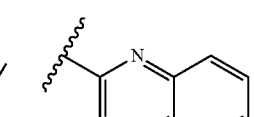 | 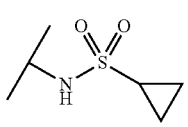 | VII |
| 236. | 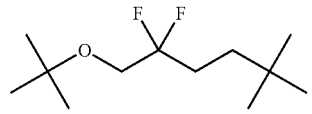 | 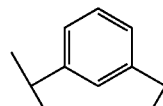 | 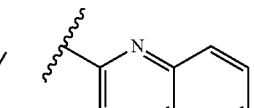 | 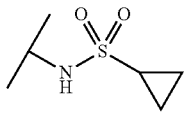 | VI |
| 237. | 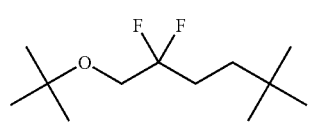 | 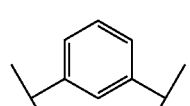 | 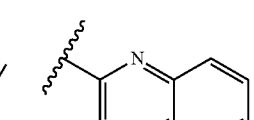 | 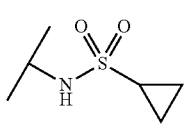 | VII |
| 274. | 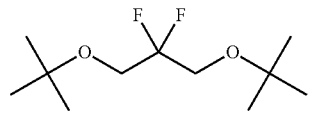 | 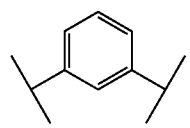 | 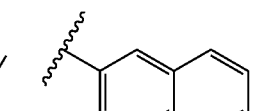 | OH | VI |
| 275. |  | 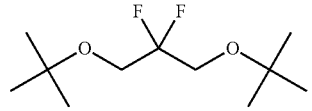 | 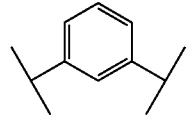 | 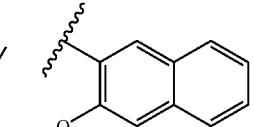 | VI |
| 276. | 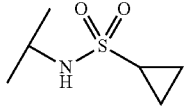 | 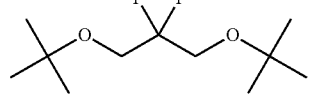 | 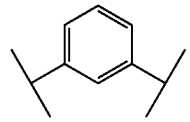 | 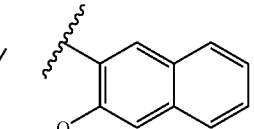 | VII |
| 286. | 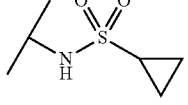 | 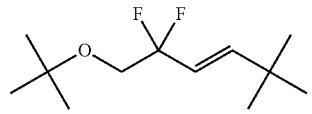 | 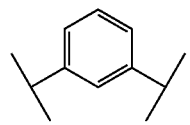 | OH | VI |

TABLE 1-continued
| Example # | M-L | Ar² | Ar¹ | G | Formula |
|---|---|---|---|---|---|
| 287. | 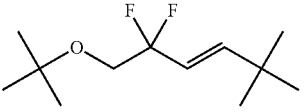 | 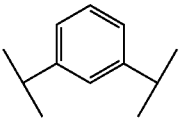 | 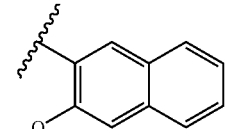 | 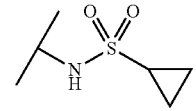 | VI |
| 288. | 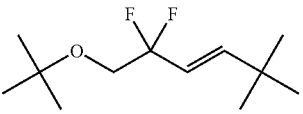 | 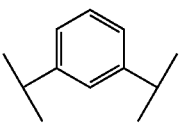 | 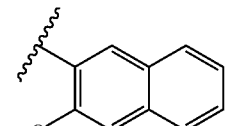 | 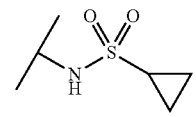 | VII |
| 327. | 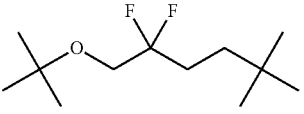 | 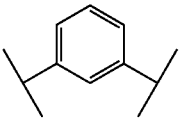 | 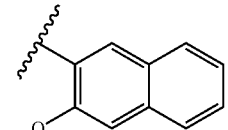 | 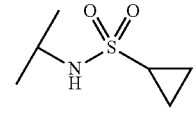 | VI |
| 328. | 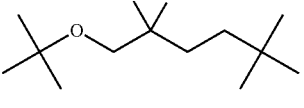 | 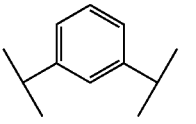 | 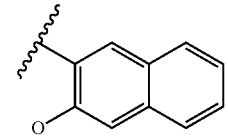 | 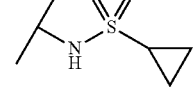 | VII |
| 365. | 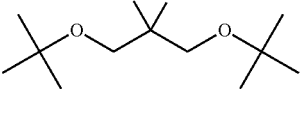 | 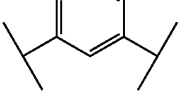 | 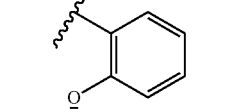 | OH | VI |
| 366. | 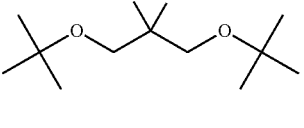 | 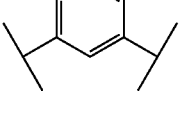 | 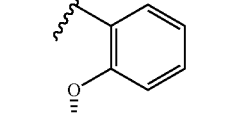 | 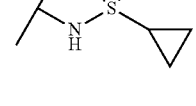 | VI |
| 367. | 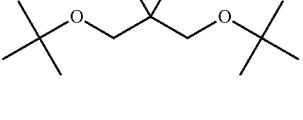 | 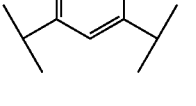 | 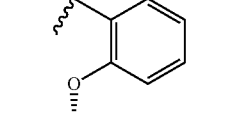 | 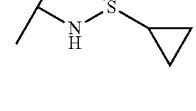 | VII |
| 377. | 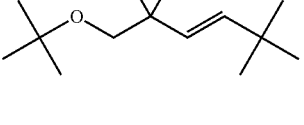 | 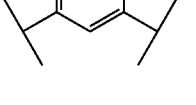 | 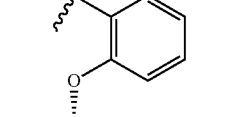 | OH | VI |

TABLE 1-continued

| Example # | M-L | Ar² | Ar¹ | G | Formula |
|---|---|---|---|---|---|
| 378. | 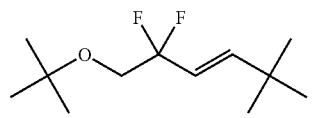 | 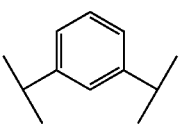 | 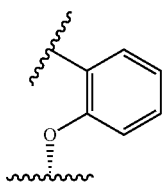 | 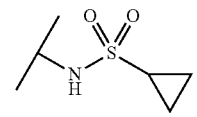 | VI |
| 379. | 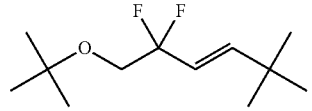 | 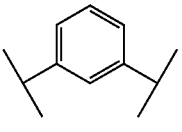 | 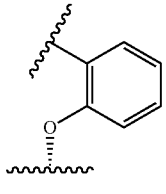 | 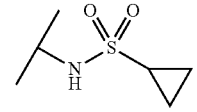 | VII |
| 418. | 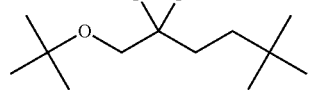 | 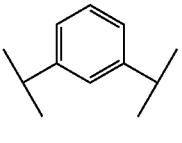 | 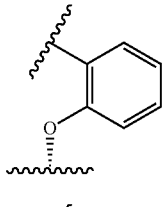 | 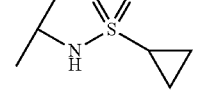 | VI |
| 419. | 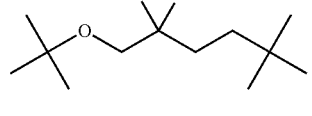 | 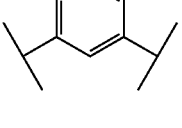 | 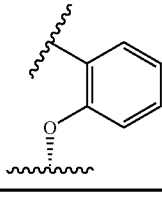 | 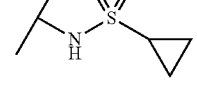 | VII |

5. A pharmaceutical composition comprising a compound according to claim 1 or a pharmaceutically acceptable salt, ester, or prodrug thereof, in combination with a pharmaceutically acceptable carrier or excipient.

6. A method of treating a viral infection in a subject in need thereof, comprising administering to the subject a viral inhibitory amount of a pharmaceutical composition according to claim 5.

7. The method according to claim 6, wherein the viral infection is hepatitis C.

8. A method of inhibiting the replication of hepatitis C virus, the method comprising contacting hepatitis C virus with a hepatitis C viral NS3 protease inhibitory amount of the pharmaceutical composition of claim 5.

9. The method of claim 6, further comprising administering concurrently an additional anti-hepatitis C virus agent.

10. The method of claim 9, wherein said additional anti-hepatitis C virus agent is selected from the group consisting of α-interferon, β-interferon, ribavarin, and amantadine.

11. The method of claim 9, wherein said additional anti-hepatitis C virus agent is an inhibitor of hepatitis C virus helicase, polymerase, metalloprotease, or internal ribosome entry site (IRES).

12. The pharmaceutical composition of claim 5, further comprising another anti-hepatitis C virus agent.

13. The pharmaceutical composition of claim 5, further comprising an agent selected from interferon, ribavirin, amantadine, another HCV protease inhibitor, an HCV polymerase inhibitor, an HCV helicase inhibitor, or an internal ribosome entry site inhibitor.

14. The pharmaceutical composition of claim 5, further comprising pegylated interferon.

15. The pharmaceutical composition of claim 5, further comprising another anti-viral, anti-bacterial, anti-fungal or anti-cancer agent, or an immune modulator.

16. The composition of claim 5, further comprising a cytochrome P450 monooxygenase inhibitor or a pharmaceutically acceptable salt thereof.

17. The composition of claim 16, wherein the cytochrome P450 monooxygenase inhibitor is ritonavir.

18. A method of treating a hepatitis C viral infection in a patient in need thereof comprising administering to the patient a therapeutically effective amount of a cytochrome P450 monooxygenase inhibitor or a pharmaceutically acceptable salt thereof and a therapeutically effective amount of a compound as set forth in claim 1 or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 9,193,740 B2 | Page 1 of 1 |
| APPLICATION NO. | : 12/907614 | |
| DATED | : November 24, 2015 | |
| INVENTOR(S) | : Yonghua Gai et al. | |

It is certified that error appears in the above-identified patent and that said Letters Patent is hereby corrected as shown below:

IN THE CLAIMS

At Column 168

In claim 1, at line 66, delete "MS".

Signed and Sealed this
Twenty-ninth Day of March, 2016

Michelle K. Lee
*Director of the United States Patent and Trademark Office*